(12) United States Patent
Reo et al.

(10) Patent No.: US 8,377,138 B2
(45) Date of Patent: Feb. 19, 2013

(54) PROSTHETIC INTERVERTEBRAL DISCS

(75) Inventors: Michael L. Reo, Redwood City, CA (US); Darin C. Gittings, Sunnyvale, CA (US)

(73) Assignee: Spinal Kinetics Inc., Sunnyvale, CA (US)

( * ) Notice: Subject to any disclaimer, the term of this patent is extended or adjusted under 35 U.S.C. 154(b) by 15 days.

(21) Appl. No.: 12/780,704

(22) Filed: May 14, 2010

(65) Prior Publication Data

US 2011/0054620 A1    Mar. 3, 2011

Related U.S. Application Data

(63) Continuation of application No. 11/281,205, filed on Nov. 15, 2005, now Pat. No. 7,731,753.

(60) Provisional application No. 60/713,671, filed on Sep. 1, 2005.

(51) Int. Cl.
*A61F 2/44* (2006.01)

(52) U.S. Cl. .................................. 623/17.16; 623/17.13

(58) Field of Classification Search .... 623/17.11–17.16; 606/246
See application file for complete search history.

(56) References Cited

U.S. PATENT DOCUMENTS

| | | | |
|---|---|---|---|
| 3,867,728 A | 2/1975 | Stubstad | |
| 4,932,969 A | 6/1990 | Frey et al. | |
| 5,071,437 A | 12/1991 | Steffee | |
| 5,171,281 A | 12/1992 | Parsons et al. | |
| 5,370,697 A | 12/1994 | Baumgartner | |
| 6,063,121 A * | 5/2000 | Xavier et al. | 623/17.15 |
| 6,626,943 B2 | 9/2003 | Eberlin et al. | |
| 6,645,248 B2 | 11/2003 | Casutt | |
| 6,733,532 B1 * | 5/2004 | Gauchet et al. | 623/17.12 |
| 7,153,325 B2 * | 12/2006 | Kim et al. | 623/17.15 |
| 7,563,284 B2 | 7/2009 | Coppes et al. | |
| 7,566,346 B2 * | 7/2009 | Kirschman | 623/17.14 |

OTHER PUBLICATIONS

U.S. Appl. No. 60/403,356, Provisional Application, filed Aug. 15, 2002.
U.S. Appl. No. 60/403,402, Provisional Application, filed Aug. 15, 2002.
Spinel Kinetics, Inc.'s Preliminary Invalidity Contentions (USDC, Case No. 5:09-cv-01201, *Synthes USA et al. v. Spinal Kinetics, Inc.*, Sep. 8, 2009).
Spinal Kinetics, Inc.'s Preliminary Invalidity Contentions—Exhibit 1 (chart comparing claims of USP 7,429,270 to Stubstad USP 3,867,728).
Spinal Kinetics, Inc.'s Preliminary Invalidity Contentions—Exhibit 2 (chart comparing claims of USP 7,429,270 to Baumgartner USP 5,370,697 in view of Stubstad USP 3,867,728 and Steffee USP 5,071,437).
Spinal Kinetics, Inc.'s Preliminary Invalidity Contentions—Exhibit 3 (chart comparing claims of USP 7,429,270 to Baumgartner USP 5,370,697 in view of Stubstad USP 3,867,728 and Parsons USP 5,171,281).
Spinal Kinetics, Inc.'s Preliminary Invalidity Contentions—Exhibit 4 (chart comparing claims of USP 7,429,270 to Baumgartner USP 5,370,697 in view of Substad USP 3,867,728 and Eberlein USP 6,626,943).

(Continued)

*Primary Examiner* — Pedro Philogene
(74) *Attorney, Agent, or Firm* — E. Thomas Wheelock

(57) ABSTRACT

Prosthetic intervertebral discs, systems including such prosthetic intervertebral discs, and methods for using the same are described. The subject prosthetic discs include upper and lower endplates separated by a compressible core member. The subject prosthetic discs exhibit stiffness in the vertical direction, torsional stiffness, bending stiffness in the saggital plane, and bending stiffness in the front plane, where the degree of these features can be controlled independently by adjusting the components, construction, and other features of the discs.

34 Claims, 36 Drawing Sheets

OTHER PUBLICATIONS

Figure 1A:
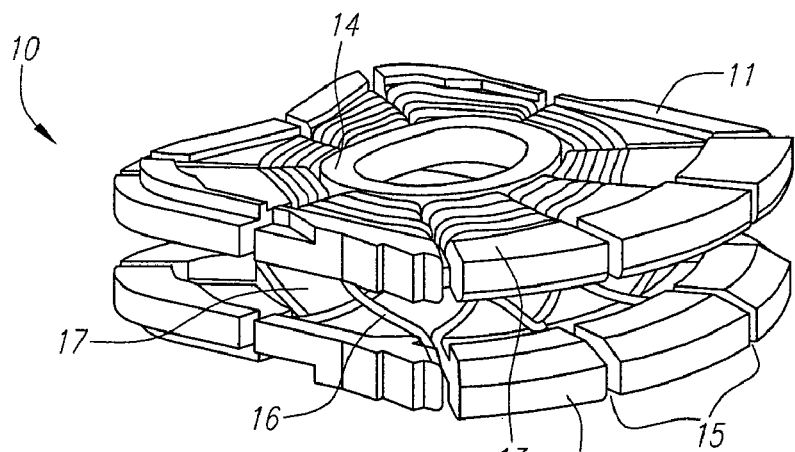

Spinal Kinetics, Inc.'s Preliminary Invalidity Contentions—Exhibit 5 (chart comparing claims of USP 7,429,270 to Baumgartner USP 5,370,697 in view of Substad USP 3,867,728 and Casutt USP 6,645,248).
Spinal Kinetics, Inc.'s Preliminary Invalidity Contentions—Exhibit 6 (chart comparing claims of USP 7,429,270 to Baumgartner USP 5,370,697 in view of Substad 3,867,728 and Frey USP 4,932,969).
Spinal Kinetics, Inc.'s Preliminary Invalidity Contentions—Exhibit 7 (chart comparing claims of USP 7,429,270 to Baumgartner USP 5,370,697 in view of Stubstad USP 3,867,728 and Gauchet USP 6,733,532).
Spinal Kinetics, Inc.'s Preliminary Invalidity Contentions—Exhibit 8 (chart comparing claims of USP 7,429,270 to Baumgartner USP 5,370,697 in view of Stubstad USP 3,867,728 and Development and Characterization of a Prosthetic Intervertebral Disc, Robert Hudgins, Georgia Inst. Of Tech., Nov. 1998).
Spinal Kinetics, Inc.'s Preliminary Invalidity Contentions—Exhibit 9 (chart comparing claims of USP 7,429,270 to Stubstad USP 3,867,728 i view of Baumgartner USP 5,370,697).
Spinal Kinetics, Inc.'s Preliminary Invalidity Contentions—Exhibit 10 (chart comparing claims of USP 7,429,270 to Baumgartner USP 5,370,697 in view of Stubstad USP 3,867,728 and Steffe USP 4,071,437).
Spinal Kinetics, Inc.'s Preliminary Invalidity Contentions—Exhibit 11 (chart comparing claims of USP 7,429,270 to Baumgartner USP 5,370,697 in view of Stubstad USP 3,867,728 and Casutt USP 6,645,248).
Spinal Kinetics, Inc.'s Preliminary Invalidity Contentions—Exhibit 12 (chart comparing claims of USP 7,429,270 to Stubstad USP 3,867,728 in view of Development and Characterization of a Prosthetic Intervertebral Disc, Robert Hudgins, Georgia Inst. Of Tech., Nov. 1998).
Spinal Kinetics, Inc.'s Preliminary Invalidity Contentions [Amended] (USDC, Case No. 5:09-cv-01201, *Synthes USA et al.* v. *Spinal Kinetics, Inc.*, Dec. 28, 2009).
Spinal Kinetics, Inc.'s Preliminary Invalidity Contentions [Amended]—Exhibit 1 (chart comparing claims of USP 7,429,270 to Stubstad USP 3,867,728).
Spinal Kinetics, Inc.'s Preliminary Invalidity Contentions [Amended]—Exhibit 2 (chart comparing claims of USP 7,429,270 to Coppes USP 7,563,284).
Spinal Kinetics, Inc.'s Preliminary Invalidity Contentions [Amended]—Exhibit 3 (chart comparing claims of USP 7,429,270 to Coppes USP 7,563,284 in combination with Stubstad USP 3,867,728).
Spinal Kinetics, Inc.'s Preliminary Invalidity Contentions [Amended]—Exhibit 4 (chart comparing claims of USP 7,429,270 to Baumgartner USP 5,370,697 in view of Stubstad USP 3,867,728 and Steffee USP 5,071,437).
Spinal Kinetics, Inc.'s Preliminary Invalidity Contentions [Amended]—Exhibit 5 (chart comparing claims of USP 7,429,270 to Baumgartner USP 5,370,697 in view of Stubstad USP 3,867,728 and Parsons USP 5,171,281).
Spinal Kinetics, Inc.'s Preliminary Invalidity Contentions [Amended]—Exhibit 6 (chart comparing claims of USP 7,429,270 to Baumgartner USP 5,370,697 in view of Stubstad USP 3,867,728 and Eberlein USP 6,626,943).
Spinal Kinetics, Inc.'s Preliminary Invalidity Contentions [Amended]—Exhibit 7 (chart comparing claims of USP 7,429,270 to Baumgartner USP 5,370,697 in view of Stubstad USP 3,867,728 and Casutt USP 6,645,248).
Spinal Kinetics, Inc.'s Preliminary Invalidity Contentions [Amended]—Exhibit 8 (chart comparing claims of USP 7,429,270 to Baumgartner USP 5,370,697 in view of Stubstad USP 3,867,728 and Frey USP 4,932,969).
Spinal Kinetics, Inc.'s Preliminary Invalidity Contentions [Amended]—Exhibit 9 (chart comparing claims of USP 7,429,270 to Baumgartner USP 5,370,697 in view of Stubstad USP 3,867,728 and Gauchet USP 6,733,532).
Spinal Kinetics, Inc.'s Preliminary Invalidity Contentions [Amended]—Exhibit 10 (chart comparing claims of USP 7,429,270 to Baumgartner USP 5,370,697 in view of Stubstad USP 3,867,728 and Development and Characterization of a Prosthetic Intervertebral Disc, Hudgins, Georgia Inst. Of Tech., Nov. 1998).
Spinal Kinetics, Inc.'s Preliminary Invalidity Contentions [Amended]—Exhibit 11 (chart comparing claims of USP 7,429,270 to Stubstad USP 3,867,728 in view of Baumgartner USP 5,370,697).
Spinal Kinetics, Inc.'s Preliminary Invalidity Contentions [Amended]—Exhibit 12 (chart comparing claims of USP 7,429,270 to Baumgartner USP 5,370,697 in view of Stubstad USP 3,867,728 and Steffee USP 4,071,437).
Spinal Kinetics, Inc.'s Preliminary Invalidity Contentions [Amended]—Exhibit 13 (chart comparing claims of USP 7,429,270 to Baumgartner USP 5,370,697 in view of Stubstad USP 3,867,728 and Casutt USP 6,645,248).
Spinal Kinetics, Inc.'s Preliminary Invalidity Contentions [Amended]—Exhibit 14 (chart comparing claims of USP 7,429,270 to Stubstad USP 3,867,728 in view of Development and Characterization of a Prosthetic Intervertebral Disc, Hudgins, Georgia Inst. Of Tech., Nov. 1998).
Spinal Kinetics, Inc.'s Preliminary Invalidity Contentions (USDC, Case No. 5:09-cv-01201, *Synthes USA et al.* v. *Spinal Kinetics, Inc.*, Sep. 30, 2010).
Spinal Kinetics, Inc.'s Preliminary Invalidity Contentions —Exhibit 1 (chart comparing claims of USP 7,429,270 to Neuentwicklung eines Implantates für den totalen Bandschiabenersatz, Vorgelegt con: Adrian Burri und Daniel Baumgartner Im Rahmen des Studiums für "Maschinenbau und Vergahrenstechnik" an der Eldgenöossischen Technischen Hochschule Zürich, im Februar 2002).
Spinal Kinetics, Inc.'s Preliminary Invalidity Contentions —Exhibit 2 (chart comparing claims of USP 7,429,270 to Neuentwicklung eines lumbalen bewegungserhaltenden Bandscheibenimplantates, Feb. 25, 2002).
Spinal Kinetics, Inc.'s Preliminary Invalidity Contentions —Exhibit 3 (chart comparing claims of USP 7,429,270 to Stubstad USP 3,867,728).
Spinal Kinetics, Inc.'s Preliminary Invalidity Contentions —Exhibit 4 (chart comparing claims of USP 7,429,270 to Baumgartner PCT/CH2003/00247).
Spinal Kinetics, Inc.'s Preliminary Invalidity Contentions —Exhibit 5 (chart comparing claims of USP 7,429,270 to Neuentwicklung eines Implantate für den totalen Bandschiebenersalz, Vorgelegt von: Adrian Burri und Daniel Baumgartner Im Rahmen des Studiums für "Maschinenbau und Vergahrenstechnik" an der Eidfenöossischen Technischen Hochschule Zürich, im Februar 2002).
Spinal Kinetics, Inc.'s Preliminary Invalidity Contentions —Exhibit 6 (chart comparinf claims of USP 7,429,270 to Neuentwicklung eines Implantates für den totalen Bandschiebenersalz, Vorgelogt von: Adrian Burri und Daniel Baumgartner Im Rahmen des Studiums für "Maschinenbau und Vergahrenstechnik" an der Eidgenöossischen Technischen Hochschuie Zürich, im Februar 2002).
Spinal Kinetics, Inc.'s Preliminary Invalidity Contentions —Exhibit 7 (chart comparing claims of USP 7,429,270 to Stubstad USP 3,867,728 in view of Eberlein USP 6,626,943).
Spinal Kinetics, Inc.'s Preliminary Invalidity Contentions —Exhibit 8 (chart comparing claims of USP 7,429,270 to Stubstad 3,867,728 in view of Kim USP 7,153,325).
Spinal Kinetics, Inc.'s Preliminary Invalidity Contentions —Exhibit 9 (chart comparing claims of USP 7,429,270 to Stubstad USP 3,867,728 in view of Optimal Design of Synthetic Intervertebral Disc Prosthesis Considering Nonlinear Mechanical Behavior, Kweon et al., Dec. 20, 2001).
Spinal Kinetics, Inc.'s Preliminary Invalidity Contentions —Exhibit 10 (chart comparing claims of USP 7,429,270 to Stubstad 3,867,728 in view of Development and Characterization of a Prosthetic Intervertebral Disc, Hudgins, Georgia Inst. Of Tech., Nov. 1998).
Spinal Kinetics, Inc.'s Preliminary Invalidity Contentions —Exhibit 11 (chart comparing claims of USP 7,429,270 to Coppes USP 7,563,284 to Stubstad USP 3,867,728).
Spinal Kinetics, Inc.'s Preliminary Invalidity Contentions —Exhibit 12 (chart comparing claims of USP 7,429,270 to Coppes USP 7,563,284 in view of Eberlein USP 6,626,943).

Spinal Kinetics, Inc.'s Preliminary Invalidity Contentions —Exhibit 13 (chart comparins claims of USP 7,429,270 to Coppes USP 7,563,284 in view of Kim USP 7,153,325).
Spinal Kinetics, Inc.'s Preliminary Invalidity Contentions —Exhibit 14 (chart comparing claims of USP 7,429,270 to Coppes USP 7,563,284 in view of Optimal Design of Synthetic Intervertebral Disc Prosthesis Considering Nonlinear Mechanical Behavior, Kweon et al., Dec. 20, 2001).
Spinal Kinetics, Inc.'s Preliminary Invalidity Contentions —Exhibit 15 (chart comparing claims of USP 7,429,270 to Coppes USP 7,563,284 in view of Development and Characterization of a Prostethic Intervertebral Disc, Hudgins, Georgia Inst. Of Tech., Nov. 1998).
Spinal Kinetics, Inc.'s Preliminary Invalidity Contentions —Exhibit 16 (chart comparing claims of USP 7,429,270 to Baumgartner USP 5,370,697 in view of Stubstad USP 3,867,728).
Spinal Kinetics, Inc.'s Preliminary Invalidity Contentions —Exhibit 17 (chart comparing claims of USP 7,429,270 to Baumgartner USP 5,370,697 in view of Eberlein USP 6,626,943).
Spinal Kinetics, Inc.'s Preliminary Invalidity Contentions —Exhibit 18 (chart comparing claims of USP 7,429,270 to Baumgartner USP 5,370,697 in view of Kim USP 7,153,325).
Spinal Kinetics, Inc.'s Preliminary Invalidity Contentions —Exhibit 19 (chart comparing claims of USP 7,429,270 to Baumgartner USP 5,370,697 in view of Optimal Design of Synthetic Intervertebral Disc Prosthesis Considering Nonlinear Mechanical Behavior, Kweon et al., Dec. 20, 2001).
Spinal Kinetics, Inc.'s Preliminary Invalidity Contentions —Exhibit 20 (chart comparing claims of USP 7,429,270 to Baumgartner USP 5,370,697 in view of Development and Characterization of a Prosthetic Intervertebral Disc, Hdgins, Georgia Inst. Of Tech., Nov. 1998).
Spinal Kinetics, Inc.'s Preliminary Invalidity Contentions —Exhibit 21 (chart comparing claims of USP 7,429,270 to Gauchet USP 6,733,532 in view of Stubstad USP 3,867,728).
Spinal Kinetics, Inc.'s Preliminary Invalidity Contentions —Exhibit 22 (chart comparing claims of USP 7,429,270 to Gauchet USP 6,733,532 in view of Eberlein USP 6,626,943).
Spinal Kinetics, Inc.'s Preliminary Invalidity Contentions —Exhibit 23 (chart comparing claims of USP 7,429,270 to Gauchet USP 6,733,532 in view of Kim USP 7,153,325).
Spinal Kinetics, Inc.'s Preliminary Invalidity Contentions —Exhibit 24 (chart comparing claims of USP 7,429,270 to Gauchet USP 6,733,532 in view of Optimal Design of Synthetic Intervertebral Disc Prosthesis Considering Nonlinear Mechanical Behavior, Kweon et al., Dec. 20, 2001).
Spinal Kinetics, Inc.'s Preliminary Invalidity Contentions —Exhibit 25 (chart comparing claims of USP 7,429,270 to Gauchet USP 5,733,532 in view of Development and Characterization of a Prosthetic Intervertebral Disc, Hudgins, Georgia Inst. Of Tech., Nov. 1998).
Spinal Kinetics, Inc.'s Preliminary Invalidity Contentions —Exhibit 26 (chart comparing claims of USP 7,429,270 to Baumgartner USP 5,370,697 in view of Stubstad USP 3,867,728).
Spinal Kinetics, Inc.'s Preliminary Invalidity Contentions —Exhibit 27 (chart comparing claims of USP 7,429,270 to Coppes USP 7,563,284 in view of Stubstad USP 3,867,728).
Spinal Kinetics, Inc.'s Preliminary Invalidity Contentions —Exhibit 28 (chart comparing claims of USP 7,429,270 to Baumgartner USP 5,370,697 in view of Stubstad USP 3,867,728 in further view of Development and Characterization of a Prosthetic Intervertebral Disc, Hudgins, Georgia Inst. Of Tech., Nov. 1998).
Spinal Kinetics, Inc.'s Preliminary Invalidity Contentions —Exhibit 29 (chart comparing claims of USP 7,429,270 to Coppes USP 7,563,284 in view of Stubstad USP 3,867,728 further in view of Development and Characterization of a Prosthetic Intervertebral Disc, Hudgins, Georgia Inst. Of Tech., Nov. 1998).
Burri et al., Neuentwicklung eines Implantates für den totalen Bandschiebenersatz, Vorgelegt von: Im Rahmen des Studium für "Maschinenbau und Vergahrenstechnik" an der Eidgenöossischen Technischen Hochschule Zürich, im Februar 2002).
English Translation of Burri et al., Neuentqicklung eines Implantates für den totalen Bandschiebenersatz, Vorgelegt con: Im Rahmen des Studiums für "Maschinenbau und Vergahrenstechinik" an der Eidgenöossischen Technischen Hochschule Zürich, im Februar 2002), entitled Mechanical Engineering and Process Engineering at the Swiss Fedearl Institute of Technology Zurich (ETH Zurich) Feb. 2002.
Burri et al., Neuentwicklung eines lumbalen bewegungsehaltenden Bandscheibenimplantates, Feb. 25, 2002.
English Translation of Burri et al., Neuentwicklung eines lumbalen bewegungserhaltenden Bandscheibenimplantates, Feb. 25, 2002.
Hudgins, Development and Characterizatioin of a Prostetic Intervertebral Disc, Hudgins, Georgia Inst. Of Tech., Nov. 1998.
Kweon et al., Optimal Design of Synthetic Intervertebral Disc Prosthesis Considering Nonlinear Mechanical Behavior, Dec. 20, 2001.

* cited by examiner

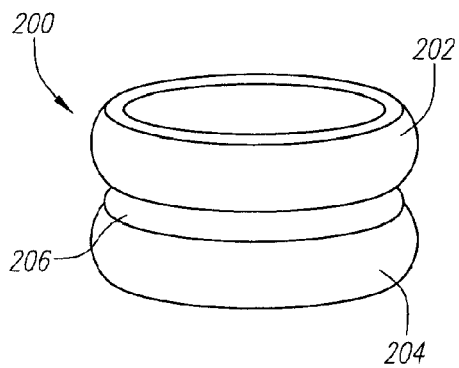
FIG. 6H
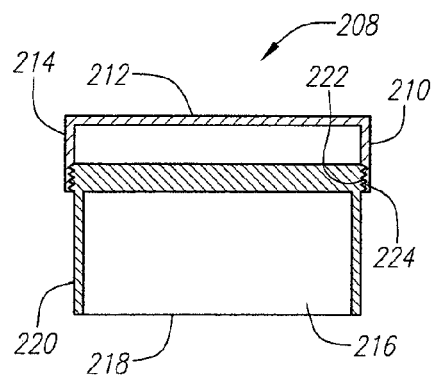
FIG. 6I
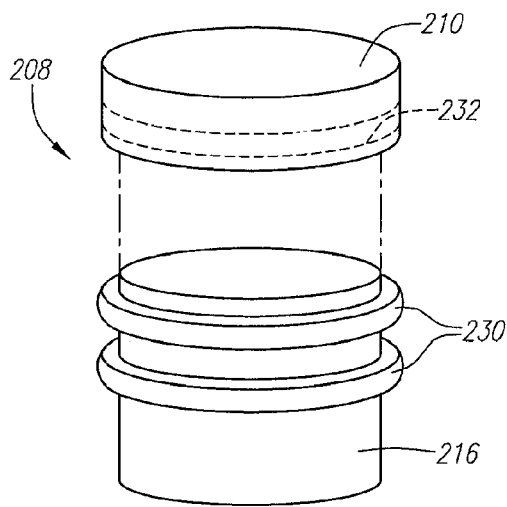
FIG. 6J
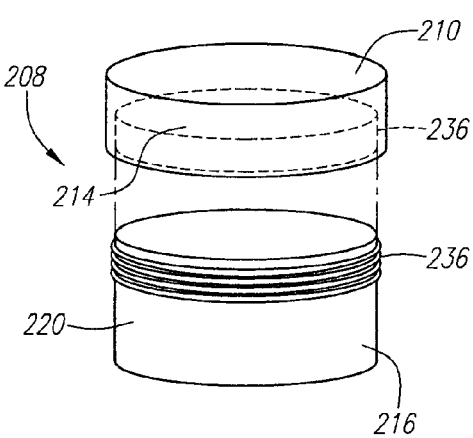
FIG. 6K
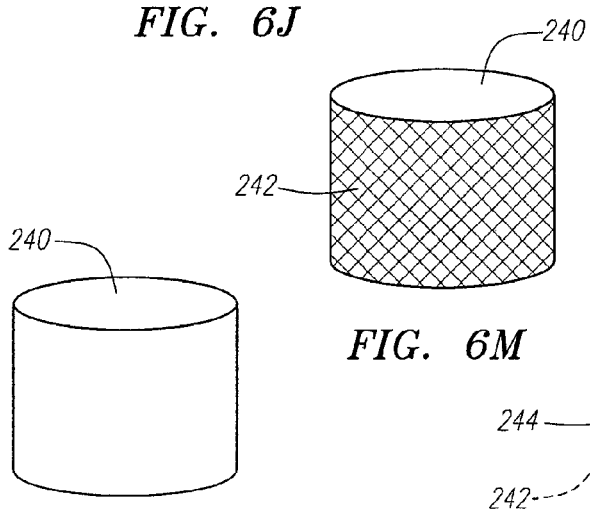
FIG. 6L
FIG. 6M
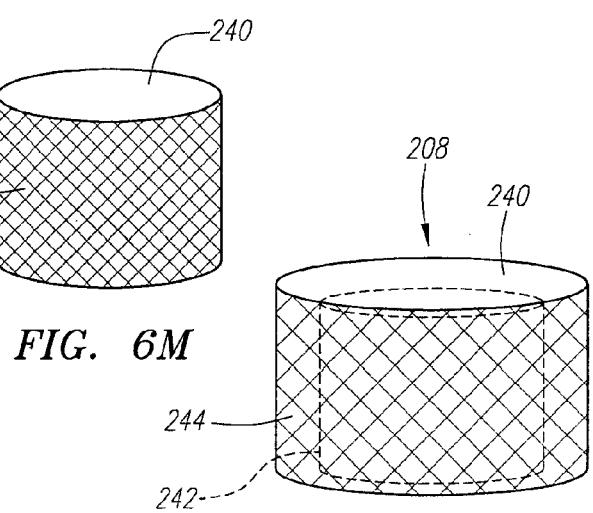
FIG. 6N

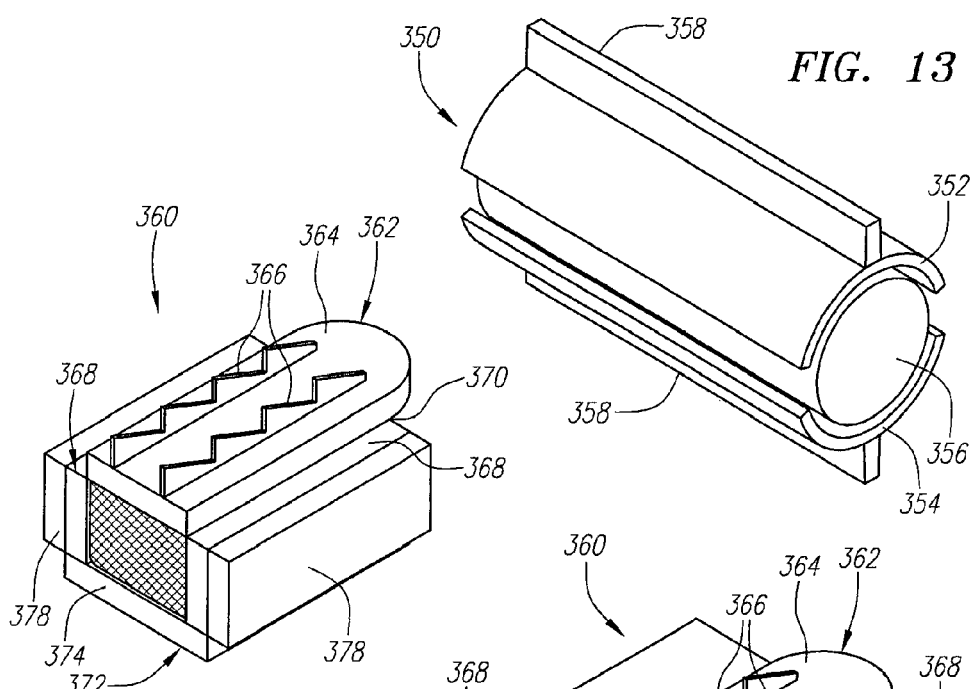
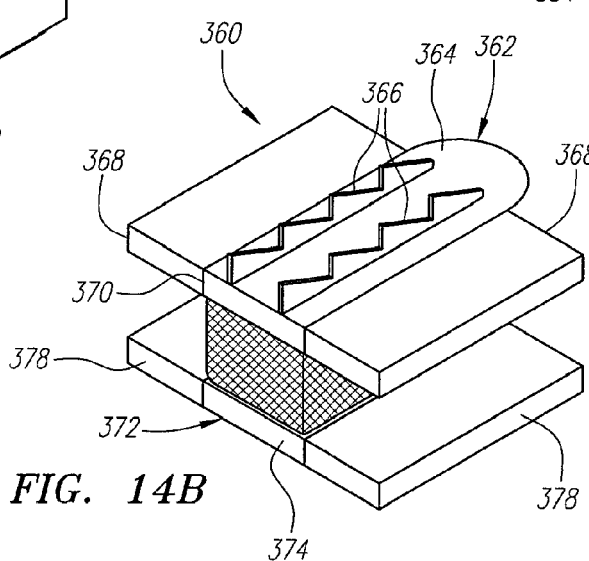
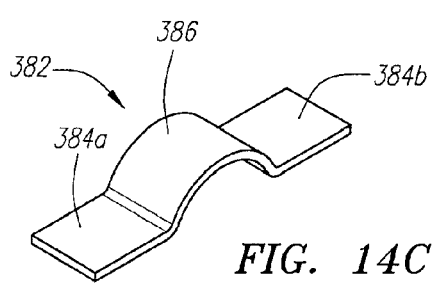
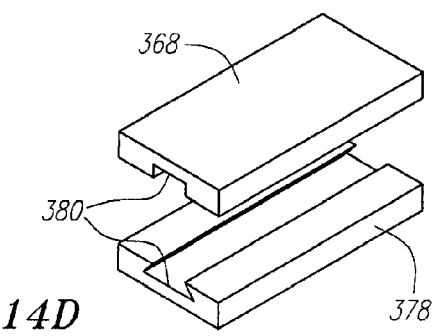

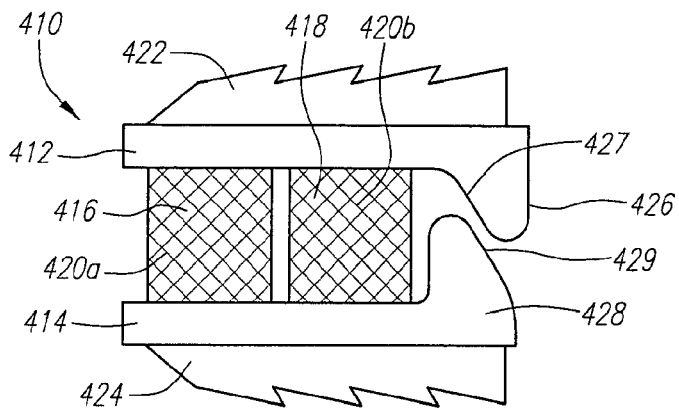
*FIG. 17A*
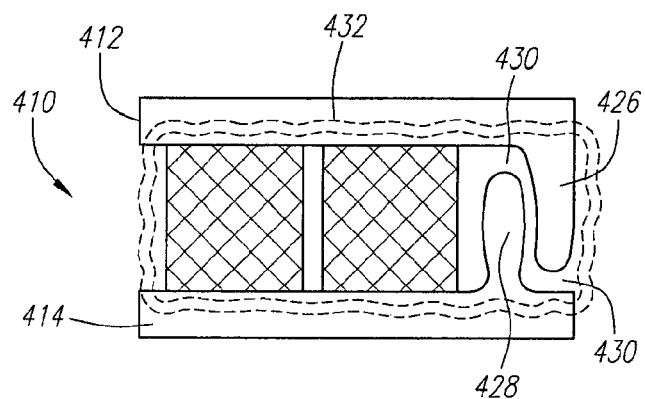
*FIG. 17B*
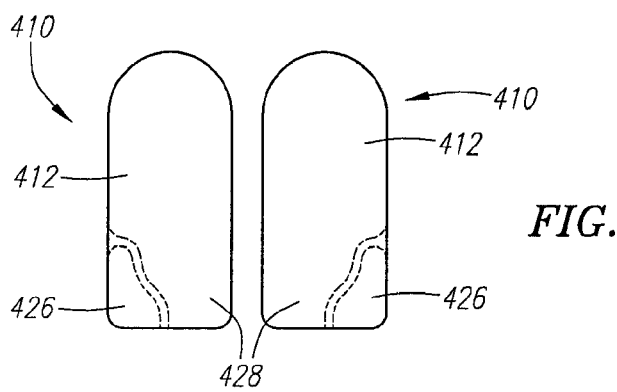
*FIG. 18A*
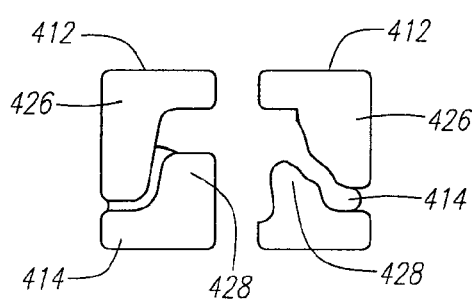
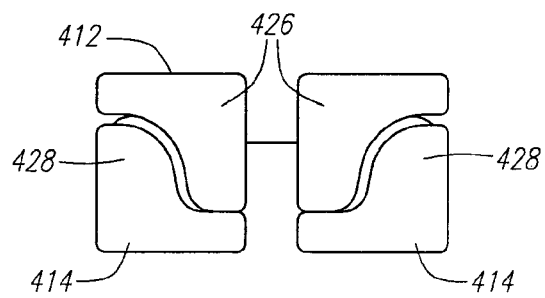
*FIG. 18B*  *FIG. 18C*

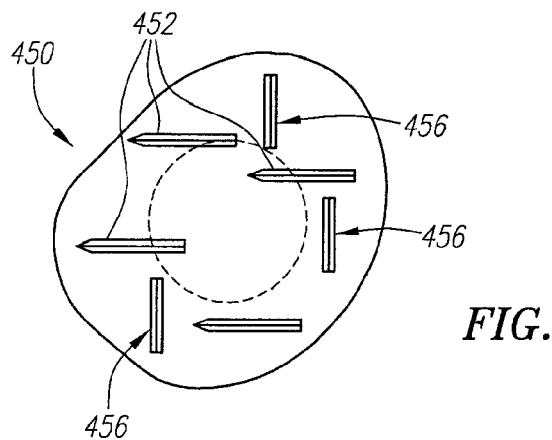
FIG. 22A
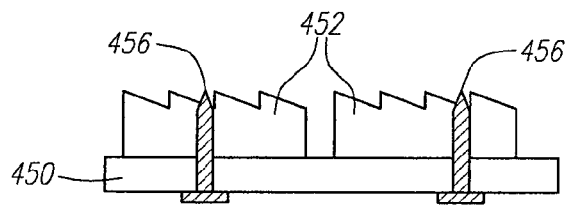
FIG. 22B
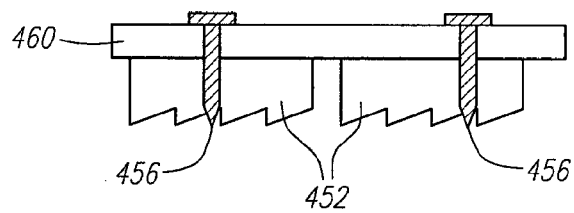
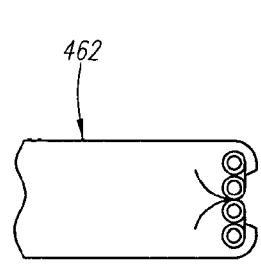
FIG. 22D
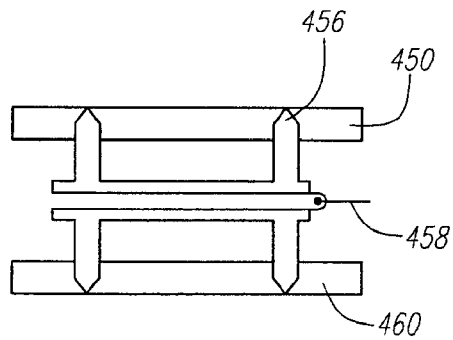
FIG. 22C

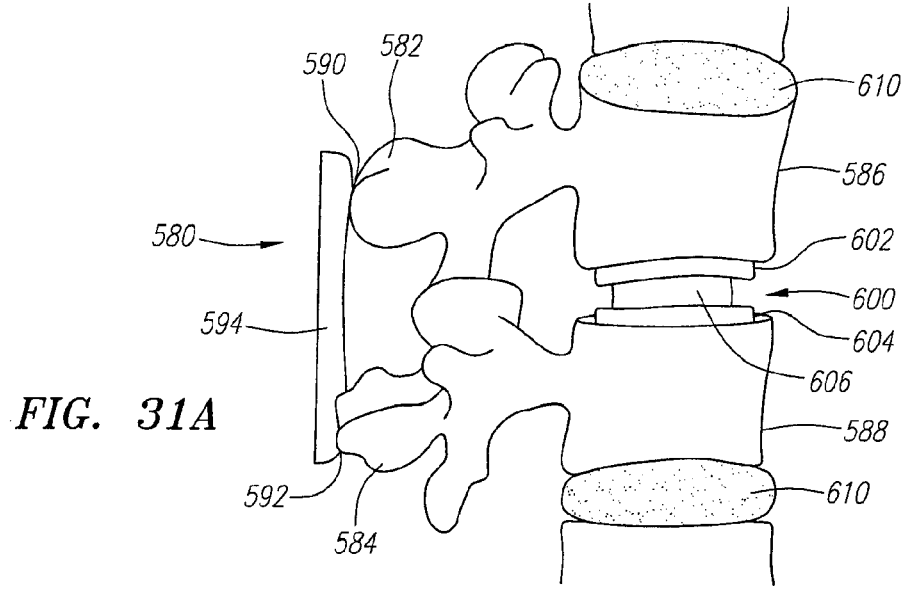
FIG. 31A
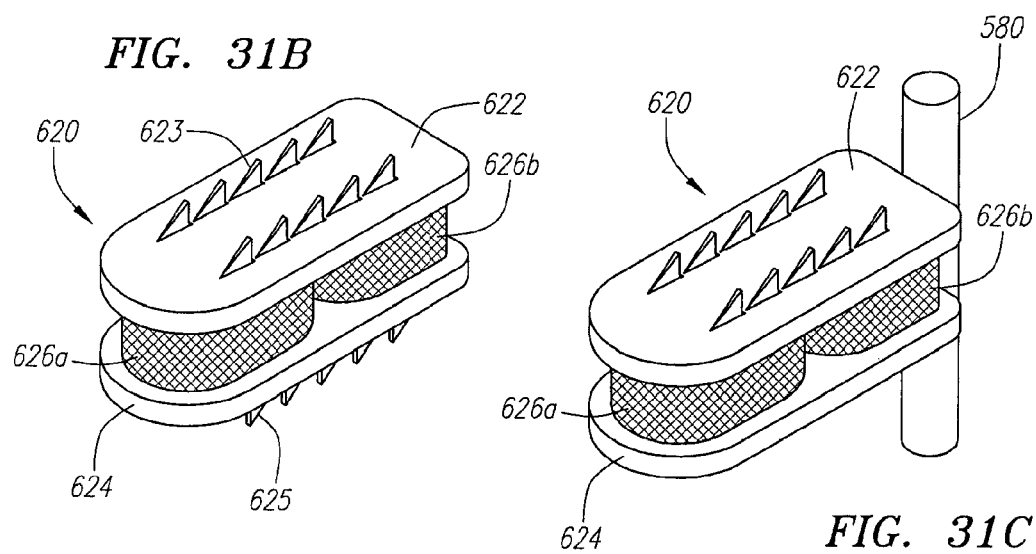
FIG. 31B
FIG. 31C
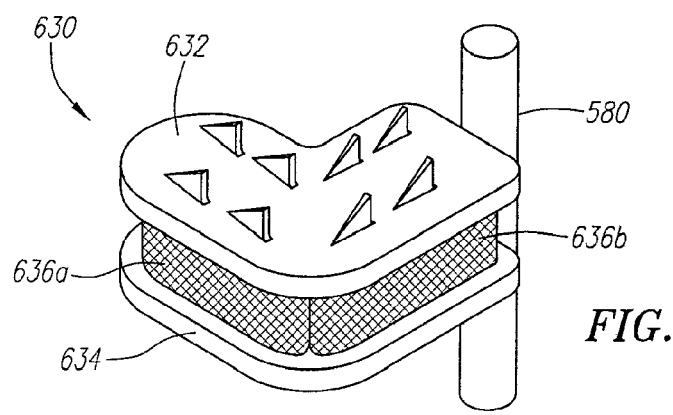
FIG. 31D

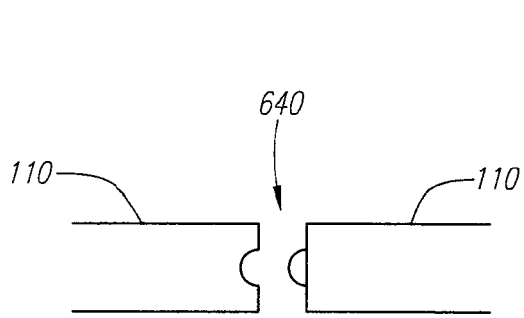 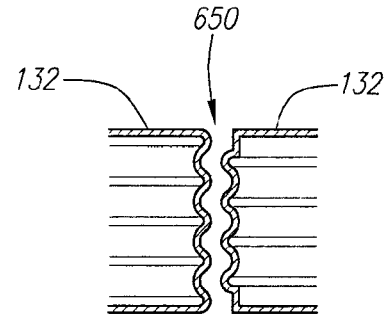
FIG. 32A  FIG. 32B
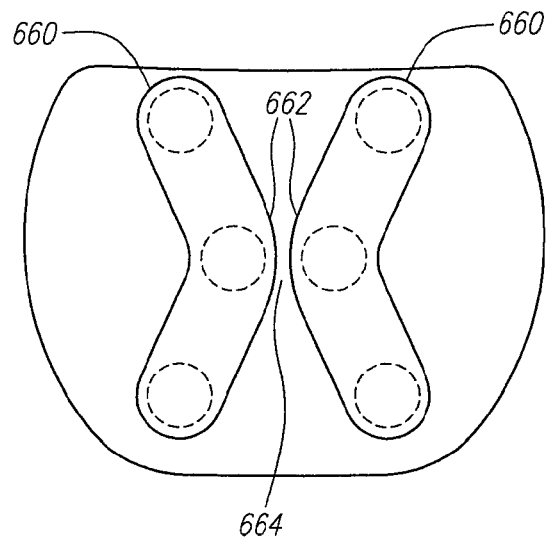
FIG. 33A
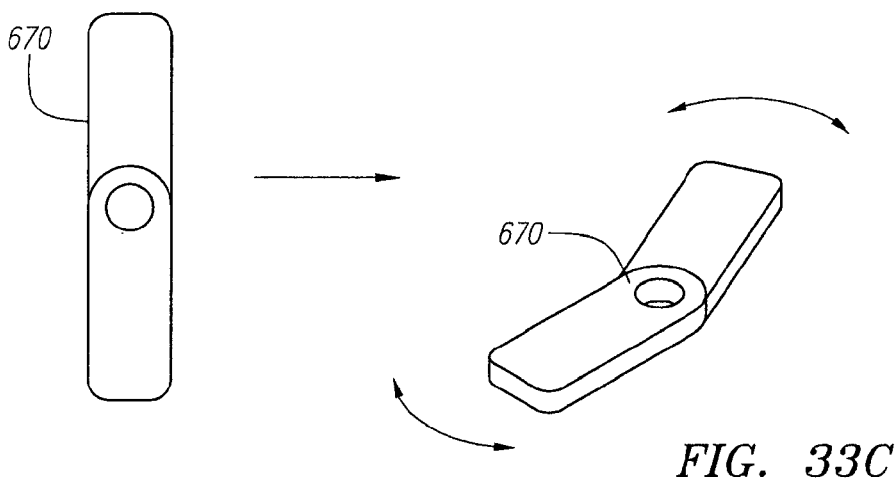
FIG. 33B  FIG. 33C

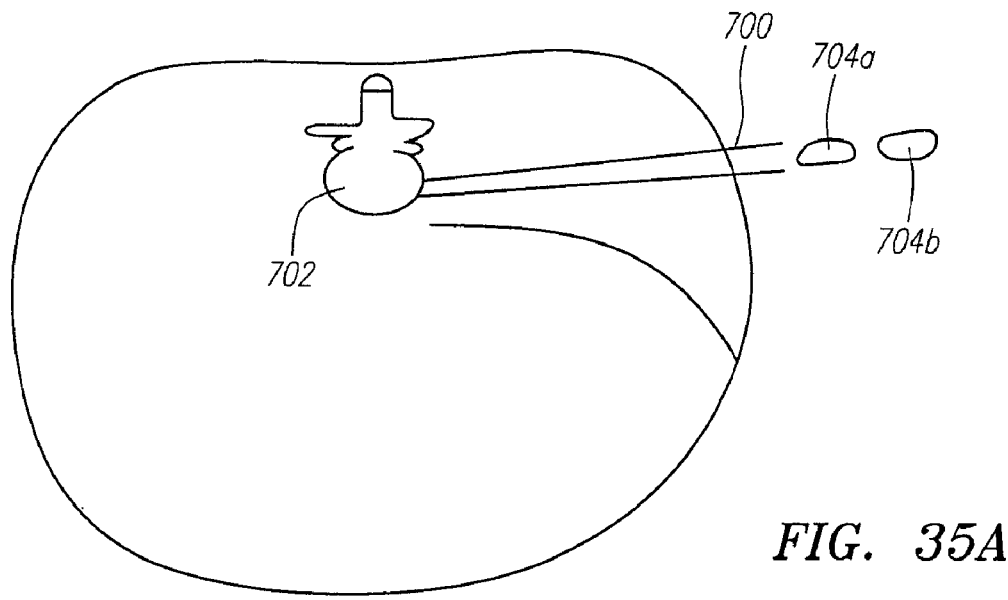
*FIG. 35A*
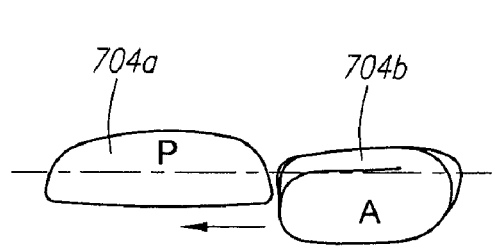   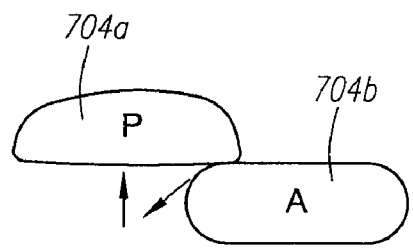
*FIG. 35B*   *FIG. 35C*
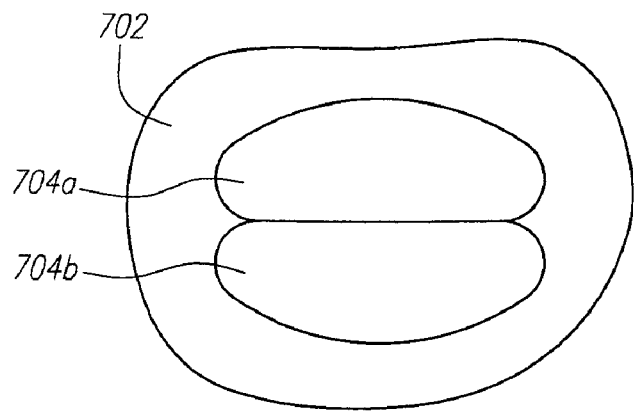
*FIG. 35D*

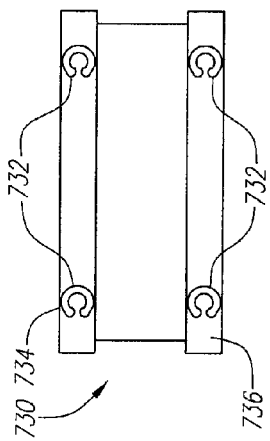
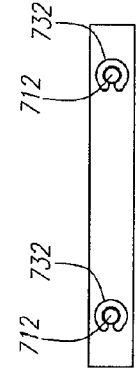
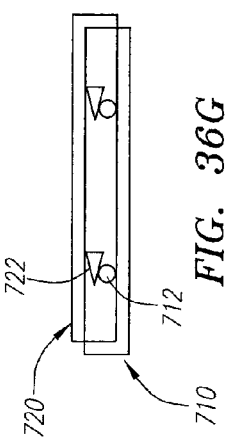
FIG. 36E  FIG. 36F  FIG. 36I
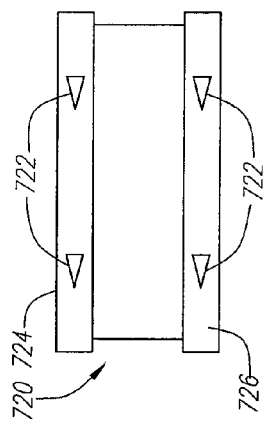
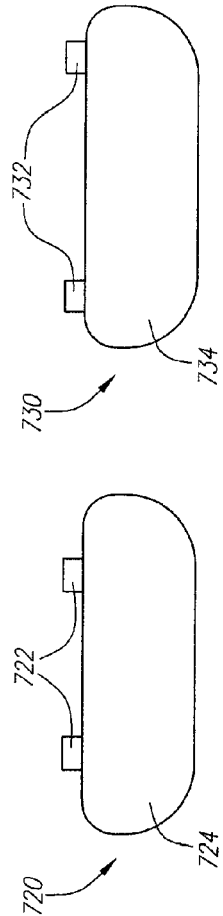
FIG. 36C  FIG. 36D  FIG. 36H
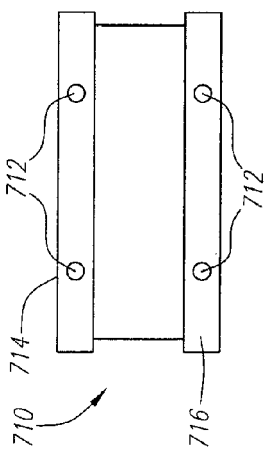
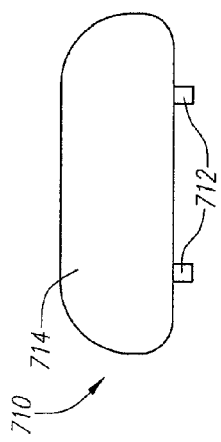
FIG. 36A  FIG. 36B  FIG. 36G

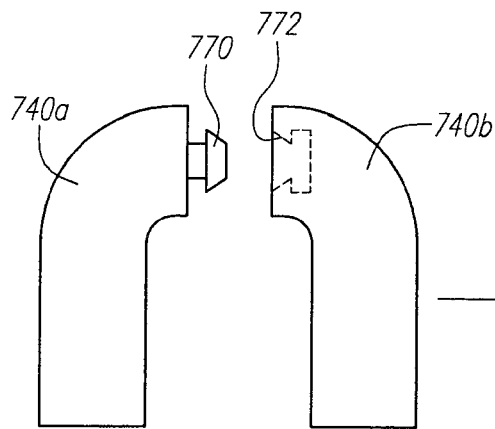
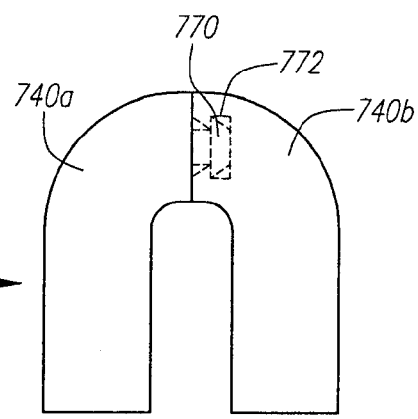
FIG. 38A　　　　　　FIG. 38B
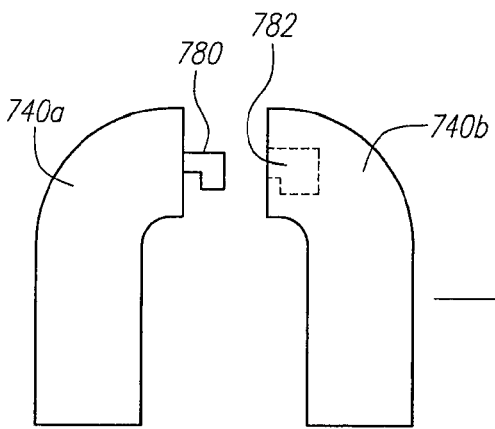
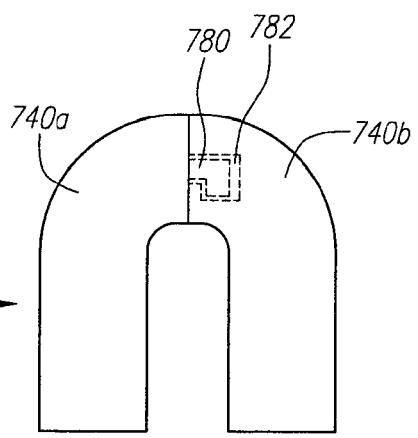
FIG. 38C　　　　　　FIG. 38D
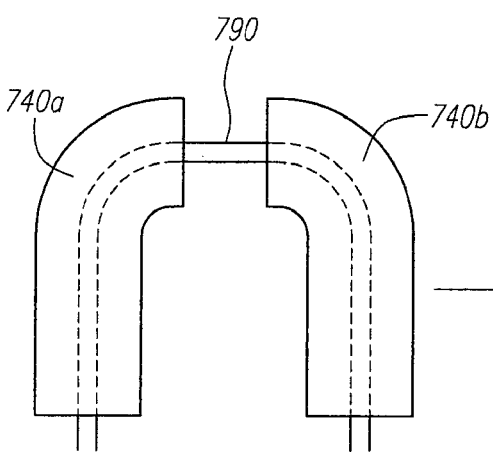
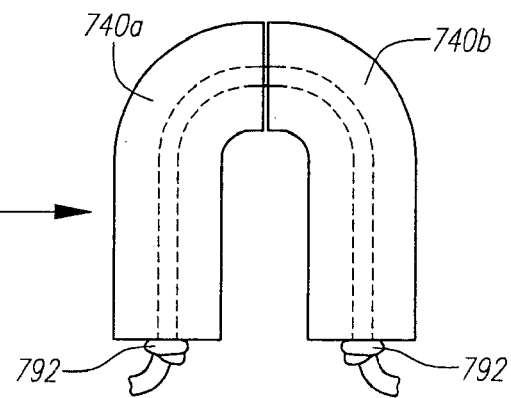
FIG. 38E　　　　　　FIG. 38F

PROSTHETIC INTERVERTEBRAL DISCS

RELATED APPLICATION DATA

This application is a continuation of U.S. application Ser. No. 11/281,205, filed on Nov. 15, 2005 and issued as U.S. Pat. No. 7,731,753 on Jun. 8, 2010, which, in turn, claims priority from U.S. Provisional Application Ser. No. 60/713,671, filed Sep. 1, 2005, which application is hereby incorporated by reference in its entirety as if fully set forth herein.

BACKGROUND OF THE INVENTION

The intervertebral disc is an anatomically and functionally complex joint. The intervertebral disc is composed of three component structures: (1) the nucleus pulposus; (2) the annulus fibrosus; and (3) the vertebral endplates. The biomedical composition and anatomical arrangements within these component structures are related to the biomechanical function of the disc.

The spinal disc may be displaced or damaged due to trauma or a disease process. If displacement or damage occurs, the nucleus pulposus may herniate and protrude into the vertebral canal or intervertebral foramen. Such deformation is known as herniated or slipped disc. A herniated or slipped disc may press upon the spinal nerve that exits the vertebral canal through the partially obstructed foramen, causing pain or paralysis in the area of its distribution.

To alleviate this condition, it may be necessary to surgically remove the involved disc and fuse the two adjacent vertebrae. In this procedure, a spacer is inserted in the place originally occupied by the disc and additional fixation devices, such as plates and rods, may be added to provide increased stability. Despite the excellent short-term results of such a "spinal fusion" for traumatic and degenerative spinal disorders, long-term studies have shown that alteration of the biomechanical environment leads to degenerative changes at adjacent mobile levels. The adjacent discs have increased motion and stress due to the increased stiffness of the fused segment. In the long term, this change in the mechanics of the motion of the spine causes these adjacent discs to degenerate.

To circumvent this problem, an artificial intervertebral disc replacement has been proposed as an alternative approach to spinal fusion. Although various types of artificial intervertebral discs have been developed to restore the normal kinematics and load-sharing properties of the natural intervertebral disc, they can be grouped into two categories: ball and socket joint type discs and elastomer type discs.

Artificial discs of ball and socket type are usually composed of metal plates, one to be attached to the upper vertebra and the other to be attached to the lower vertebra, and a polyethylene or metal bearing surface working as a ball. The metal plates may have concave areas to house the bearing surface. The ball and socket type allows free rotation or movement between the vertebrae between which the disc is installed and thus has no load sharing capability against bending and translation. (Some ball and socket type artificial discs have rotation limiting features, which still do not address appropriate torque for a natural disc.) Artificial discs of this type have a very high stiffness in the vertical direction; they cannot replicate the normal compressive stiffness of the natural disc. Also, the lack of load bearing capability in these types, of discs causes adjacent discs to bear the extra load, resulting in the eventual degeneration of the adjacent discs and facets. These types of discs also cannot replicate a natural disc's instantaneous access of rotation (IAR) as a direct result of lacking natural compressibility.

In elastomer type artificial discs, an elastomeric polymer is between metal plates and these metal plates are fixed to the upper and the lower vertebrae. The elastomeric polymer may be bonded to the metal plates by having the interface surface of the metal plates be rough and porous. This type of disc can absorb a shock in the vertical direction and has a load bearing capability. However, this structure has a problem in the interface between the elastomeric polymer and the metal plates. Even though the interface surfaces of the metal plates may be treated for better bonding, polymeric debris may nonetheless be generated after long term usage. Furthermore, the bond of the elastomer to the metal substrate tends to fail after a long usage because of its insufficient shear-fatigue strength.

Because of the above described disadvantages associated with either the ball and socket or elastomer type discs, there has existed a continued need for the development of new prosthetic devices. Several such new prosthetic devices are described in U.S. patent application Ser. No. 10/632,538, filed Aug. 1, 2003, and U.S. patent application Ser. No. 10/903,276, filed Jul. 30, 2004, each of which applications is hereby incorporated by reference herein. The foregoing applications describe, inter alia, prosthetic intervertebral discs that include an upper endplate, a lower endplate, and a compressible core member disposed between the two endplates. Several prosthetic disc embodiments are described, including single-piece, two-piece, three-piece, and four-piece structures.

While such prosthetic intervertebral discs and methods for their use show great promise, there remains a need for improved prosthetic discs and methods for their use.

Relevant Literature

U.S. Pat. Nos. 3,867,728; 4,911,718; 5,039,549; 5,171,281; 5,221,431; 5,221,432; 5,370,697; 5,545,229; 5,674,296; 6,162,252; 6,264,695; 6,533,818; 6,582,466; 6,582,468; 6,626,943; 6,645,248. Also of interest are published United States Patent Application Nos. 2002/0107575, 2003/0040800, 2003/0045939, and 2003/0045940. See also Masahikio Takahata, Uasuo Shikinami, Akio Minami, "Bone Ingrowth Fixation of Artificial Intervertebral Disc Consisting of Bioceramic-Coated Three-dimensional Fabric," SPINE, Vol. 28, No. 7, pp. 637-44 (2003).

SUMMARY OF THE INVENTION

Prosthetic intervertebral discs and methods for using such discs are provided. The subject prosthetic discs typically include an upper endplate, a lower endplate, and a compressible core member disposed between the two endplates.

In several embodiments, the subject prosthetic discs are characterized by including top and bottom endplates separated by a compressible element. The two plates are held together by at least one fiber wound around at least one region of the top endplate and at least one region of the bottom endplate. The fibers are generally high tensile strength fibers with a high modulus of elasticity and high wear resistance. The elastic properties of the fibers, as well as factors such as the number of fibers used, the thickness of the fibers, the number of layers of fiber windings, the tension applied to each layer, and the crossing pattern of the fiber windings enable the prosthetic disc structure to mimic the functional characteristics and biomechanics of a normal-functioning, natural disc. Alternatively, the two plates are held together by an engagement mechanism connecting each plate to the compressible element. The subject discs may be employed with separate vertebral body fixation elements, or they may include integrated vertebral body fixation elements.

Several optional core materials and structures may be incorporated in each of the prosthetic disc embodiments described herein. For example, the core member may be formed of an appropriately stiff material, such as polyurethane or silicone, and is typically fabricated by injection or compression molding. In other examples, the core member may be formed by layers of fabric woven from fibers. In still further examples, the core member may comprise a combination of these materials, such as a fiber-reinforced polyurethane or silicone. As an additional option, one or more spring members may be placed between the upper and lower endplates in combination with the core member, such as in a coaxial relationship in which the core member has a generally cylindrical or toroidal shape and a spring is located at its center.

In other embodiments, the core structure comprises two or more core members having different load bearing properties and having the ability to vary the center of rotation of the core structure. The varying properties of the core members may be provided by selection of materials, construction, or other features. In still further embodiments, the core structure comprises one or more core members that are formed of materials or are otherwise constructed to provide varying stiffness or other material properties to accommodate different loads or loading configurations. Examples of these core structures include cores having discrete portions formed of different materials, cores having grooves or other features formed on portions of the core member for other purposes (such as sterilization), and cores having coils or couplers attached to or formed integrally with the core member.

In still further embodiments, the core structure is provided with one or more mechanisms adapted to adjust the size, shape, orientation, or other feature or combination of features of the core member. For example, the core member may include threads, slots and tabs, or other mechanisms that provide the ability to adjust the height of the core, or to adjust other properties of the core.

Several particularly preferred core structures include a hollow member that is adapted to be inflated after implantation of the prosthetic disc. In this way, the prosthetic disc is provided with a contracted condition (core uninflated) for delivery and implantation of the disc, and an expanded condition (core inflated) that is adapted for use by the patient after implantation. These core structures may be provided with a fluid port that is adapted to facilitate inflation of the core. Alternatively, a fluid communication lumen may be provided that extends from the hollow core member and provides a lumen through which inflation media may be injected into the core. The hollow core may be provided with two or more compartments, each of which may be independent, or which may be in fluid communication with one another.

Several optional endplates and related mechanisms may be incorporated in each of the prosthetic disc embodiments described herein. For example, the endplates may be curved or kidney bean shaped to facilitate rotation of the disc within the intervertebral void space. Alternatively, the endplates may be of a partially cylindrical shape adapted to engage and retain a substantially cylindrical core member.

Other and additional devices, apparatus, structures, and methods are described by reference to the drawings and detailed descriptions below.

BRIEF DESCRIPTIONS OF THE FIGURES

The Figures contained herein are not necessarily drawn to scale, with some components and features being exaggerated for clarity.

Figure 1B:
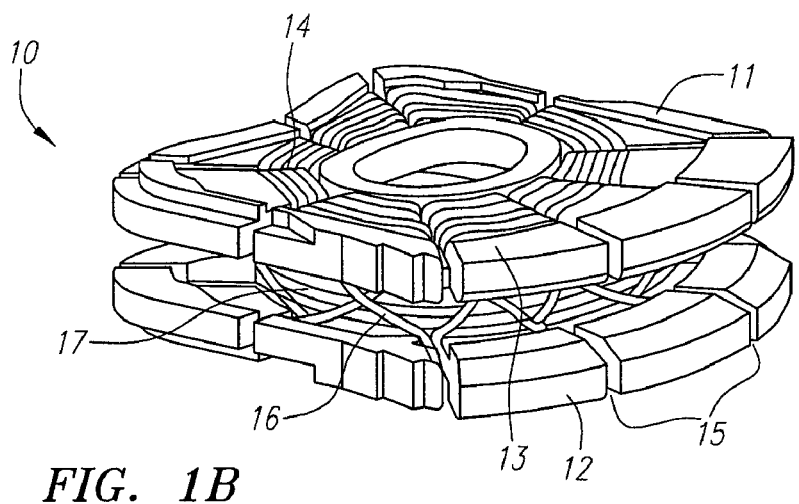

FIGS. 1A and 1B provide a three dimensional view of two different prosthetic discs according to the subject invention.

Figure 2:
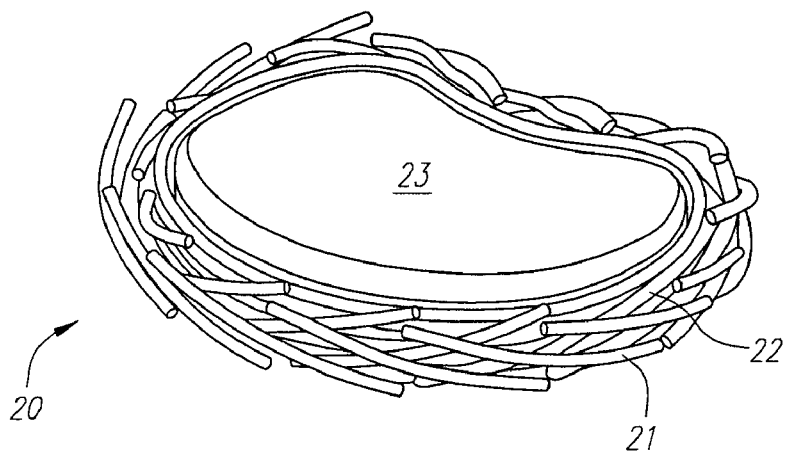

FIG. 2 provides a three-dimensional view of a fibrous compressible element that includes a polymeric nucleus and a fibrous annulus according to one embodiment of the subject invention.

Figure 3:
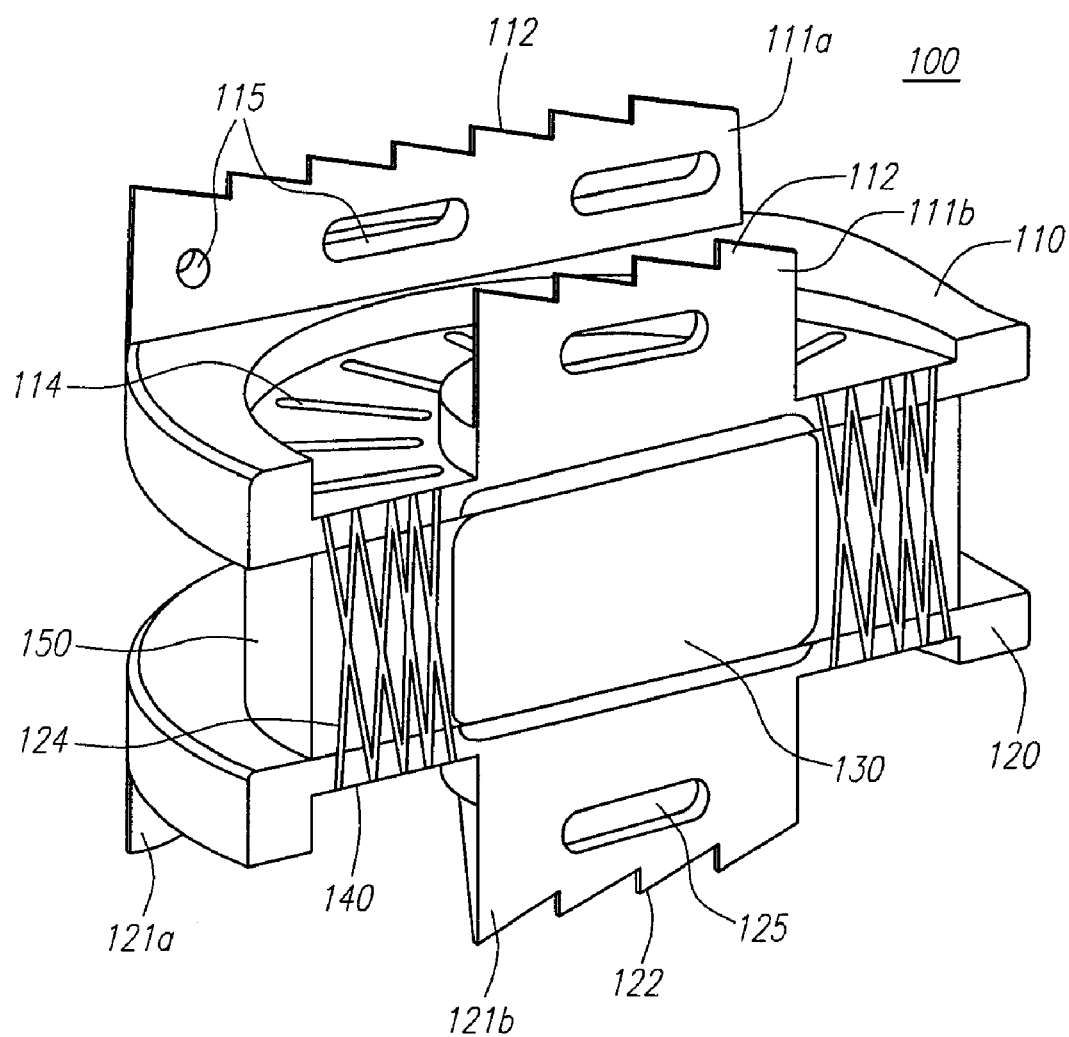

FIG. 3 provides a three-dimensional cross-sectional view of a prosthetic disc.

Figure 4A:
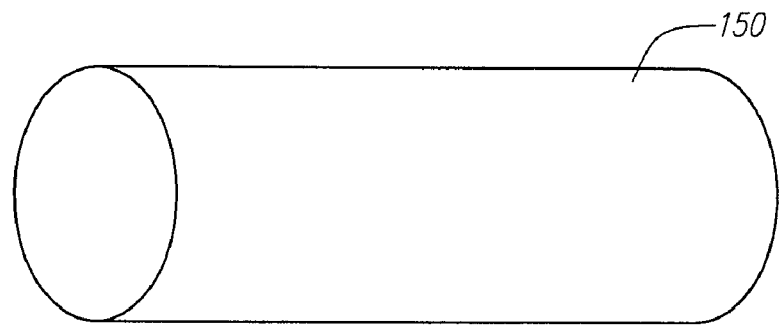
Figure 4B:
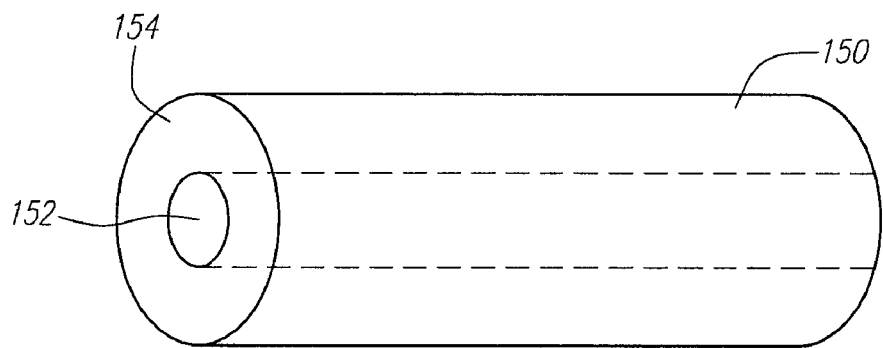

FIGS. 4A-B provide three-dimensional views of two embodiments of a core member.

Figure 4C:
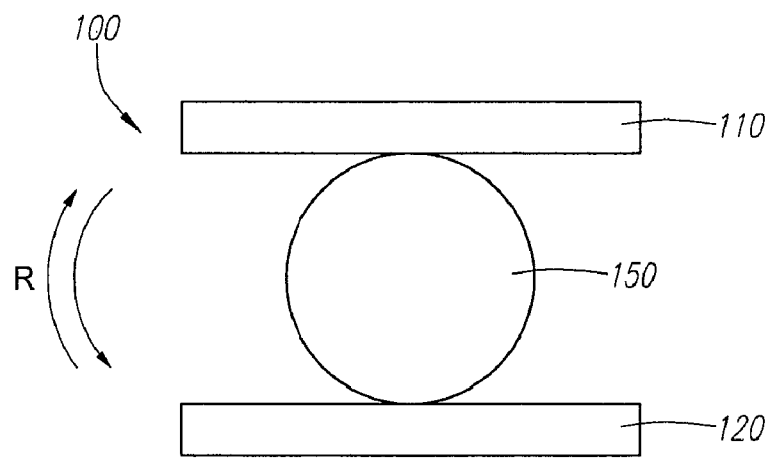

FIG. 4C provides an end view of a core member located between a pair of endplates.

Figure 5A:
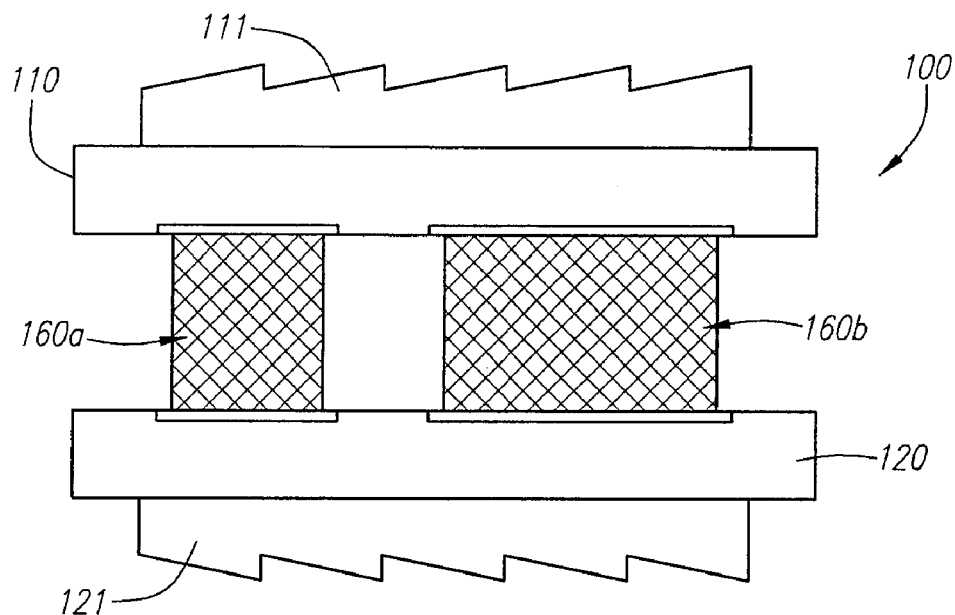
Figure 5B:
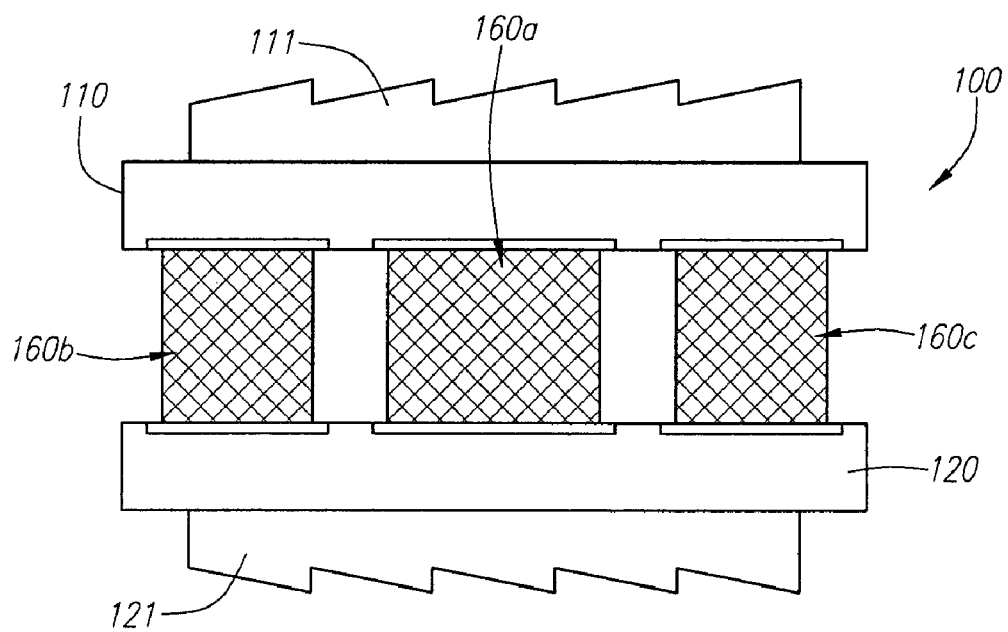

FIGS. 5A-B provide side views of prosthetic discs having cores formed of a plurality of core members.

FIGS. 6A-6N and 6P-6T provide illustrations of several embodiments of core members suitable for use in prosthetic discs described herein.

FIGS. 7-10 provide illustrations of several embodiments of adjustable core structures.

Figure 11:
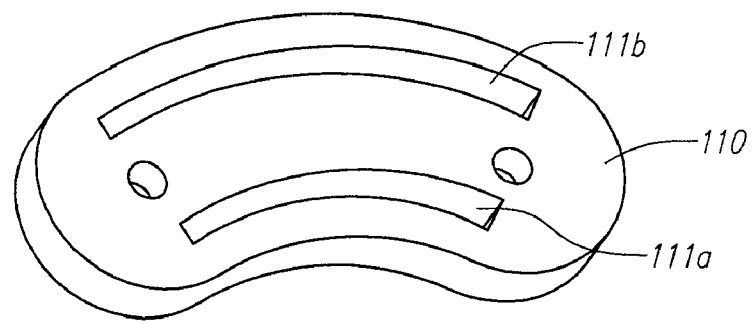

FIG. 11 provides a top view of an endplate.

Figure 12A:
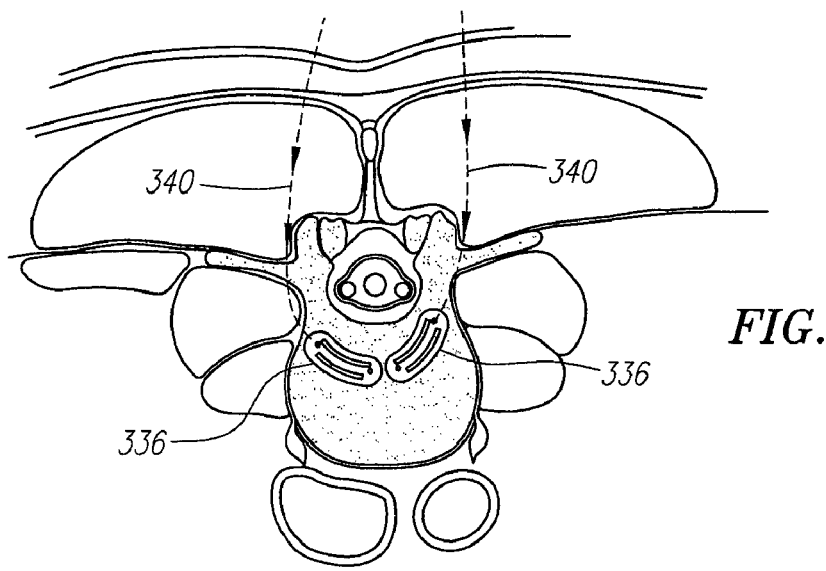
Figure 12B:
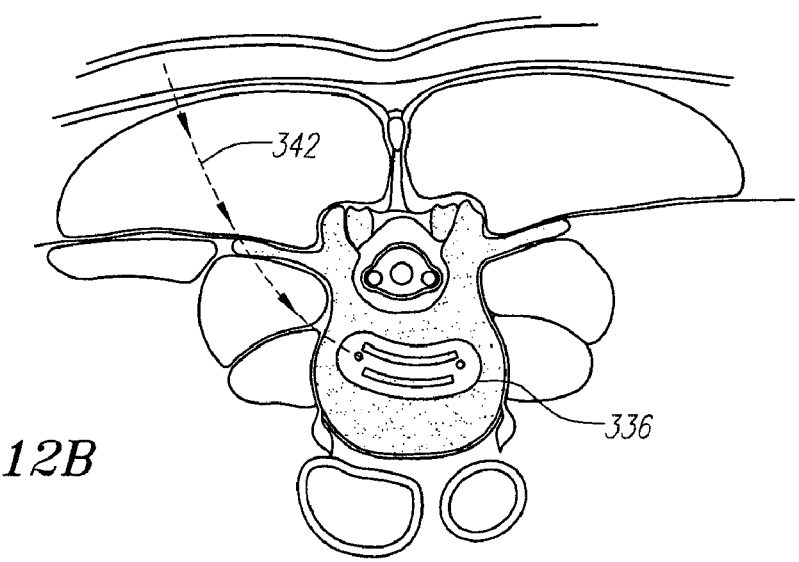

FIGS. 12A-B provide illustrations of implantation methods for prosthetic discs having endplates such as that shown in FIG. 11.

FIG. 13 provides a perspective view of a prosthetic disc having a generally elongated tubular core member.

FIGS. 14A-D provide illustrations of a selectably expandable prosthetic disc and its components.

Figure 15A:
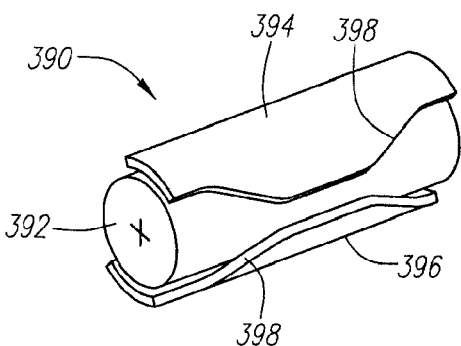
Figure 15B:
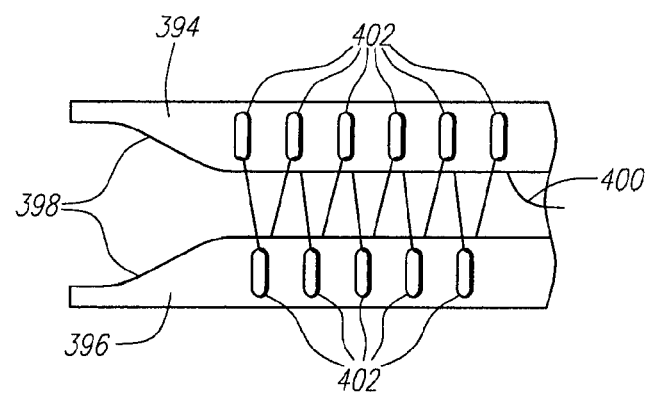

FIGS. 15A-B provide illustrations of a prosthetic disc having an elongated tubular core member.

FIGS. 16A-C, 17A-B, 18A-C, and 19A-C provide illustrations of prosthetic discs that are constructed to mimic the physiology of the natural functional spinal unit.

Figure 20:
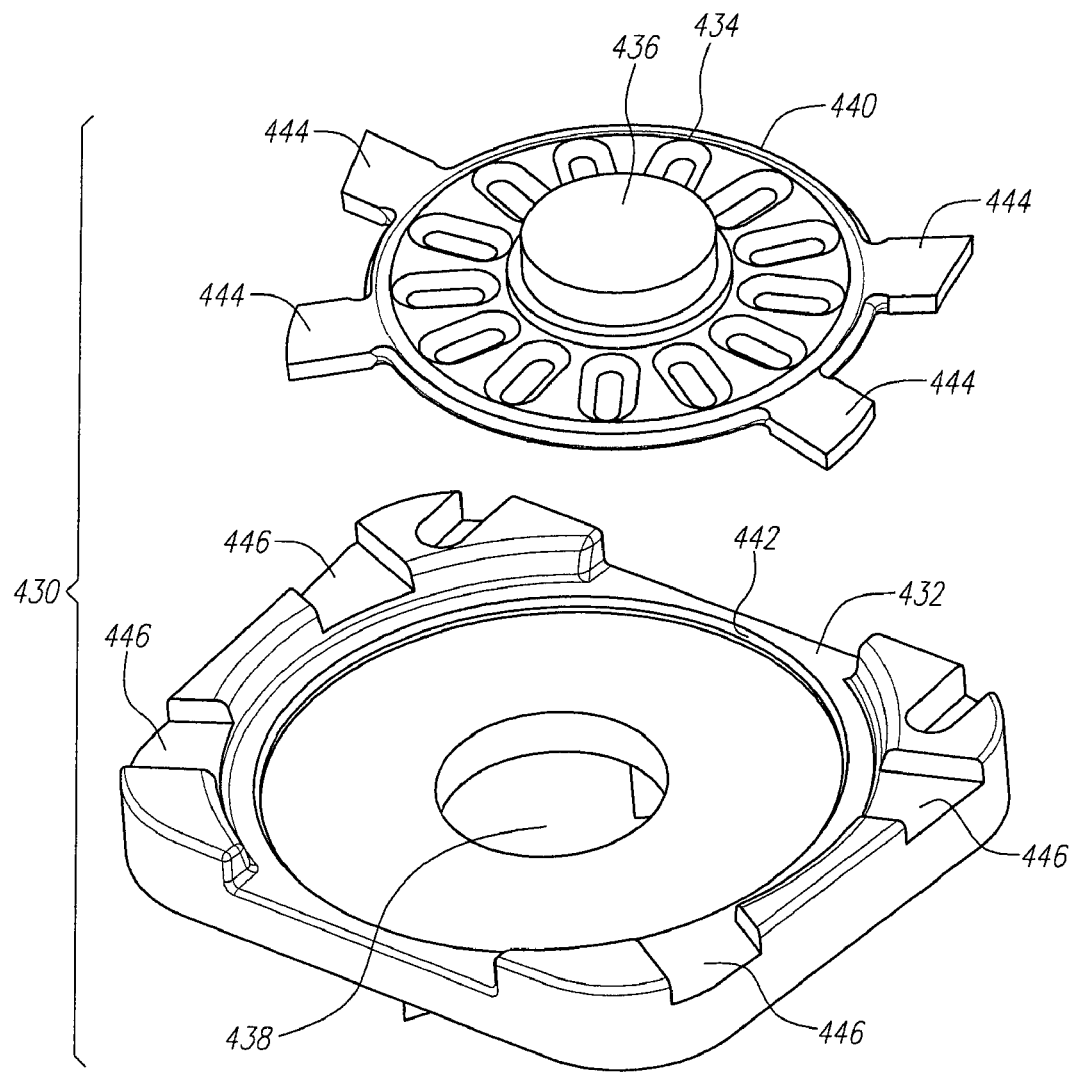
Figure 21A:
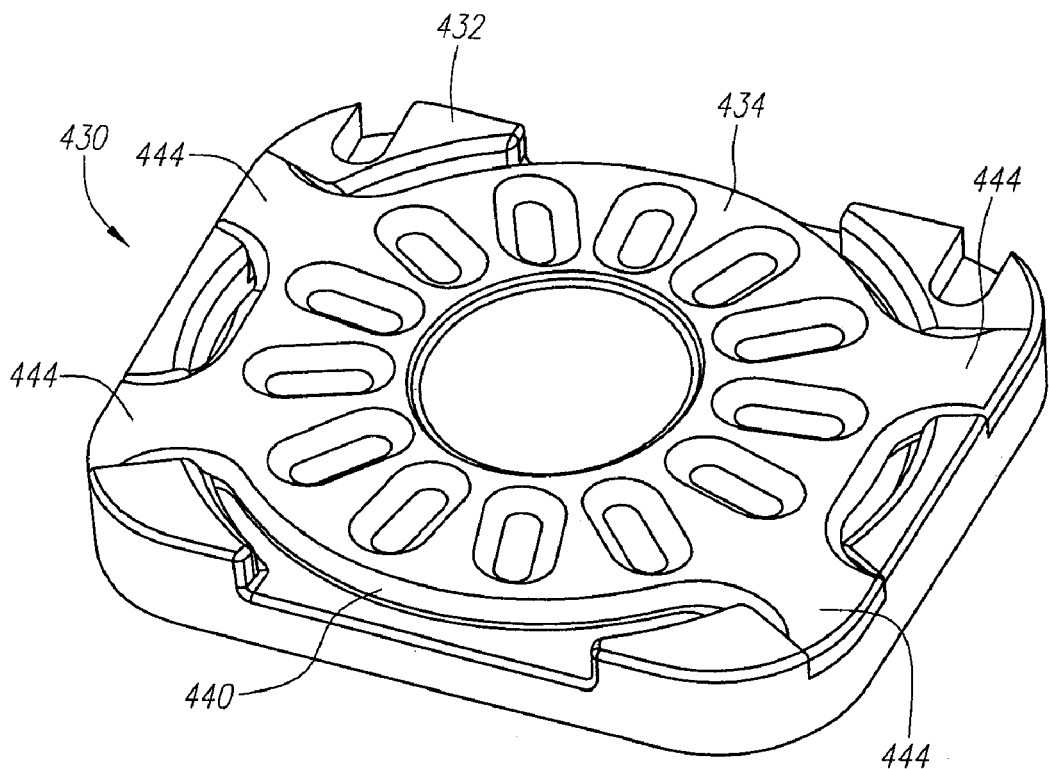
Figure 21B:
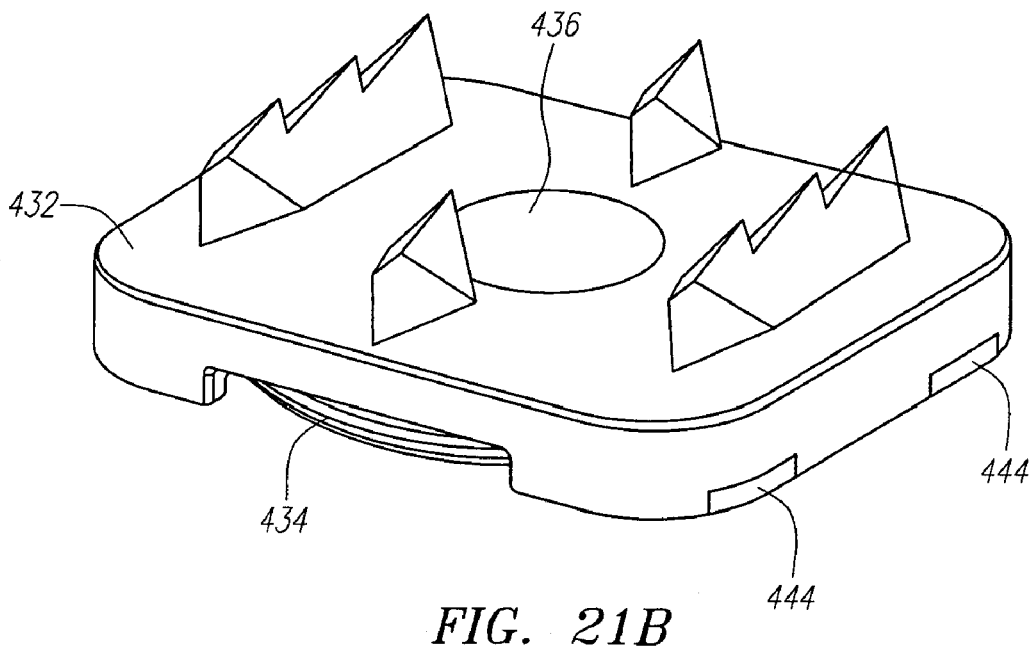

FIGS. 20 and 21A-B provide illustrations of two-piece endplates including inner endplates and outer endplates.

FIGS. 22A-D provide illustrations of a prosthetic disc having a plurality of fixed anchoring fins on its outer surface.

Figure 23A:
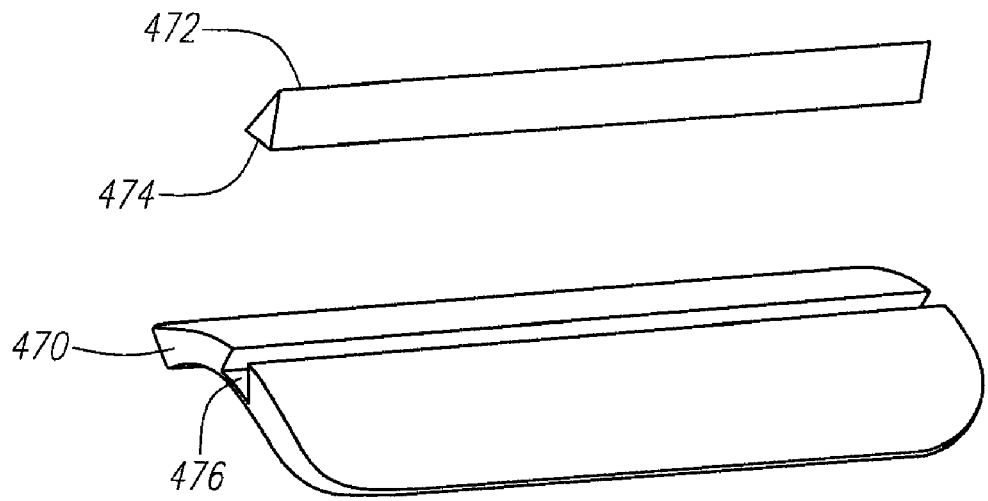
Figure 23B:
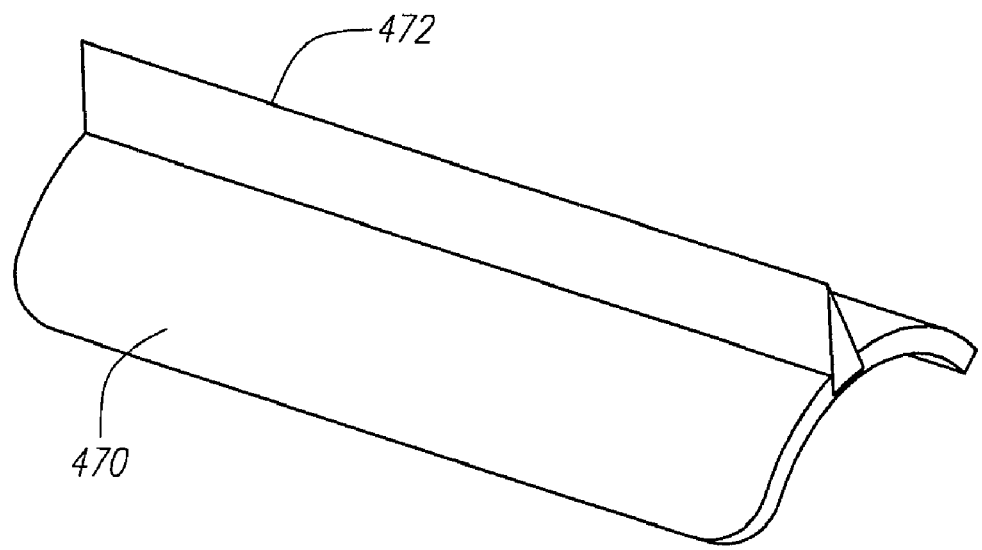

FIGS. 23A-B provide illustrations of a partially cylindrical endplate and a removable keel.

FIGS. 24A-B and 25A-C provide illustrations of selectively deployable fixation screws and associated mechanisms.

Figure 26A:
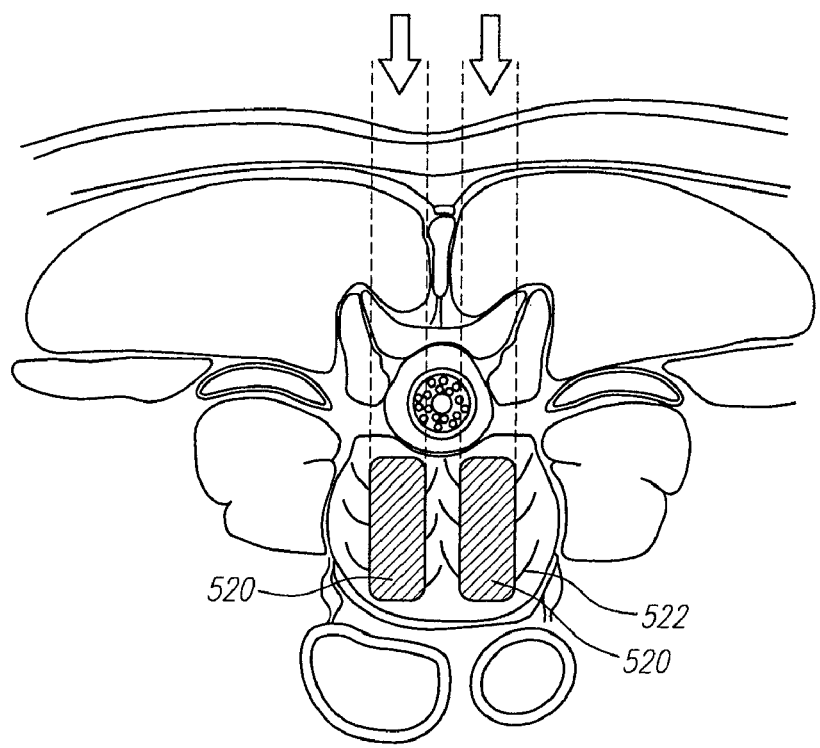
Figure 26B:
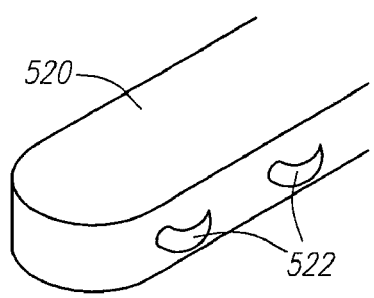
Figure 26C:
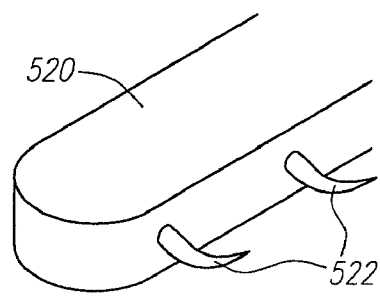

FIGS. 26A-C provide illustrations of another prosthetic disc fixation mechanism.

Figure 27A:
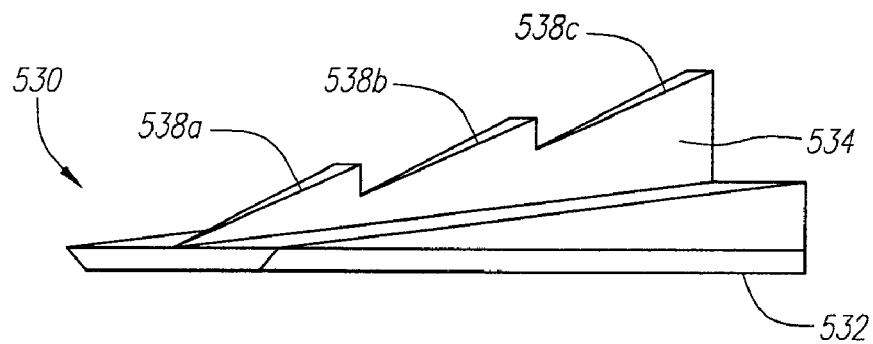
Figure 27B:
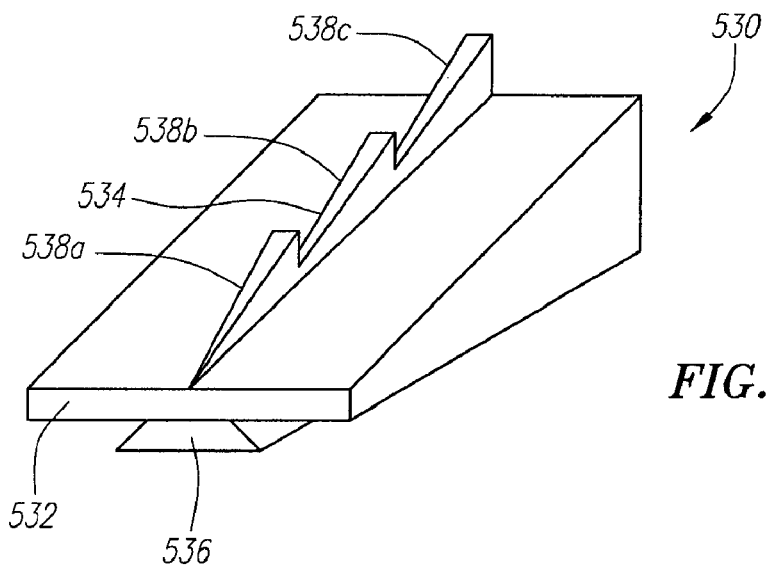
Figure 27C:
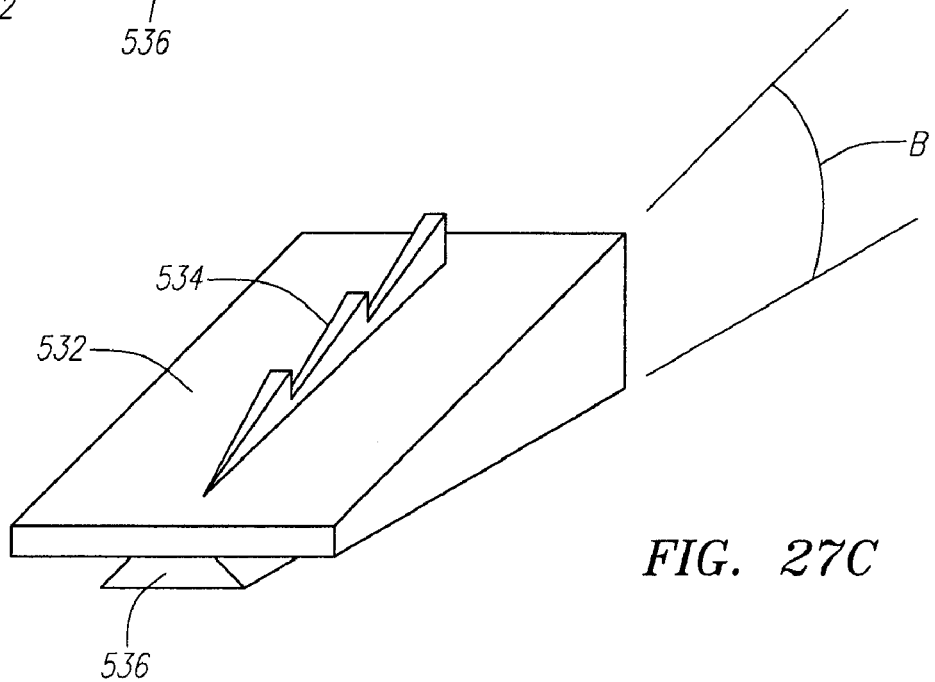

FIGS. 27A-C provide illustrations of an insertable keel structure.

Figure 28:
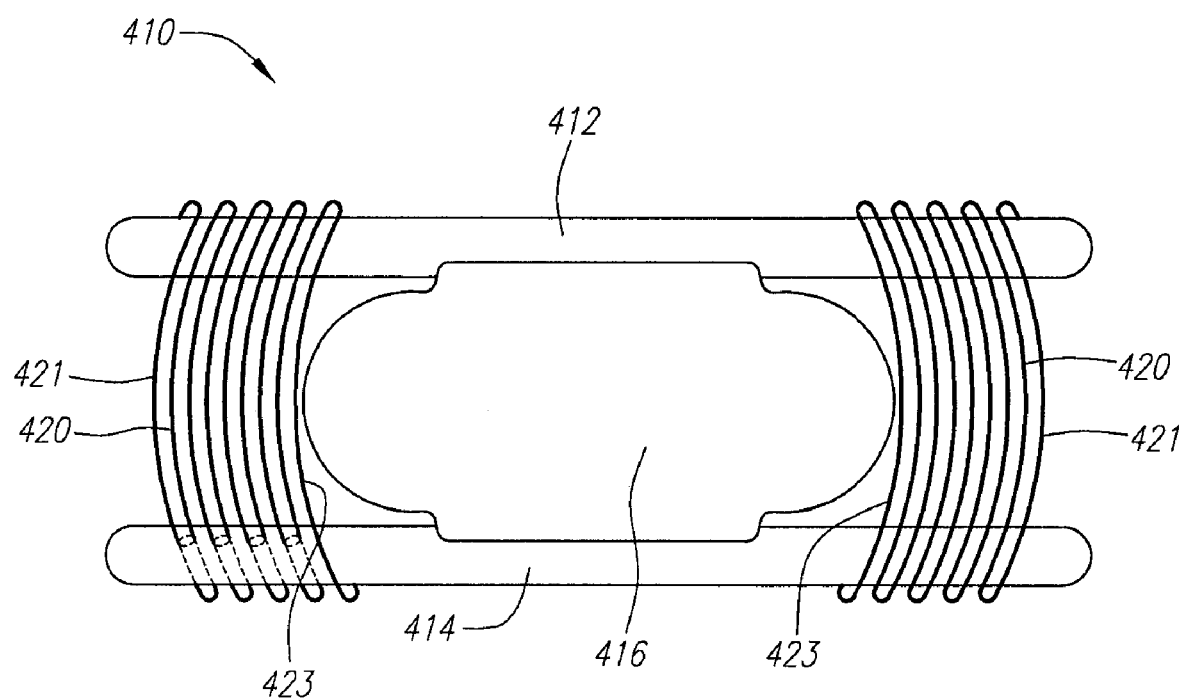

FIG. 28 provides an illustration of a fiber winding construction for attaching upper and lower endplates of a prosthetic disc.

Figure 29A:
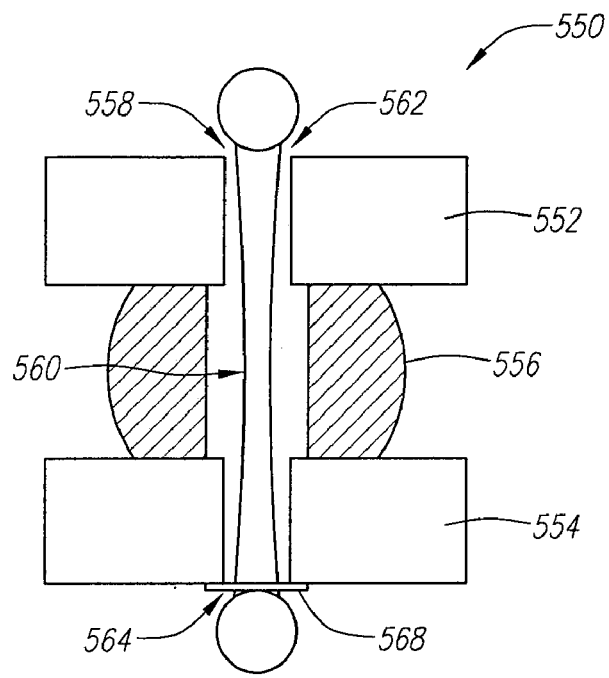
Figure 29B:
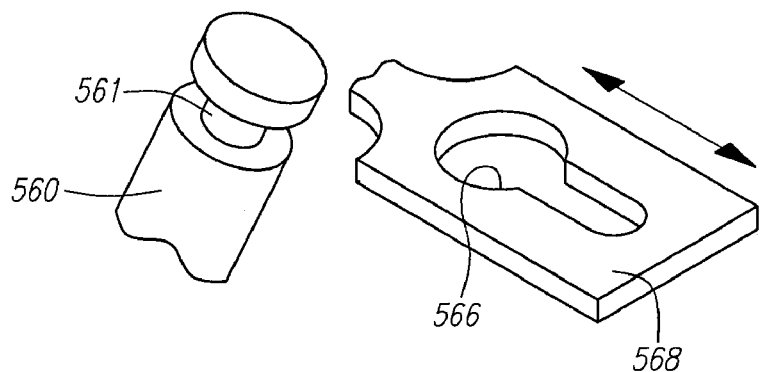

FIGS. 29A-B provide illustrations of a system for maintaining a prosthetic disc in a low profile condition during an implantation procedure.

Figure 30:
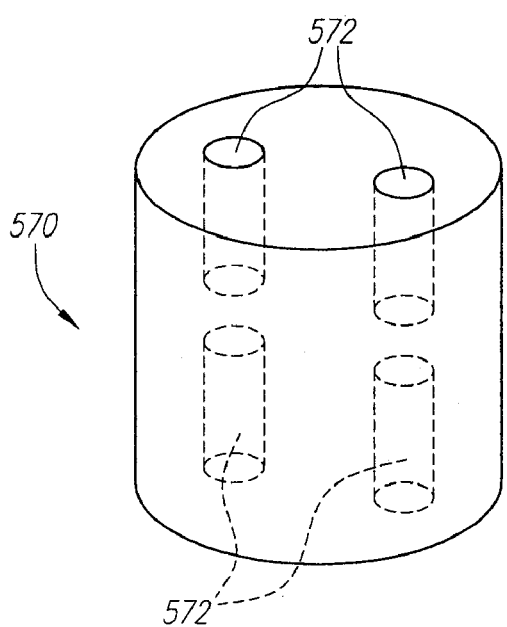

FIG. 30 provides an illustration of a core structure adapted for use in a prosthetic disc.

FIGS. 31A-D provide illustrations of spinal motion preservation systems.

FIGS. 32A-B provide illustrations of disc interlocking mechanisms.

FIGS. 33A-C provide illustrations of prosthetic discs adapted to be deployed in an approximately X-shaped configuration.

Figure 34A:
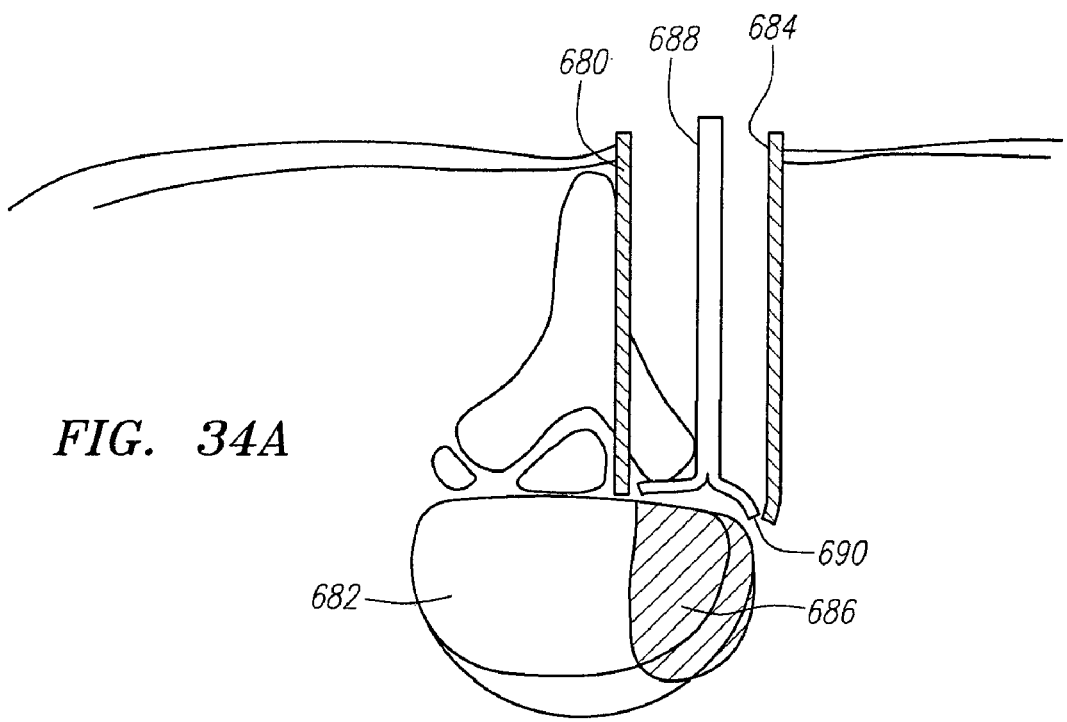
Figure 34B:
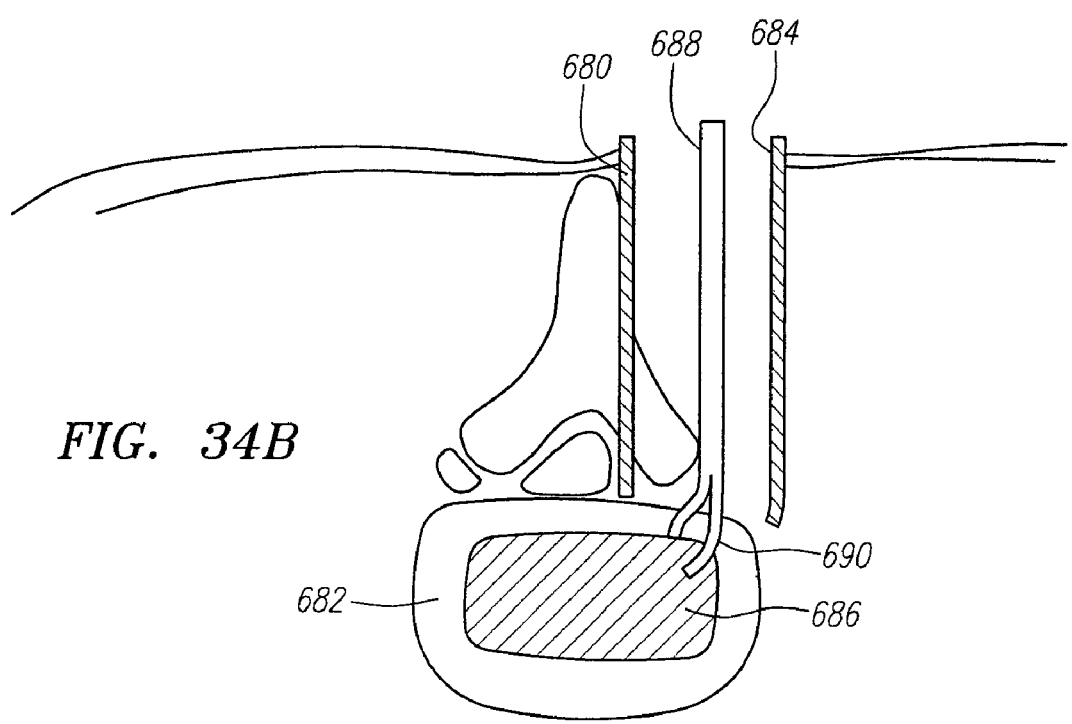

FIGS. 34A-B provide illustrations showing a surgical method for implanting a prosthetic disc.

FIGS. 35A-D provide illustrations showing another surgical method for implanting a prosthetic disc.

FIGS. 36A-I provide illustrations of mechanisms for attaching a pair of adjacent prosthetic discs.

FIGS. 37A-F provide illustrations showing another surgical method for implanting a prosthetic disc.

FIGS. 38A-F provide illustrations of several embodiments of generally "J"-shaped prosthetic discs.

Figure 39:
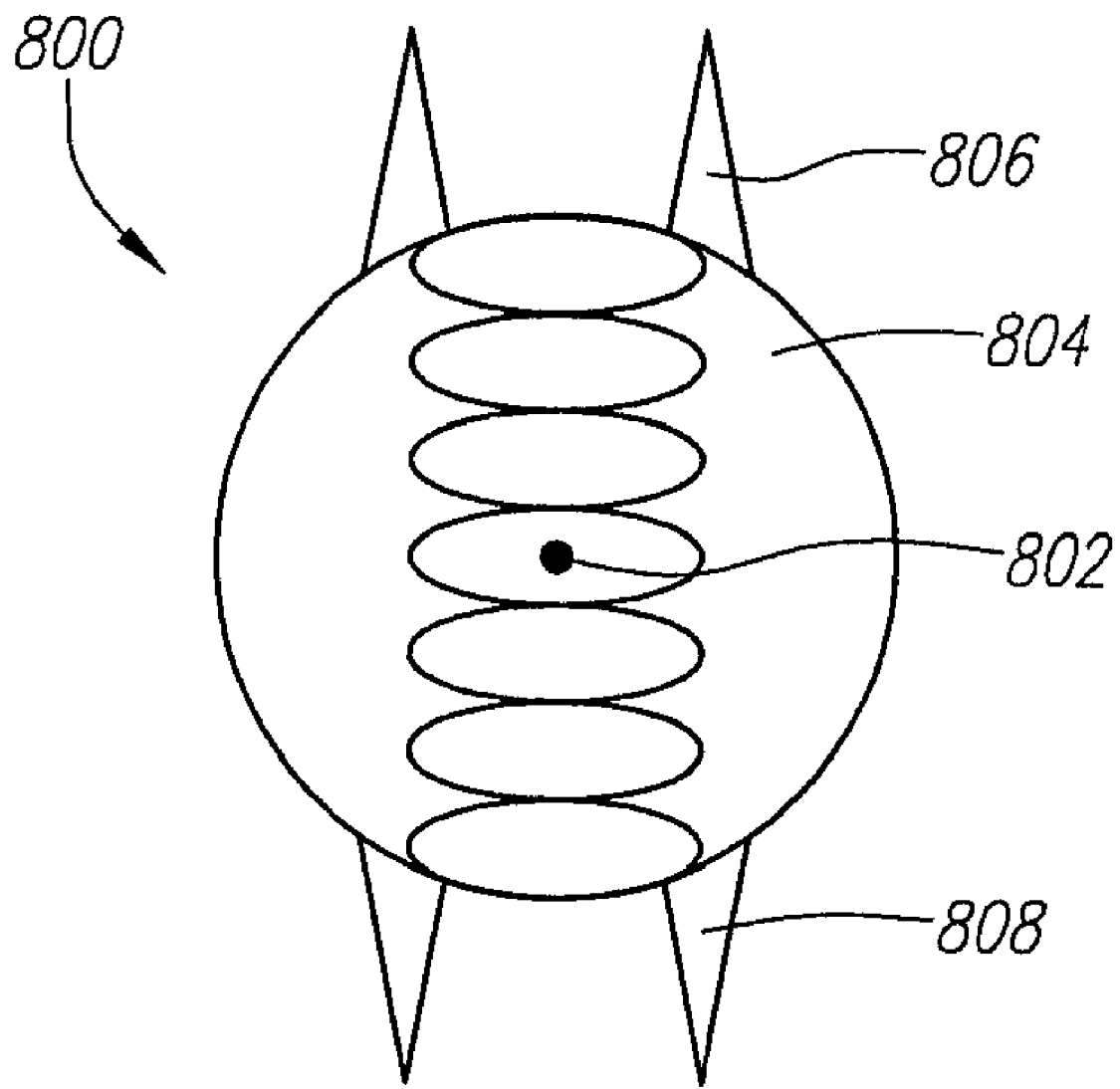

FIG. 39 provides an illustration of an encapsulated spring disc replacement system.

DESCRIPTIONS OF THE PREFERRED EMBODIMENTS

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to at least the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present inventions.

I. Overview of the Described Prosthetic Intervertebral Discs

Prosthetic intervertebral discs, methods of using such discs, apparatus for implanting such discs, and methods for implanting such discs are described herein. It is to be understood that the prosthetic intervertebral discs, implantation apparatus, and methods are not limited to the particular embodiments described, as these may, of course, vary. It is also to be understood that the terminology used herein is for the purpose of describing particular embodiments only, and is not intended to be limiting, since the scope of the present inventions will be limited only by the appended claims.

The prosthetic intervertebral discs are preferably artificial or manmade devices that are configured or shaped so that they can be employed as replacements for an intervertebral disc in the spine of a vertebrate organism, e.g., a mammal, such as a human. The subject prosthetic intervertebral discs have dimensions that permit them to substantially occupy the space between two adjacent vertebral bodies that is present when the naturally occurring disc between the two adjacent bodies is removed, i.e., a disc void space. By substantially occupy is meant that the prosthetic disc occupies a sufficient volume in the space between two adjacent vertebral bodies that the disc is able to perform some or all of the functions performed by the natural disc for which it serves as a replacement. In certain embodiments, subject prosthetic discs may have a roughly bean shaped structure analogous to naturally occurring intervertebral body discs. In many embodiments, the length of the prosthetic discs range from about 5 mm to about 40 mm, preferably from about 10 mm to about 25 mm, the width of the prosthetic discs range from about 2 mm to about 50 mm, preferably from about 10 mm to about 35 mm, and the height of the prosthetic discs range from about 2 mm to about 15 mm, preferably from about 5 mm to about 12 mm.

The subject discs are characterized in that they typically include both an upper (or top) and lower (or bottom) endplate or bone interfacing structure (e.g., contiguous plates, interrupted plates, spikes, keels, porous surfaces, and the like), where the upper and lower endplates are separated from each other by a compressible element, where the combination structure of the endplates and compressible element provides a prosthetic disc that functionally closely mimics real disc. A feature of some of the subject prosthetic discs is that the top and bottom endplates are held together by at least one fiber, e.g., of the fibrous compressible element, wound around at least one portion of each of the top and bottom endplates. As such, in these embodiments, the two endplates (or substrates) are held to each other by one or more fibers that are wrapped around at least one domain/portion/area of the upper endplate and lower endplate such that the plates are joined to each other.

Also provided are methods of using the subject prosthetic intervertebral discs. The subject prosthetic intervertebral discs find use in the replacement of damaged or dysfunctional intervertebral discs in vertebrate organisms. Generally the vertebrate organisms are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In many embodiments, the subjects will be humans.

In general, the devices are employed by first removing part or all of the native disc to be replaced from the subject or patient according to typical surgical technique to produce a disc void space. Next, the subject prosthetic disc is implanted or positioned in the disc void space, resulting in replacement of the removed disc with the prosthetic disc. This implantation step may include a vertebral body fixation element implantation substep, a post implantation vertebral body securing step, or other variations, depending on the particular configuration of the prosthetic device being employed. In addition, the implantation step described above may include use of one or more implantation devices (or disc delivery devices) for implanting the system components to the site of implantation.

Two different representative intervertebral discs are shown in FIGS. 1A and 1B. These discs, and others, are also described more fully in U.S. patent application Ser. No.

10/632,538, filed Aug. 1, 2003, ("the '538 application"), and U.S. patent application Ser. No. 10/903,276, filed Jul. 30, 2004, ("the '276 application"), each of which applications is incorporated by reference herein. A substantial portion of this overview description, including FIGS. 1A-B, 2, and 3, is adapted from portions of the '276 application.

As can be seen in FIGS. 1A and 1B, prosthetic discs 10 each include a top endplate 11 and a lower endplate 12. Top and bottom endplates 11 and 12 are substantially planar substrates, where these plates typically have a length from about 5 mm to about 40 mm, such as from about 10 mm to about 25 mm, a width of from about 2 mm to about 50 mm, such as from about 10 mm to about 35 mm and a thickness of from about 0.25 mm to about 6 mm, such as from about 1 mm to about 4 mm. The top and bottom endplates or equivalent are fabricated from a biocompatible material that also provides for the requisite mechanical properties, where representative materials from which the endplates may be fabricated are known to those of skill in the art and include, but are not limited to: titanium, titanium alloys, stainless steel, cobalt/chromium/molybdenum alloys, multiphase alloys such as MP-35N, etc.; plastics such as polyethylene with ultra high molar mass (molecular weight) (UHMWPE), polyether ether ketone (PEEK), etc.; ceramics; graphite; etc. As shown in FIGS. 1A and 1B, separating the top and bottom endplates is a compressible element 17. The thickness of the compressible element may vary, but ranges in many embodiments from about 1 mm to about 15 mm, including from about 2 mm to about 10 mm.

The disc is further characterized in that it includes an annular region 13 (i.e., annulus), which is the region, domain or area that extends around the periphery of the disc, and a nuclear region (i.e., nucleus) 14, which is the region, domain or area in the center of the disc and surrounded by the annulus.

As shown in FIGS. 1A and 1B, the plates include a single region around which a fiber is wound in order to hold the plates together, although in many embodiments the plates have a plurality of such regions. As shown in FIGS. 1A and 1B, endplates 11 and 12 include a plurality of slots 15 through which fibers, e.g., of the fibrous compressible element, may be passed through or wound, as shown. In many embodiments, the number of different slots present in the periphery of the device ranges from about 4 to about 36, such as from about 5 to about 25. As shown in FIGS. 1A and 1B, at least one fiber 16 forming part of the compressible element is wrapped around a region of the top and bottom plates, e.g., by being passed through slots in the top and bottom plates, in order to hold the plates together.

The compressible elements, 17, are typically made up of one or more fibers, where the fibers are generally high tenacity fibers with a high modulus of elasticity and high wear resistance. By high tenacity fibers is meant fibers that can withstand a longitudinal stress without tearing asunder of at least about 50 MPa, such as at least about 250 MPa. As the fibers have a high modulus of elasticity, their modulus of elasticity is typically at least about 100 MPa, usually at least about 500 MPa. The fibers are generally elongate fibers having a diameter that ranges from about 0.1 mm to about 5 mm, such as about 0.2 mm to about 2 mm, where the length of each individual fiber making up the fibrous component may range from about 0.1 m to about 20 m, such as from about 0.3 m to about 3 m.

The fibers making up the fibrous compressible elements may be fabricated from any suitable material, where representative materials of interest include, but are not limited to: metals, including alloys, polymers, including polyester (e.g., Dacron), polyethylene, polyaramid, polytetrafluoroethylene, carbon or glass fibers, polyethylene terephthalate, arcrylic polymers, methacrylic polymers, polyurethane, polyurea, polyolefin, halogenated polyolefin, polysaccharide, vinylic polymer, polyphosphazene, polysiloxane, nylon, and the like.

The fibrous compressible elements made up of one or more fibers wound around one or more regions of the top or bottom plates may make up a variety of different configurations. For example, the fibers may be wound in a pattern that has an oblique orientation to simulate the annulus of intact disc, where a representative oblique fiber configuration or orientation is shown in FIG. 1A. The number of layers of fiber winding may be varied to achieve similar mechanical properties to an intact disk. Where desired, compliancy of the structure may be reduced by including a horizontal winding configuration, as shown in FIG. 1B.

In certain embodiments, the fibrous compressible element 20 has a fibrous component 21 limited to the annular region of the disc 22, e.g., to the region along the periphery of the disc. FIG. 2 provides a representation of this embodiment, where the fibrous component is limited solely to the annular region of the disc and includes both oblique and horizontal windings. Also shown is a separate polymeric component 23 present in the nucleus. The fiber windings of the various layers of fiber may be at varying angles from each other where the particular angle for each layer may be selected to provide a configuration that best mimics the natural disc. Additionally, the tension placed on the fibers of each layer may be the same or varied.

In yet other embodiments the fibrous component of the fibrous compressible element may extend beyond the annular region of the disc into at least about a portion, if not all, of the nucleus.

In certain embodiments, the fibrous compressible element further includes one or more polymeric components. The polymeric component(s), when present, may be fabricated from a variety of different physiologically acceptable materials. Representative materials of interest include, but are not limited to: elastomeric materials, such as polydimethylsiloxane, polycarbonate-polyurethane, aromatic and aliphatic polyurethanes, poly(ethylene propylene) copolymer, polyvinylchloride, poly(tetrafluoro ethylene) and copolymers, hydrogels, and the like.

The polymeric component may be limited to particular domains, e.g., the annular and/or nucleus domains, or extend throughout the entire region of the fibrous compressible elements positioned between the two endplates. As such, in certain embodiments the polymeric component is one that is limited to the nuclear region of the disc, as shown in FIG. 2. In FIG. 2, fibrous compressible element 20 includes a distinct fibrous component 21 that is located in the annular region of the disc 22, while polymeric component 23 is located in the nuclear region of the disc. In other embodiments, the polymeric component is located in both the annular and nuclear regions. In yet other embodiments, the polymeric component may be located solely in the annular region.

Depending on the desired configuration and mechanical properties, the polymeric component may be integrated with the fibrous component, such that at least a portion of the fibers of the fibrous component is embedded in, e.g., complexed with, at least a portion of the polymeric component. In other words, at least a portion of the fibrous component is impregnated with at least a portion of the polymeric component. For example, stacked two-dimensional layers of the fibrous component may be present inside the polymeric component, such that the fibrous component is impregnated with the polymeric component.

In those configurations where the fibrous and polymeric components are present in a combined format, the fibers of the fibrous component may be treated to provide for improved bonding with the polymeric component. Representative fiber treatments of interest include, but are not limited to: corona discharge, O2 plasma treatment, oxidation by strong acid (HNO3, H2SO4). In addition, surface coupling agents may be employed, and/or a monomer mixture of the polymer may be polymerized in presence of the surface-modified fiber to produce the composite fiber/polymeric structure. Additionally, the fiber may be of a composite construction with an outer layer composed of a material optimized for surface coupling. The composite structure can also be composed of an outer jacket that provides bonding to the polymeric component but allows the relative motion of the fibrous component within the jacket.

As indicated above, the devices may include one or more different polymeric components. In those embodiments where two or more different polymeric components are present, any two given polymeric components are considered different if they differ from each other in terms of at least one aspect, e.g., composition, cross-linking density, and the like. As such, the two or more different polymeric components may be fabricated from the same polymeric molecules, but differ from each other in terms of one or more of: cross-linking density; fillers; etc. For example, the same polymeric material may be present in both the annulus and nucleus of the disc, but the crosslink density of the annulus polymeric component may be higher than that of the nuclear region. In yet other embodiments, polymeric materials that differ from each other with respect to the polymeric molecules from which they are made may be employed.

By selecting particular fibrous component and polymeric component materials and configurations. e.g., from the different representative formats described above, a disc with desired functional characteristics, e.g., that mimics the functional characteristics of the naturally occurring disc, may be produced.

Representative particular combinations of interest include, but are not limited to, the following:
1. Biocompatible polyurethane, such as Ethicon Biomer, reinforced with Dacron poly(ethylene terephthalate) fiber, or Spectra polyethylene fiber, or Kevlar polyaramide fiber, or carbon fiber.
2. Biocompatible polysiloxane modified styrene-ethylene butylene block copolymer sold under C-Flex tradename reinforced with Dacron poly(ethylene terephthalate) fiber, or Spectra polyethylene fiber, or Kevlar polyaramide fiber, or carbon fiber.
3. Biocompatible Silastic silicone rubber, reinforced with Dacron poly(ethylene terephthalate) fiber, or Spectra polyethylene fiber, or Kevlar polyaramide fiber, or carbon fiber.

In using the subject discs, the prosthetic disc is fixed to the vertebral bodies between which it is placed. More specifically, the upper and lower plates of the subject discs are fixed to the vertebral body to which they are adjacent. As such, the subject discs are employed with vertebral body fixation elements during use. In certain embodiments, the vertebral body fixation elements are integral to the disc structure, while in other embodiments the vertebral body fixation elements are separate from the disc structure.

Another representative prosthetic intervertebral disc 100 is shown in FIG. 3, and is also described more fully in the '276 application. The prosthetic disc 100 has an integrated structure that includes an upper endplate 110, a lower endplate 120, and a core member 130 retained between the upper endplate 110 and the lower endplate 120. One or more fibers 140 are wound around the upper and lower endplates to attach the endplates to one another. The wind of the fibers 140 allows a degree of axial rotation, bending, flexion, and extension by and between the endplates. The core member 130 may be provided in an uncompressed or a pre-compressed state. An annular capsule 150 is optionally provided in the space between the upper and lower endplates, surrounding the core member 130 and the fibers 140. The upper endplate 110 and lower endplate 120 are generally flat, planar members, and are fabricated from a biocompatible material that provides substantial rigidity. Examples of materials suitable for use in fabricating the upper endplate 110 and lower endplate 120 include titanium, titanium alloys, stainless steel, cobalt/chromium/molybdenum, etc., which are manufactured by machining, forging, casting or metal injection molding; plastics such as polyethylene with ultra high molar mass (molecular weight) (UHMWPE), polyether ether ketone (PEEK), etc., which are manufactured by injection molding or compression molding; ceramics; graphite; and others. Optionally, the endplates may be coated with hydroxyapatite, titanium plasma spray, or other coatings to enhance bony ingrowth.

As noted above, the upper and lower endplates typically have a length of from about 5 mm to about 40 mm, preferably from about 10 mm to about 25 mm, a width of from about 2 mm to about 50 mm, preferably from about 10 mm to about 35 mm, and a thickness of from about 0.25 mm to about 6 mm, preferably from about 1 mm to about 4 mm. The sizes of the upper and lower endplates are selected primarily based upon the size of the void between adjacent vertebral bodies to be occupied by the prosthetic disc. Accordingly, while endplate lengths and widths outside of the ranges listed above are possible, they are not typical. The upper surface of the upper endplate 110 and the lower surface of the lower endplate 120 are preferably each provided with a mechanism for securing the endplate to the respective opposed surfaces of the upper and lower vertebral bodies between which the prosthetic disc is to be installed. For example, in FIG. 3, the upper endplate 110 includes a plurality of anchoring fins 111a-b. The anchoring fins 111a-b are intended to engage mating grooves that are formed on the surfaces of the upper and lower vertebral bodies to thereby secure the endplate to its respective vertebral body. The anchoring fins 111a-b extend generally perpendicularly from the generally planar external surface of the upper endplate 110, i.e., upward from the upper side of the endplate as shown in FIG. 3. In the FIG. 3 embodiment, the upper endplate 110 includes three anchoring fins 111a-c, although only two are shown in the cross-sectional view. A first of the anchoring fins, 111a, is disposed near an external edge of the external surface of the upper endplate and has a length that approximates the width of the upper endplate 110. A second of the anchoring fins, 111b, is disposed at the center of external surface of the upper endplate and has a relatively shorter length, substantially less than the width of the upper endplate 110. Each of the anchoring fins 111a-b has a plurality of serrations 112 located on the top edge of the anchoring tin. The serrations 112 are intended to enhance the ability of the anchoring fin to engage the vertebral body and to thereby secure the upper endplate 110 to the spine.

Similarly, the lower surface of the lower endplate 120 includes a plurality of anchoring fins 121a-b. The anchoring fins 121a-b on the lower surface of the lower endplate 120 are identical in structure and function to the anchoring fins 111a-b on the upper surface of the upper endplate 110, with the exception of their location on the prosthetic disc. The upper and lower anchoring fins are not necessarily identical or similar; they could be different from each other in terms of geometry, size, or location. Such differences are used to accommodate anatomical differences between the superior and inferior vertebral bodies. The anchoring fins 121a-b on the lower endplate 120 are intended to engage mating grooves formed on the lower vertebral body, whereas the anchoring fins 111a-b on the upper endplate 110 are intended to engage mating grooves on the upper vertebral body. Thus, the prosthetic disc 100 is held in place between the adjacent vertebral bodies.

The anchoring fins 111, 121 may optionally be provided with one or more holes or slots 115, 125. The holes or slots help to promote bony ingrowth that assist in anchoring the prosthetic disc 100 to the vertebral bodies.

The upper endplate 110 contains a plurality of slots 114 through which the fibers 140 may be passed through or wound, as shown. The actual number of slots 114 contained on the endplate is variable. Increasing the number of slots will result in an increase in the circumferential density of the fibers holding the endplates together. In addition, the shape of the slots may be selected so as to provide a variable width along the length of the slot. For example, the width of the slots may taper from a wider inner end to a narrow outer end, or visa versa. Additionally, the fibers may be wound multiple times within the same slot, thereby increasing the radial density of the fibers. In each case, this improves the wear resistance and increases the torsional and flexural stiffness of the prosthetic disc, thereby further approximating natural disc stiffness. In addition, the fibers 140 may be passed through or wound on each slot, or only on selected slots, as needed.

As described above, the purpose of the fibers 140 is to hold the upper endplate 110 and lower endplate 120 together and to limit the range-of-motion to mimic the range-of-motion and torsional and flexural resistance of a natural disc. Accordingly, the fibers preferably comprise high tenacity fibers with a high modulus of elasticity, for example, at least about 100 MPa, and preferably at least about 500 MPa. By high tenacity fibers is meant fibers that can withstand a longitudinal stress of at least 50 MPa, and preferably at least 250 MPa, without tearing. The fibers 140 are generally elongate fibers having a diameter that ranges from about 100 µm to about 1000 µm, and preferably about 200 µm to about 500 µm. Optionally, the fibers may be processed (e.g., injection molded or extruded) with an elastomer to encapsulate the fibers, thereby providing protection from tissue ingrowth and improving torsional and flexural stiffness, or the fibers may be coated with one or more other materials to improve fiber stiffness and wear. Additionally, the core may be injected with a wetting agent such as saline to wet the fibers and facilitate the mimicking of the viscoelastic properties of a natural disc.

The fibers 140 may be fabricated from any suitable material. Examples of suitable materials include polyester (e.g., Dacron®), polyethylene, polyaramid, poly-paraphenylene terephthalamide (e.g., Kevlar®), carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like.

The fibers 140 may be terminated on an endplate by tying a knot in the fiber on the superior surface of an endplate. Alternatively, the fibers 140 may be terminated on an endplate by slipping the terminal end of the fiber into a slot on an edge of an endplate, similar to the manner in which thread is retained on a thread spool. The slot may hold the fiber with a crimp of the slot structure itself, or by an additional retainer such as a ferrule crimp. As a further alternative, tab-like crimps may be machined into or welded onto the endplate structure to secure the terminal end of the fiber. The fiber may then be closed within the crimp to secure it. As a still further alternative, a polymer may be used to secure the fiber to the endplate by welding. The polymer would preferably be of the same material as the fiber (e.g., PE, PET, or the other materials listed above). Still further, the fiber may be retained on the endplates by crimping a cross-member to the fiber creating a T-joint, or by crimping a ball to the fiber to create a ball joint.

The core member 130 is intended to provide support to and to maintain the relative spacing between the upper endplate 110 and lower endplate 120. The core member 130 is made of a relatively compliant material, for example, polyurethane or silicone, and is typically fabricated by injection molding. A preferred construction for the core member includes a nucleus formed of a hydrogel and an elastomer reinforced fiber annulus. For example, the nucleus, the central portion of the core member 130, may comprise a hydrogel material such as a water absorbing polyurethane, polyvinyl alcohol (PVA), polyethylene oxide (PEO), polyvinylpyrrolidone (PVP), polyacrylamide, silicone, or PEO based polyurethane. The annulus may comprise an elastomer, such as silicone, polyurethane or polyester (e.g., Hytrel®), reinforced with a fiber, such as polyethylene (e.g., ultra high molecular weight polyethylene, UHMWPE), polyethylene terephthalate, or poly-paraphenylene terephthalamide (e.g., Kevlar®).

The shape of the core member 130 is typically generally cylindrical or bean-shaped, although the shape (as well as the materials making up the core member and the core member size) may be varied to obtain desired physical or performance properties. For example, the core member 130 shape, size, and materials will directly affect the degree of flexion, extension, lateral bending, and axial rotation of the prosthetic disc.

The annular capsule 150 is preferably made of polyurethane or silicone and may be fabricated by injection molding, two-part component mixing, or dipping the endplate-core-fiber assembly into a polymer solution. A function of the annular capsule is to act as a barrier that keeps the disc materials (e.g., fiber strands) within the body of the disc, and that keeps natural ingrowth outside the disc.

II. Core Structures

Several alternative core structures are described hereinbelow. These core structures are preferably incorporated in one or more of the prosthetic intervertebral discs constructed according to the descriptions above, or they may be used or adapted for use with other known prosthetic discs.

Turning to FIGS. 4A-4C, a first alternative core structure is shown. The core structure includes a substantially cylindrical core member 150 that is configured to be located between a pair of endplates 110, 120 in a prosthetic intervertebral disc. The endplates 110, 120, as shown in FIG. 4C, have a size, shape, and are made of materials such as any of those described elsewhere herein. The core member 150 is a solid, cylindrical structure having a length and width adapted to substantially occupy the internal volume of the prosthetic disc between the upper and lower endplates. The core 150 may comprise any one or more of the materials described above, including hydrogels, polyurethanes, polyvinyl alcohol (PVA), polyethylene oxide (PEO), polyvinylpyrrolidone (PVP), polyacrylamide, silicone, PEO based polyurethane, elastomers such as silicone, polyurethane, or polyester (e.g., Hytrel®), reinforced with a fiber, such as polyethylene (e.g., ultra high molecular weight polyethylene, UHMWPE), polyethylene terephthalate, or poly-paraphenylene terephthalamide (e.g., Kevlar®).

In some preferred embodiments, the core member 150 includes an inner core member 152 and an outer core member 154 as shown, for example, in FIG. 4B. The inner 152 and outer 154 core members may be constructed of a single material, or they may be constructed of different materials, or they may be constructed of the same material having different material properties. When different materials or different material properties are used, the performance of the core 150 may be varied to obtain desired results. For example, a relatively harder material (i.e., higher durometer measurement) may be used to construct the inner core member 152 while a relatively softer material (i.e., lower durometer measurement) is used to construct the outer core member 154. In this manner, the inner core member 152 is adapted to provide a primary source of support for the core member 150 and the outer core member 154 provides compliance for the composite core structure.

Due to the substantially cylindrical shape of the core member 150, the endplates 110, 120 each engage the core member 150 over a limited contact area along the upper and lower surface of the core member. The compressive loading that is applied to each of the endplates is applied perpendicular to the longitudinal axis of the cylindrical core member. Additionally, as the load on the upper 110 and lower 120 endplates increases, the load bearing contact areas will enlarge due to the flattening out of the generally cylindrical core member 150. This flattening out of the core member contributes to maintaining the integrity of the core and its performance under higher compressive loads, and provides a progressively greater resistive force against the compression force of the two endplates.

The cylindrical shape of the core member 150 also allows for a relatively larger amount of rotation of the upper and lower endplates around the longitudinal axis of the core member—as shown, for example, by the arrows "R" in FIG. 4C—than is allowed by an otherwise similar core having a more conventional shape. This rotation of the endplates 110, 120 around the longitudinal axis of the core member 150 is intended to mimic the rotation provided by the natural disc, or to produce other desired effects. The prosthetic disc 100 is preferably oriented within the space between the upper and lower vertebral bodies such that the rotation about the longitudinal axis of the core member is available for the desired effect.

The upper and lower endplates 110, 120 are each connected directly to the core member 150, or the endplates are connected to each other by fibers woven through or connected to the endplates, as described elsewhere herein. Additional mechanisms for connecting the disc components may be utilized as well, as will be appreciated by those of skill in the art. In addition, an optional annular capsule may be attached to the prosthetic disc in the manner described above.

Turning to FIGS. 5A and 5B, another alternative core structure is shown. The core structure includes a plurality of core members 160 having different performance properties that provide varying load bearing properties and the ability to vary the center of rotation of the core structure. For example, FIG. 5A shows a core structure having two core members 160a, 160b. An anterior core member 160a is formed of one or more materials or is otherwise constructed in a manner that provides a core member having a relatively low stiffness. A posterior core member 160b is formed of one or more materials or is otherwise constructed in a manner that provides a core member having a relatively high stiffness. In this way, the relatively stiffer posterior core member 160b will support a greater amount of the load than the relatively soft, flexible anterior core member 160a, and the anterior core member 160a will have relatively greater movement because it is located away from the axis of rotation. In addition, by varying the stiffnesses of each of the anterior core member 160a and the posterior core member 160b, the axis of rotation of the core structure is able to be moved to thereby provide for different ranges of motion of each of the anterior and posterior core members.

Another example is shown in FIG. 5B. A relatively stiff central core member 160a is located between a first relatively softer peripheral core member 160b and a second relatively softer peripheral core member 160a. This configuration provides relatively softer, more mobile core members to be located on the periphery of the core structure to provide an increased range of motion for the core structure, while a relatively stiffer core member is located near the center of the core structure to provide the primary axial load bearing portion of the core structure.

Other variations of the structures shown in FIGS. 5A and 5B are also possible. For example, additional core members may be provided, such as four, five, or six or more discrete core members. Each of the core members may have a cylindrical cross-sectional shape, such as the core members shown in FIGS. 5A-B, or they may be of different cross-sectional shapes, such as oval, kidney-shaped, rectangular, or other geometric or irregular shape. Each of the core members may be formed of materials or otherwise be configured such that it is relatively stiff, relatively soft and flexible, or some other desired physical property. The individual core members may then be placed at desired locations between the two endplates of the core structure to obtain desired physical effects, such as by varying the range of motion or the degree of load borne by each discrete core member.

In addition, where the core structure is formed using fiber windings as described above, the location of the fiber windings are adapted to cooperate with the locations of the discrete core members located between the upper endplate and lower endplate. For example, in one embodiment, the fiber windings are located only around the periphery of the endplates themselves. In alternative embodiments, the windings are located around the periphery of each of the individual core members. In still other embodiments, the fiber windings are formed in a continuous serpentine pattern, or one or more figure-8 patterns, each surrounding each of the core members. Other variations of the winding pattern may be implemented to obtain desired physical properties of the core structure.

Figure 6A:
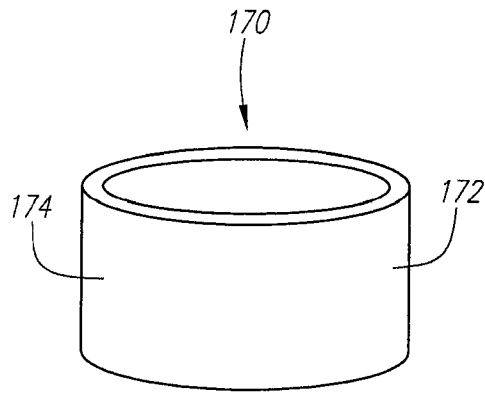
Figure 6B:
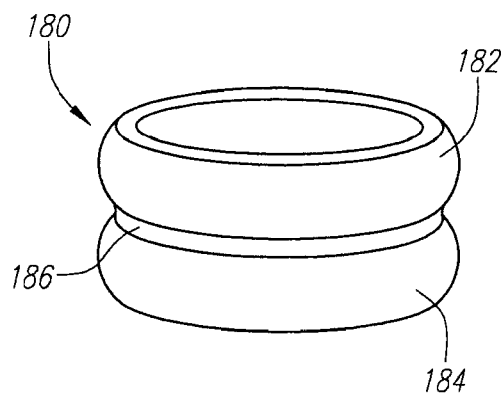
Figure 6C:
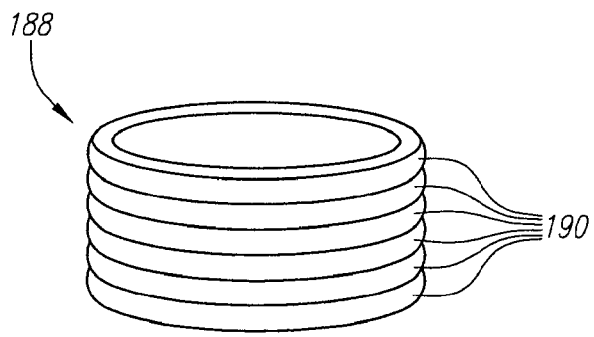
Figure 6D:
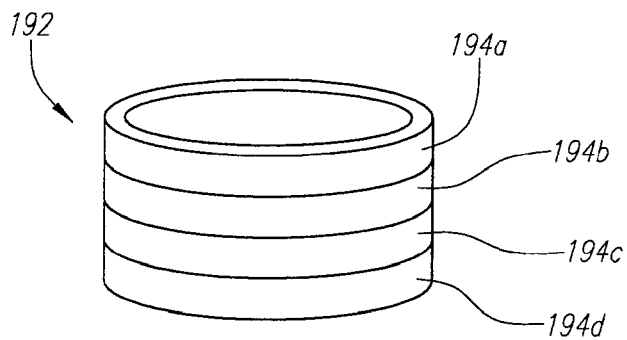
Figure 6E:
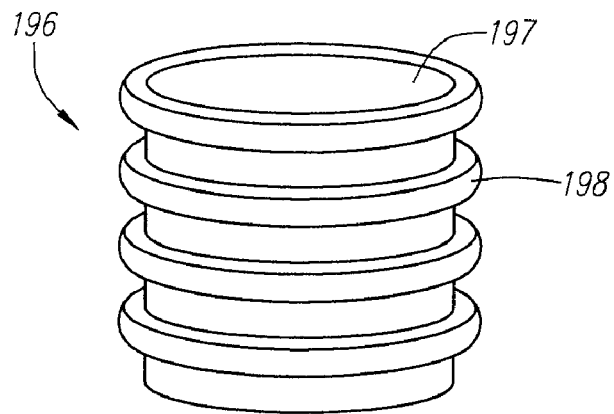
Figure 6F:
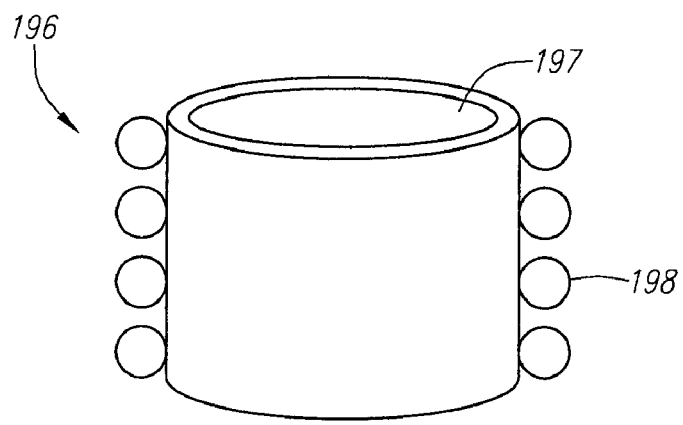
Figure 6G:
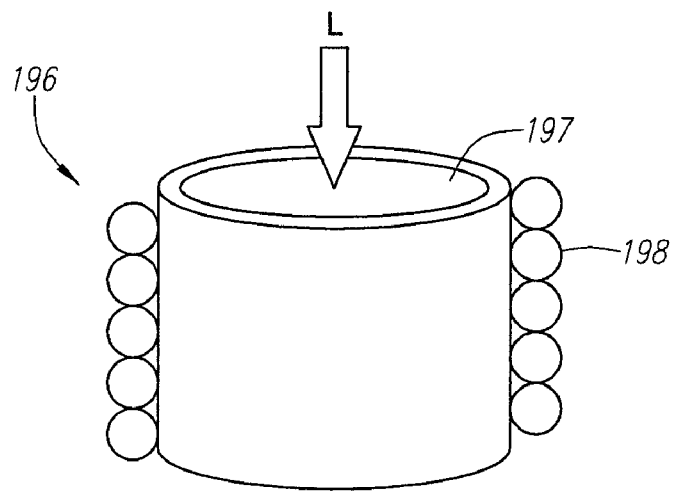
Figure 6P:
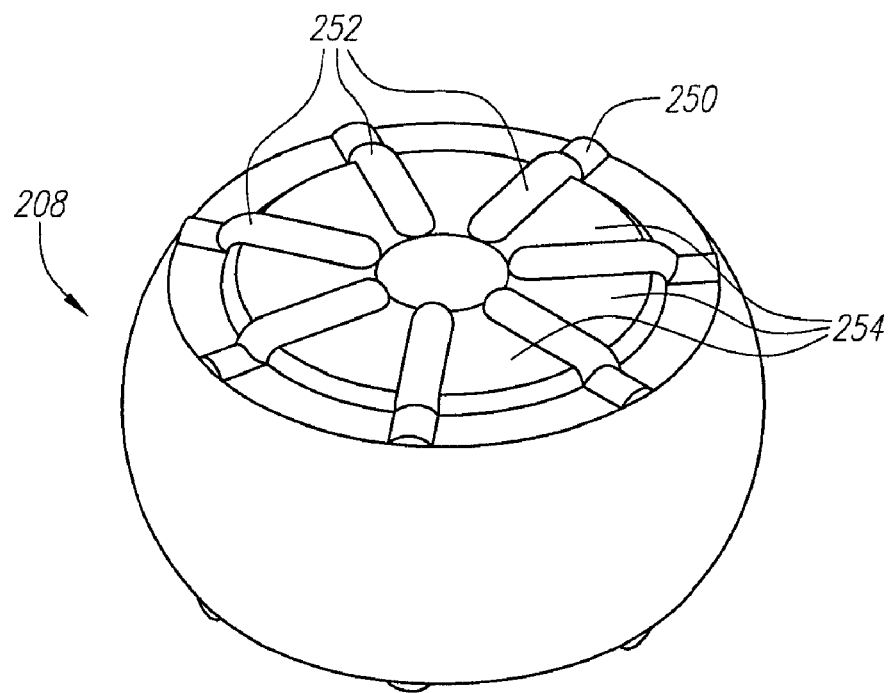
Figure 6Q:
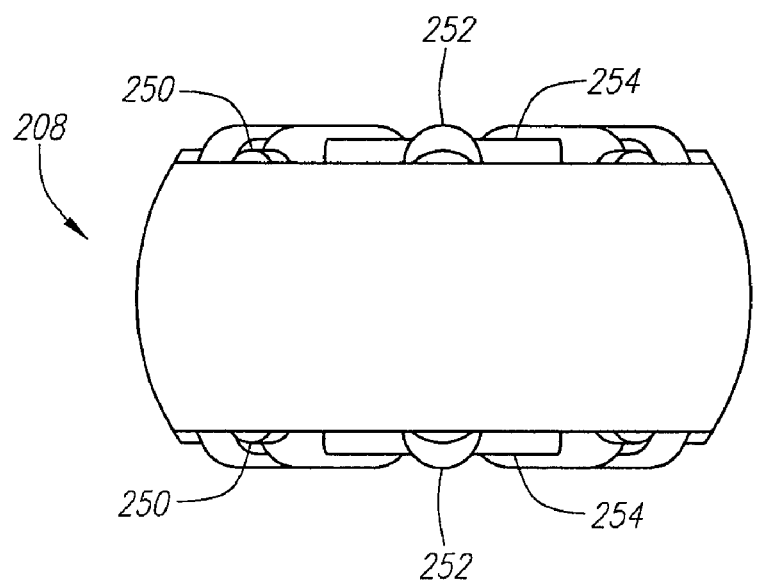
Figure 6R:
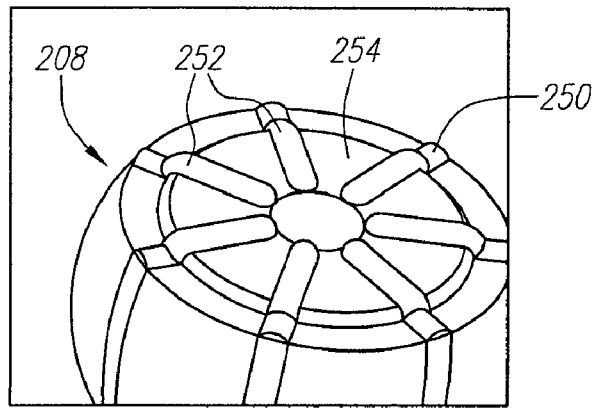
Figure 6S:
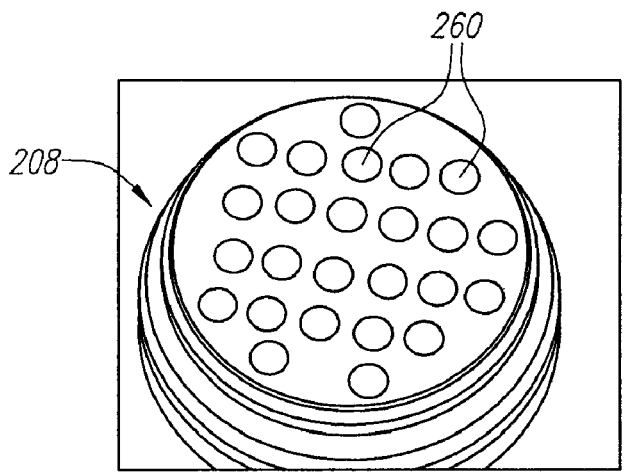
Figure 6T:
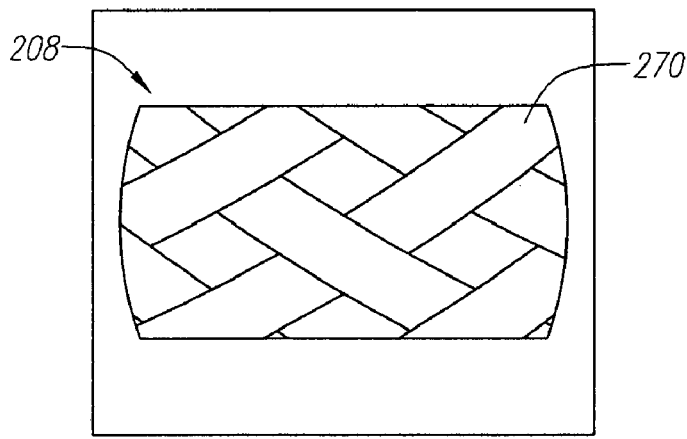

Turning to FIGS. 6A-6T, several additional alternative core members are shown. The exemplary core members are formed of materials or are otherwise constructed to provide varying stiffnesses or other material properties to accommodate different loads or loading configurations. As a first example, as shown in FIG. 6A, a generally cylindrical core member 170 includes a posterior aspect 172 and an anterior aspect 174. In a preferred embodiment, the anterior aspect 174 is less stiff than the posterior aspect 172. The difference in stiffness may be gradual, such as by forming a stiffness gradient through the core member 170 from the anterior aspect 174 to the posterior aspect 172. Alternatively, the difference in stiffness may be stark, such as by forming the portion of the core member 170 containing the anterior aspect 174 of a different material, or in an otherwise different manner, from the portion of the core member containing the posterior aspect 172. Other variations and methods are also contemplated to obtain the difference in stiffness or other material properties between the anterior aspect 174 and posterior aspect 172 of the core member 170.

Other example core members are shown in FIGS. 6B-D. Each of these exemplary core members is generally cylindrical. Turning to the core member shown in FIG. 6B, the core member 180 includes an upper portion 182 and a lower portion 184 located on either side of a middle portion 186. The upper portion 182 and lower portion 184 are preferably formed of a relatively stiff polymeric material, or other material having a relatively high degree of stiffness. The middle portion 186 is preferably formed of a relatively softer material having a relatively lower degree of stiffness. This construction provides a core structure 180 having a relatively larger degree of torsional motion relative to a comparable core not having a softer middle portion. Similarly, the core member 188 shown in FIG. 6C is an integrated structure formed of a polymeric or other material, and has a plurality of grooves 190 formed around the periphery of the core member. Each of the grooves has a depth and width that is selected to obtain desired performance characteristics, such as increased or decreased torsional resistance and load bearing capacity. Finally, the core member 192 shown in FIG. 6D is a composite structure including a plurality of sections 194*a-n*. Each section is formed of a material or is otherwise constructed to have desired physical properties, and the composite structure is formed such that the overall core member 192 possesses a desired combination of such physical properties to obtain a desired performance. For example, the core member 192 may be formed by alternating stiff sections with flexible, soft sections. Although the Figure shows four such sections 194*a-d*, the core member may be provided with more or fewer sections to obtain desired results.

Another example of a core member is shown in FIGS. 6E-G. The core member 196 includes a generally cylindrical central portion 197 that is typically formed of a polymeric material or other suitable core member material. A coiled member 198 is positioned around the periphery of the central portion 197. The coiled member 198 may be in the form of a compression spring or other suitable member. In the embodiment shown, the coiled member 198 provides a restraint substantially preventing radial expansion of the central portion as it is brought under load. For example, FIG. 6F shows the core member 196 in an unloaded, uncompressed state in which the coiled member 198 is not compressed and extends around the periphery of the central portion. As a load "L" is applied, as shown in FIG. 6G, the central portion 197 and the coiled member 198 are compressed. The coiled member 196 substantially prevents radial expansion, or bulging, of the central portion 197 of the core member. In an alternative embodiment, not shown, the coiled member may be replaced with a thin outer layer that is corrugated or otherwise shaped to provide for loading and unloading of the central portion while substantially preventing radial expansion of the central portion of the core member.

Another example of a core member is shown in FIG. 6H. The generally cylindrical core member 200 includes an upper portion 202 and a lower portion 204, with a coupler portion 206 located between the upper portion 202 and lower portion 204. Each of the upper portion 202 and lower portion 204 is preferably formed of a polymeric material or other suitable material having a relatively high stiffness. The coupler portion 206 is preferably formed of a material that is sufficiently soft and flexible to allow for axial compression and for a relatively high degree of rotational freedom.

Additional examples of core members are illustrated in FIGS. 6I-K. These exemplary core members include mechanisms adapted to increase the height of the core member. In several preferred embodiments, the height of the core member is able to be adjusted in situ, e.g., after deployment of the core member between two vertebral bodies. Turning first to FIG. 6I, the core member 208 includes a top portion 210 and a separate bottom portion 216. The top portion includes an upper end 212 and a generally cylindrical upper side wall 214. The bottom portion 216 includes a bottom end 218 and a generally cylindrical bottom side wall 220. The inner portion of the upper side wall 222 and the outer portion of the bottom side wall 224 each includes a mating member, such as mating threads, notches and tabs, or other similar mechanism. The mating members of the top portion 210 and bottom portion 216 are adapted to selectively connect the top portion to the bottom portion, and to allow for adjustment of the connection position such that the height of the core member 208 is able to be adjusted. For example, in the case of mating screw threads, the height of the core member 208 may be adjusted by rotating the top portion 210 relative to the bottom portion 216 to screw down the top portion or to raise the top portion relative to the bottom portion. In the case of mating notches and tabs, the top portion 210 may be raised or lowered relative to the bottom portion 216 to place the core member at a desired overall height.

An example of a core member 208 having a top portion 210 and bottom portion 216 connected by a mating member is shown in FIG. 6J. The mating member comprises a pair of tabs 230 formed on the outer periphery of the bottom sidewall, and a notch 232 formed on the inner periphery of the upper sidewall. In this configuration, the top portion 210 may be placed in a first position relative to the bottom portion 216, wherein the top portion notch 232 engages the lower tab 230 of the bottom portion. The first position corresponds to a relatively lower overall height of the core member 208. Alternatively, the top portion 210 may be placed in a second position relative to the bottom portion 216, wherein the top portion notch 232 engages the upper tab 230 of the bottom portion. The second position corresponds to a relatively higher overall height of the core member.

Another example of a core member 208 having a top portion and bottom portion connected by a mating member is shown in FIG. 6K. The mating member comprises mating threads 236 formed on the outer periphery of the bottom sidewall 220 and the inner periphery of the upper sidewall 214. In this configuration, the top portion 210 is rotated relative to the bottom portion 216 (or the bottom portion is rotated relative to the top portion) to cause the top portion to either raise or lower relative to the bottom portion, thereby adjusting the overall height of the core member 208.

FIGS. 6L-N illustrate a method of forming a composite core member 208. In a first step, shown in FIG. 6L, a center portion 240 of the core member 208 is formed of a relatively stiff material, such as a polymeric material or other suitable material. The center portion may be extruded, molded, or formed in any other suitable manner known to those of skill in the art. A braid 242 is then applied to or placed on the center portion 240, as shown, for example, in FIG. 6M. The braid 242 is preferably formed of a material having properties that provide a desired amount of torsional resistance to the core member 208 to obtain a desired performance characteristic for the core structure. A preferred material for use as a braid is a polymer, such as polyester, polyethylene, or Kevlar. Other materials that may be used include metals such as stainless steel, or suitable metal alloys. Once the braid is applied, an outer layer 244 is applied over the braid 242 and the center portion 240 to finish the core member 208. The outer layer 244 preferably comprises a relatively soft, flexible material to enhance the bending, flexion, and extension of the core member.

FIGS. 6P-T illustrate several core constructions and methods adapted to facilitate sterilization of the core. Turning first to FIGS. 6P, 6Q, and 6R, a core member 208 is shown having a plurality of furrows 250 formed on its upper (superior) surface and lower (inferior) surface. The core member 208, as illustrated in the Figures, is generally cylindrical, although other core member shapes and sizes are also contemplated. For example, the core member 208 may be provided having a construction or formed of materials in a manner according to any of the other embodiments described herein. The furrows 250 formed on the upper and lower surfaces include a first plurality of raised, semi-circular portions forming a generally radial pattern 252 with each of the first plurality of raised, semi-circular portions extending from a location near the center of the surface radially to the outer edge. The furrows 250 include a second plurality of raised, semi-circular portions forming a generally circular pattern 254 with each of the second plurality of raised, semi-circular portions extending in a generally circular pattern near the edge of the surface of the core member. The generally radial pattern 252 formed by the first plurality of raised, semi-circular members thereby intersects the generally circular pattern 254 formed by the second plurality of raised, semi-circular portions.

The purpose of the furrows 250 formed on the upper surface and lower surface of the core member is to separate the main portion of the core member 208 from each of the upper endplate and lower endplate. This provides a relatively small volume of unoccupied space between the core member 208 and the upper endplate and lower endplate. The unoccupied space facilitates passage of a sterilization medium between the core member and the respective endplates, thereby enhancing the effectiveness of the sterilization procedure.

As noted, the furrows 250 illustrated in the embodiments shown in FIGS. 6P-R are generally in the shape of raised, semi-circular portions extending outward from the upper surface and lower surface of the core member. Each of the raised, semi-circular portions is generally elongated and extends in either the generally radial pattern or the generally circular pattern. Other patterns and other shapes of the furrows are also contemplated. For example, the furrows may be formed by a plurality of generally aligned raised portions, by a plurality of concentric circular raised portions, or by any other geometric or non-geometric pattern.

Another core member embodiment is shown in FIG. 6S. There, a core member 208 includes a plurality of raised bumps 260 formed on its upper surface and lower surface (the lower surface is not shown in FIG. 6S). The raised bumps 260 also function by separating the main portion of the core member 208 from the upper endplate and the lower endplate, thereby providing a relatively small unoccupied volume of space between the core member and each of the endplates. As described above, this unoccupied volume of space facilitates sterilization by enhancing the ability of the sterilization medium to pass between the core member and each of the endplates.

Still another core member embodiment is shown in FIG. 6T. In this embodiment, the core member 208 includes an integrated mesh 270 formed of polyethylene terephthalate (PET). The integrated mesh 270 includes a plurality of non-geometric raised portions that function to create an unoccupied space between the main portion of the core member and each of the upper and lower endplates. As noted above, this unoccupied space facilitates sterilization of the resulting prosthetic disc by enhancing the ability of the sterilization media to pass between the core member 208 and each of the endplates.

Figure 7:
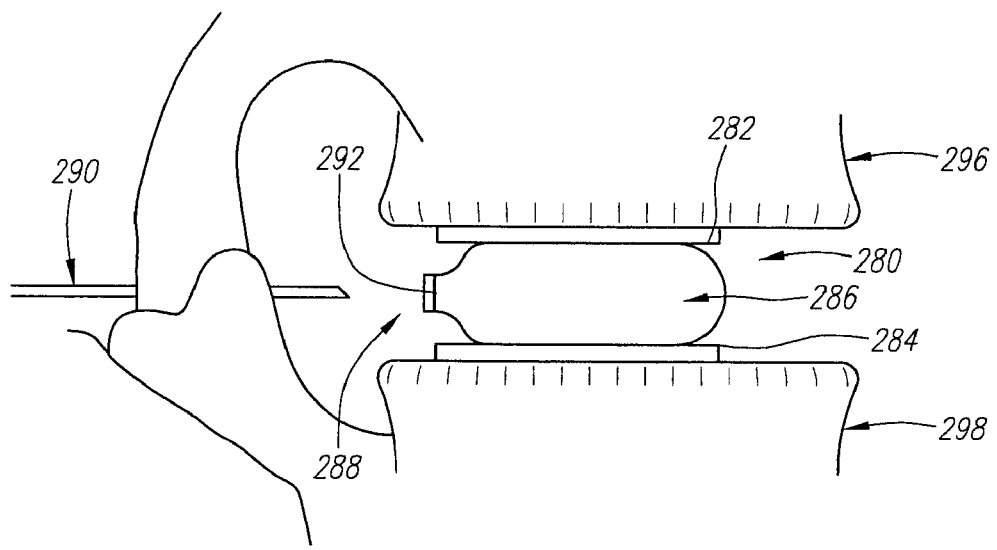

Turning to FIGS. 7 through 10, several embodiments of adjustable core structures are shown. In these preferred embodiments, the core structures are configured such that they may be adjusted in situ, e.g., after deployment between a pair of vertebral bodies. In FIG. 7, a prosthetic disc 280 is implanted between a pair of adjacent vertebral bodies 296, 298. The prosthetic disc 280 includes an upper endplate 282, a lower endplate 284, and a core member 286 located between the upper and lower endplates. The upper endplate 282 and lower endplate 284 preferably are secured to the respective vertebral bodies in a manner described above in relation to the other exemplary disc structures described herein. The core member 286 comprises a hollow member that is adapted to receive an inflation media via an inflation port 288 to thereby adjust the effective volume of the core member 286. The amount of inflation media contained within the hollow member will determine the physical properties of the core member 286. For example, when the hollow portion of the core member 286 is full of inflation media, the core member 286 will be relatively firm and will have a volume that is at or near its maximum. As the amount of inflation media in the hollow portion of the core member is decreased, the core member 286 will gradually soften and become more flexible, and its volume will decrease. Thus, the user is able to adjust the physical properties and size of the core member by adjusting the amount of inflation media contained in the hollow portion of the core.

The core member 286 may be provided in any size or shape needed to achieve desired clinical results. For example, the core member may occupy the entire space between the upper endplate 282 and lower endplate 284, or it may occupy only a portion of the space with one or more other core member portions of different constructions making up the remainder. The core member 286 may be generally cylindrical, kidney-shaped, or any other geometric or irregular shape suitable for a particular application.

FIG. 7 illustrates a method for adjusting the volume of the core member 286. A needle 290 is inserted into the spinal region to provide access to the hollow portion of the core member. The needle 290 is inserted through the inflation port 288 into the hollow portion of the core member. Inflation media is then added to or taken from the hollow portion by way of the inflation needle 290. Preferably, a radiopaque marker 292 or other similar indicator is fixed to the core member 286 at the location of the inflation port 288 to facilitate locating the inflation port via fluoroscopy.

Figure 8:
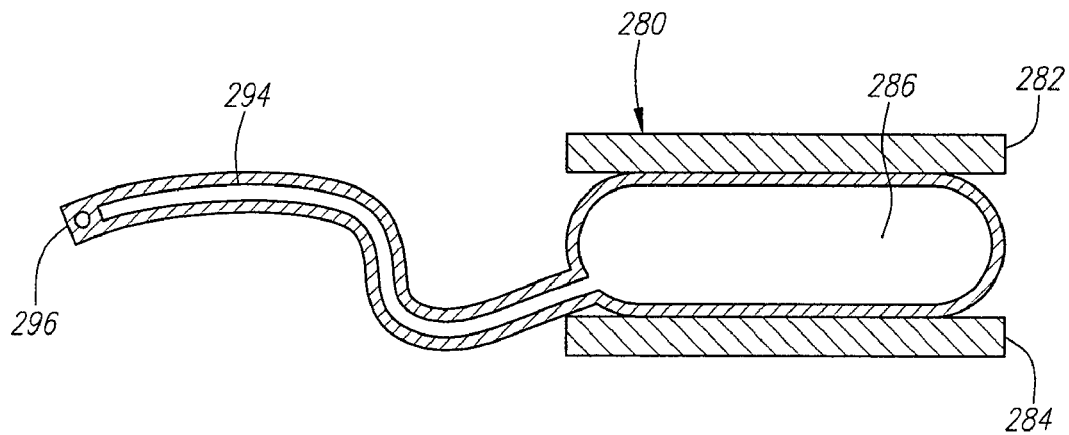

FIG. 8 illustrates an alternative structure for the core member that includes a fluid communication lumen 294. The fluid communication lumen 294 comprises an extended tubular member defining an internal lumen that connects the interior of the hollow portion of the core member to a port 296 located at the proximal end of the fluid communication lumen. The fluid communication lumen 294 extends outward from the posterior portion of the core member 286. Preferably, when the prosthetic disc 280 is implanted, the fluid communication lumen 294 is oriented such that access may be obtained to the port 296 at the proximal end of the channel without having the need to obtain access to the interior of the spinal column. For example, the proximal end of the fluid communication lumen 294 may be located just beneath the skin surface of the patient in a location that provides ready access for adjustment of the core member 286. Thus, the port 296 may be accessed by an inflation needle or other member just beneath the surface of the skin, and the inflation media injected or removed from the hollow portion of the core member through the fluid communication lumen 294.

In either of the embodiments shown in FIGS. 7 and 8, the prosthetic disc 280 may be implanted while the core member 286 is in its uninflated condition, corresponding with its lowest profile. This will provide the ability to implant the prosthetic disc 280 through a relatively smaller implantation window than would be needed if the prosthetic disc were to be deployed in its fully inflated condition. Alternatively, if the prosthetic disc 280 is to be deployed in a disassembled condition, the core member 286 still is able to be implanted in its lowest profile state, and then inflated after deployment, in situ. In either case, the ability to deliver the core member 286 in its uninflated state allows the surgeon to implant the device through a relatively smaller implantation window.

Preferably, the inflation media comprises saline or another incompressible inert fluid. Other materials may be used for desired effect. The inflation media may be added to or removed from the core member 286 at any time post operatively to adjust the performance of the prosthetic disc 280. It is also contemplated that the hollow portion of the core member may comprise a plurality of independent or interdependent chambers, each of which may be adjustable to alter the height, size, or physical properties of one or more portions of the core member. For example, a system of four chambers would provide the ability to adjust the orientation of the core member to adjust for scoliosis, kyphosis, and lordosis.

Figure 9A:
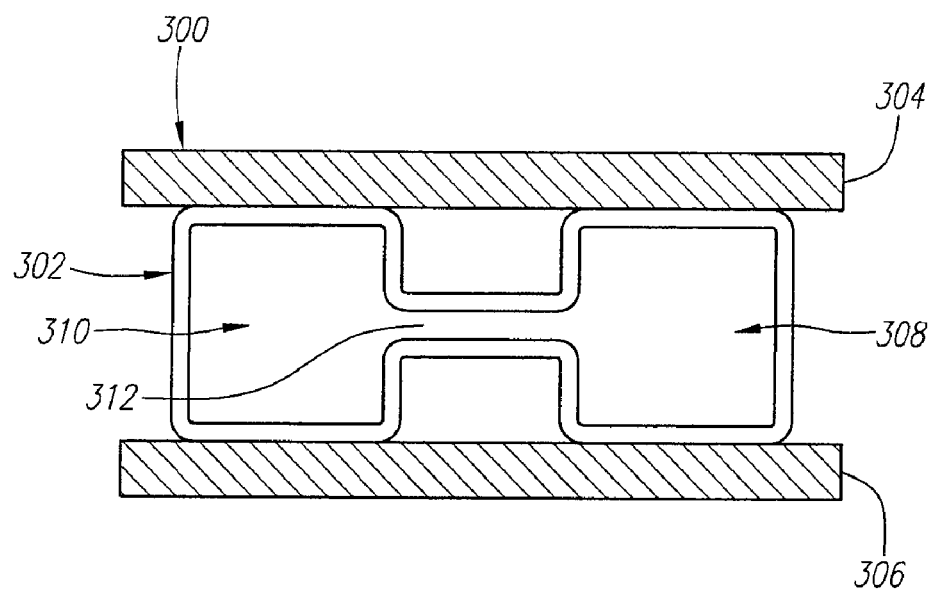
Figure 9B:
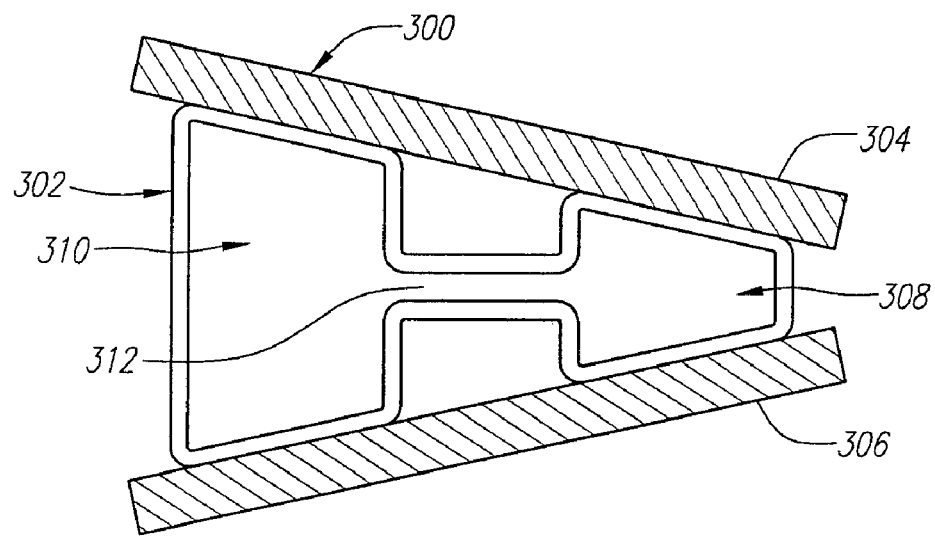

An example of a multi-chamber core member is shown in FIGS. 9A-B. The core member 302 is located between an upper endplate 304 and a lower endplate 306, and includes a first fluid chamber 308, a second fluid chamber 310, and a fluid communication channel 312 interconnecting the first and second fluid chambers. The core member 302 also optionally includes an inflation port and (also optionally) a fluid inflation lumen to provide a mechanism for inflating or deflating the core member in situ, as described above in relation to FIGS. 7 and 8. The two fluid chambers 308, 310 provide the compression stiffness required for the core member of the prosthetic disc 300. The two fluid chambers 308, 310 are formed in any desired shape suitable for providing the desired physical performance, such as a generally cylindrical shape, kidney-shaped cross-section, or other geometric or irregular shape.

FIG. 9A illustrates the core member 302 in a condition in which each of the first fluid chamber 308 and second fluid chamber 310 is of a generally equivalent size and shape. An inflation fluid, such as saline, occupies the interior space of each of the fluid chambers, and is able to flow from the first fluid chamber 308 to the second fluid chamber 310 by way of the fluid communication channel 312. FIG. 9B illustrates the core member in a flexed condition. Fluid has passed from the first fluid chamber 308 to the second fluid chamber 310 due to the flexion loading of the upper and lower endplates 304, 306. The core member allows this range of motion while providing a physiological stiffness in compression by providing the ability for one or more of the fluid chambers to expand to accommodate the fluid flow required to provide the range of motion.

Although two fluid chambers are shown in the embodiments illustrated in FIGS. 9A-B, other embodiments containing more than two fluid chambers are also contemplated. For example, a single core member having three or more separate fluid chambers may be provided. In such a case, fluid communication channels may be provided between each of the fluid chambers, or only for selected chambers. In addition, separate core members may be provided and fluid flow between the separate core members may be provided by a fluid communication member connecting the two or more separate core members.

Figure 10:
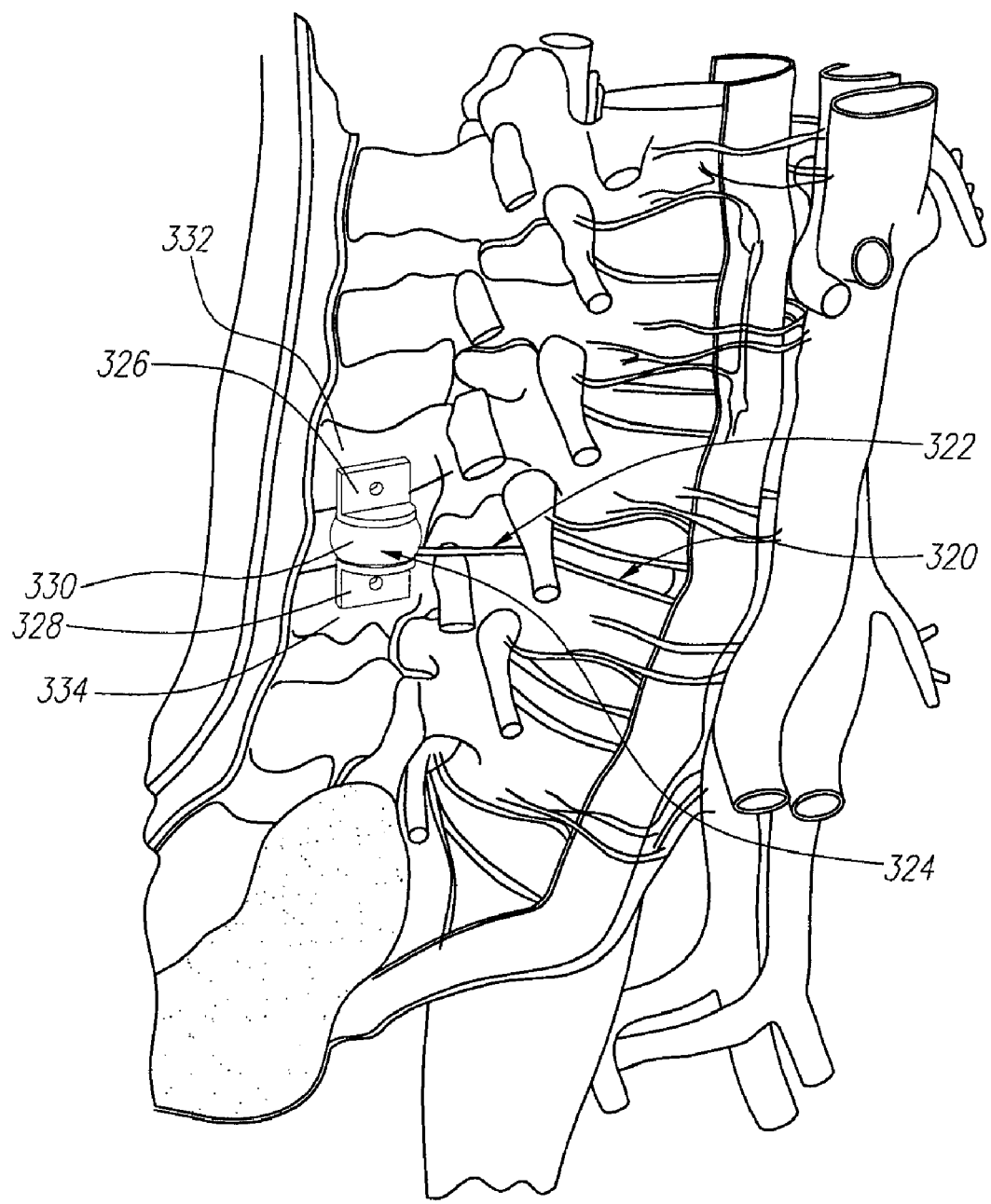

FIG. 10 shows a prosthetic disc 320 having a fluid communication channel 322 connecting to an interspinous stabilization device 324. The prosthetic disc 320 is preferably of a construction identical or similar to one of those described above in relation to FIGS. 7, 8, and 9A-B, having an upper endplate attached to an upper vertebral body, a lower endplate attached to a lower vertebral body, and a core member located between the two endplates. The core member includes at least one fluid chamber. The interspinous stabilization device 324 includes an upper fixation member 326 attached to an upper transverse process 332, a lower fixation member 328 attached to a lower transverse process 334, and a fluid chamber 330 extending between and attached to each of the upper fixation member 326 and the lower fixation member 328. The fluid chamber 330 functions by providing resistance to compression, flexion, and rotation of the vertebral bodies to which the interspinous stabilization device 324 is attached.

The fluid communication channel 322 provides fluid flow between the core member of the prosthetic disc 320 and the fluid chamber 330 of the interspinous stabilization device 324. Thus, as the spine flexes or extends, fluid will flow between the prosthetic disc 320 and the interspinous stabilization device 324, thereby increasing the volume of one of the components and decreasing the volume of the other. Depending on the relative sizes of the fluid chambers of the interspinous stabilization device and the fluid chambers of the core member of the prosthetic disc, the motion and range of motion of the spine is controlled.

It will be understood that the core member of the prosthetic disc 320 may optionally include any one or more of the features described above in relation to the cores shown in FIGS. 7, 8, and 9A-B. For example, the core member size (e.g., height, volume) may be adjusted by provision of an inflation port and a fluid communication lumen providing fluid communication between the user and the core member. Other combinations of features are also contemplated, as will be understood by those skilled in the art.

III. Endplates and Related Mechanisms

Several alternative endplate structures and fixation mechanisms are described hereinbelow. These endplate structures and fixation mechanisms are preferably incorporated in one or more of the prosthetic intervertebral discs constructed according to the descriptions above, or they may be used or adapted for use with other known prosthetic discs.

FIG. 11 illustrates an alternative configuration of an endplate 110 for use in a prosthetic disc and configured for implantation through a minimally invasive, posterior implantation approach such as described, for example, in the '276 application. The endplate 110 has a curved or kidney bean shape with two parallel keels 111a, 111b having a similar curvature to the endplate 110. A chisel (not shown) having a similar keel configuration could also be used. The curved shape of the prosthetic disc 336 (and chisel) facilitates rotation of the disc within the intervertebral void space as it more closely matches the cross-sectional anatomy of the vertebral bodies thereby helping to avoid nerves, vessels and other bony structures along or adjacent to the implantation paths 340 used during a posterior implantation approach, as illustrated in FIG. 12A. While two parallel implantation paths 340 are shown, one for each disc 336, a single implantation path 340 may be used to implant both discs. The minimally invasive discs of the present invention may also be implanted from a posterior-lateral or a lateral approach as illustrated in FIG. 12B. Here, a single disc 336 has been implanted by way of an implantation path 342 positioned anteriorly of the transverse process. The curvature of the illustrated disc also facilitates implantation by this approach as well.

FIG. 13 shows a prosthetic disc 350 including an upper endplate 352, lower endplate 354, and a generally cylindrical core member 356. The cylindrical core member 356 is preferably constructed of a hollow material such that the core member may be selectively deflated to provide a lower profile for deployment, then inflated in situ to its operative size and volume. Alternatively, the core member may be of a construction identical or similar to those described, for example, in relation to FIGS. 4A-C.

The upper endplate 352 and lower endplate 354 are preferably each of a partially cylindrical shape such that the inward-facing surfaces of each of the endplates are generally concave, and the outward-facing surfaces of each of the endplates are generally convex. The inward-facing surfaces are thereby adapted to engage and retain the generally cylindrical core member 356. In a particularly preferred embodiment, the upper endplate 352 and lower endplate 354 each have a keel 358 formed on or attached to its upper surface and lower surface, respectively. The keels 358 are adapted to engage the respective vertebral bodies to secure the endplates against movement upon implantation.

The prosthetic disc so described may be implanted in separate parts, or as a complete unit. In either case, the cylindrical core member 356 is preferably deflated or compressed prior to implantation, then inflated or expanded after implantation. The degree of inflation will determine the physical properties of the core member 356, such as the height, stiffness, and load bearing capabilities of the core member. The selectable inflation of the core member provides a prosthetic disc 350 having a minimized deployment profile while still having the necessary height, volume, and size after inflation upon deployment.

FIGS. 14A-D illustrate another alternative prosthetic disc 360 having a first, low profile position for use when deploying the device, and a second, fully expanded condition for use after deployment. The low profile position is preferable for the deployment process because it requires less boney structure to be removed during a posterior, minimally invasive implantation procedure. Removal of excess honey structure from the vertebrae may result in spinal instability, which is to be avoided where possible. On the other hand, after deployment, it is preferable to have a prosthetic disc having a relatively large cross sectional area. For example, if the artificial disc is provided with upper and lower surfaces having relatively smaller surface area, the disc has a tendency to subside, or sink, into the bone of the upper and lower vertebral bodies.

The prosthetic disc 360 shown in FIGS. 14A-D provides the ability to increase the surface area of the endplates interfacing with the vertebral bodies after implantation by raising adjacent superior and inferior surfaces. Referring to FIG. 14A, the upper endplate 362 includes a central portion 364 having a pair of anchoring fins 366 extending over at least a portion of the upper surface. A drop-leaf 368 is pivotably attached to each side of the central portion 364 along its length. Each drop-leaf 368 may be attached to the central portion by a hinge, such as a standard piano hinge, a living hinge 370, or other suitable mechanism. Each drop-leaf 368 has a first, delivery position (shown in FIG. 14A) in which the drop-leaf 368 extends downward from the edge of the central portion 364. Each drop-leaf also has a second, deployment position (shown in FIG. 14B) in which the drop-leaf 368 is raised to be coplanar with the central portion 364, thereby forming a portion of the upper endplate. Drop-leaves 378 are also formed on the lower endplate 372, which also has a central portion 374. The lower endplate drop-leaves 378 also have a first, delivery position (shown in FIG. 14A) and a second, deployment position (FIG. 14B).

FIGS. 14C-D illustrate a mechanism for supporting and stabilizing the drop-leaves after the drop-leaves are placed in the deployment position. FIG. 14D shows an upper drop-leaf 368 positioned above a lower drop-leaf 378, each in its deployment position. For clarity, the rest of the prosthetic disc 360 is not shown in FIG. 14D. Each of the upper drop-leaf 368 and lower drop-leaf 378 includes a spring slot 380 extending over its facing surface. A separation spring 382 is shown in FIG. 14C. The separation spring 382 includes a first flat end 384a, a curved spring portion 386, and a second flat end 384b. The spring 382 is adapted to be placed into the spring slots 380 of an opposed pair of upper and lower drop-leaves after the drop-leaves have been moved to the deployment position after implantation of the prosthetic disc. Once in place, the separation spring 382 maintains the spacing of the upper and lower drop-leaves to thereby provide a relatively larger surface area for each of the upper and lower endplates.

FIGS. 15A-B illustrate a prosthetic disc 390 having an elongated tubular core member 392 and a partially cylindrical upper endplate 394 and partially cylindrical lower endplate 396. Each of the endplates includes a relief portion 398 on each of the anterior and posterior ends of the endplates. The relief portions comprise a partial cutaway that extends from the leading anterior or posterior edge of the respective endplate, thereby forming a generally curved relief portion. The relief portions together cooperate to provide enhanced flexion and extension of the prosthetic disc so constructed, relative to a similarly constructed prosthetic disc not having such relief portions.

In reference to FIG. 15B, a fiber 400 is woven through a series of slots 402 formed on the edges of each of the upper endplate 394 and lower endplate 396 to secure the endplates together. The slots 402 are spaced evenly along the edges of the endplates, though unevenly spaced slots may be provided as an alternative option. One or more fiber layers 400 may be used, and each fiber layer may be formed of a different material and/or have different range of material properties, such as stiffness. In some embodiments, the fibers 400 are wound over and under the core member, and between the core and the endplates.

In reference to the prosthetic discs shown in FIGS. 16A-C, 17A-B, 18A-C, and 19A-C, the subject prosthetic discs are constructed in a manner that allows the replacement disc to closely mimic the physiology of the natural functional spinal unit. The spine is composed of motion segments, each of which is composed of three joints that together comprise a functional spinal unit. The intervertebral disc and the two facet joints create spinal stability and motion. A prosthetic disc will serve to replace the natural intervertebral disc. But, in many cases, prior prosthetic discs do not adequately compensate for the natural disc because they do not cooperate with the facet joints in the same manner as the natural disc. In addition, in cases in which a prosthetic disc is delivered to the spine by the posterior approach, the approach may require partial or total removal of the facet joints to gain access to the intervertebral space. This creates a concern about the stability of the spine and a potential biomechanical disruption that the prosthetic disc itself may not fully correct. The prosthetic discs shown in FIGS. 16A-C, 17A-B, 18A-C, and 19A-C are designed and constructed to provide the replacement functionality of the natural intervertebral disc, but also to provide the replacement functionality of the facet. In this way, the subject prosthetic discs provide the appropriate stiffness and mobility closely comparable to the entire functional spinal unit.

Figure 16A:
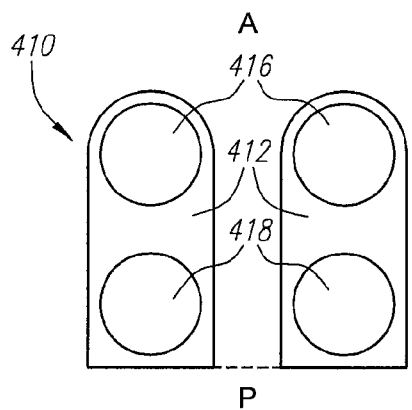
Figure 16B:
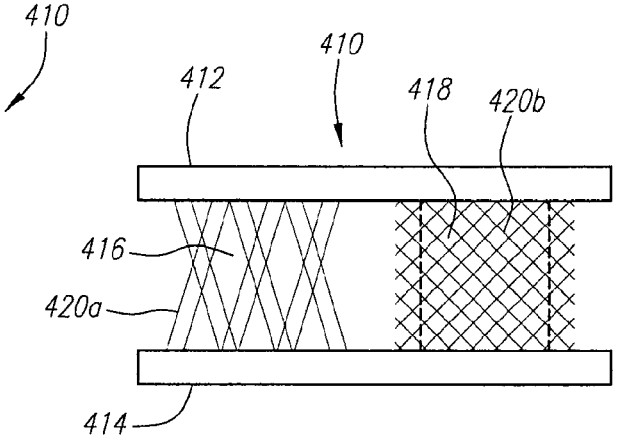

A pair of prosthetic discs 410 are shown in a top view in FIG. 16A. Each of the prosthetic discs 410 includes a generally bullet shaped upper endplate 412 and a generally bullet shaped lower endplate 414, each having an anterior end A and a posterior end P. Each prosthetic disc 410 also includes an anterior core member 416 and a posterior core member 418 located between and supporting the upper and lower endplates. The anterior core members 416 and posterior core members are preferably generally cylindrical, and may be formed of any of the materials and have any of the constructions of the core members described in the preceding section or in the '276 application, provided, however, that the anterior core members 416 are relatively larger and axially stiffer than the posterior core members 418. The larger size and stiffness of the anterior core members may be provided by selection of materials, by the form of construction, by the provision of a fiber wrapping, or by other mechanisms described elsewhere herein or otherwise known to those skilled in the art. In this way, the anterior core members 416 provide many of the physiological functions of the natural disc, and the posterior core members 418 provide many of the physiological functions of the facets. For example, as illustrated in FIG. 16B, a fiber wrapping 420a applied to the anterior core member 416 includes fibers wound in a relatively more vertical pattern in comparison with the pattern of the fibers 420b wound around the posterior core member 418. In this manner, the anterior core member portion of the disc is more rotationally compliant than the posterior core member section, in the manner of the natural disc. The posterior core member section, on the other hand, is relatively rotationally stiff, in the manner of the natural facets.

Figure 16C:
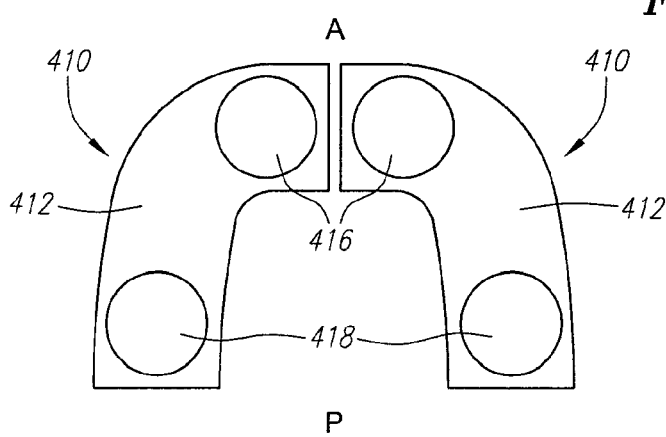

In another alternative construction, a pair of prosthetic discs 410 are shown in FIG. 16C. Each of the prosthetic discs includes upper and lower endplates 412, 414 that each have a generally curved shape such that the posterior ends P of each of the prosthetic discs 410 are in a generally parallel alignment but the anterior ends A of each of the discs are in an abutting arrangement facing one another. In this orientation, the anterior core members 416 are located closer to the saggital midline in comparison with the posterior core members 418. The anterior portions of the combination of the two prosthetic discs are thus more rotatationally compliant and more compliant in lateral bending, comparable to the natural disc. The posterior portions of the combination of the two prosthetic discs, on the other hand, are stiffer and less rotationally compliant, comparable to the natural facets.

Turning to FIGS. 17A-B, another embodiment of a prosthetic disc 410 is shown. The prosthetic disc includes an upper endplate 412, a lower endplate 414, and a pair of core members 416, 418 located between and supporting the pair of endplates. The upper endplate 412 is provided with an anchoring fin 422, and the lower endplate is also provided with an anchoring fin 424. A first fiber winding 420a is located around the anterior core member 416, and a second fiber winding 420b is located around the posterior core member 418.

The upper endplate includes a downward extending face 426 at its posterior end. Similarly, the lower endplate includes an upward extending face 428 at its posterior end. Together the upper face 426 and lower face 428 form a pair of matching faces that mimic the translational limiting functions of the natural facet. For example, in the embodiment shown in FIG. 17A, the upper face 426 has a posteriorly angled surface 427, and the lower face 428 has an anteriorly angled surface 429. In the embodiment shown in FIG. 17B, the upper face 426 and lower face 428 have vertical surfaces. Due to their spatial relationship, the two facing surfaces prevent the upper endplate 412 from translating anteriorly, and prevent the lower endplate 414 from translating posteriorly.

A gap 430 is preferably maintained between the bottom portion of the upper face and the lower endplate, and between the top portion of the lower face and the upper endplate. The gap 430 will determine the clearance available for the prosthetic disc to flex and extend due to imparted forces. In the angled construction shown in FIG. 17A, the matching faces will engage with greater force as the upper endplate and lower endplate are more heavily loaded and the prosthetic disc encounters compressive displacement. Accordingly, the matching faces are preferably constructed of a highly wear-resistant material.

An optional gasket 432 is shown in the embodiment illustrated in FIG. 17B. The gasket 432 functions by preventing tissue ingrowth into the interior of the prosthetic disc 410, and to otherwise seal the interior space of the prosthetic disc.

Turning to FIGS. 18A-C, other embodiments of the prosthetic discs 410 are shown. The prosthetic discs each include an upper endplate 412, a lower endplate 414, and a pair of core members (not shown in any of FIGS. 18A-C) located between and supporting the upper and lower endplates. The upper endplate 412 is provided with a downwardly extending matching face 426, and the lower endplate 414 is also provided with an upwardly extending matching face 428. In these embodiments, the matching faces are provided in an offset manner on the external posterior corner of each of the two prosthetic discs. These matching faces are otherwise identical to those described above in relation to FIGS. 17A-B. The offset location of the matching faces provides a mechanism to mimic the torsional resistance provided by the natural facets.

For example, as shown in the posterior view shown in FIG. 18B, the interface of the matching faces 426, 428 of the prosthetic disc 410 located on the right side of the figure resists movement of the upper endplate 412 to the left and anteriorly relative to the lower endplate 414. Similarly, the interface of the matching faces 426, 428 of the prosthetic disc located on the left side of the figure resists movement of the upper endplate 412 to the right and anteriorly relative to the lower endplate 414. An opposite lateral resistance orientation is obtained by reversing the relative orientation of the matching faces, as shown in FIG. 18C.

Figure 19A:
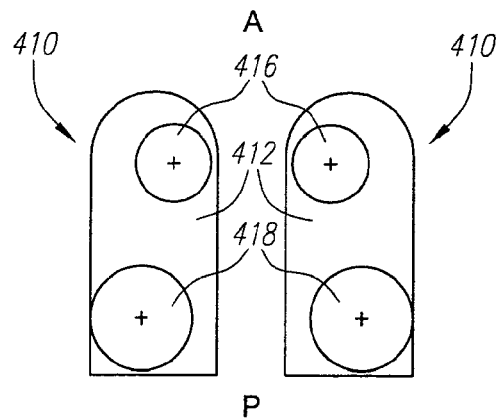
Figure 19B:
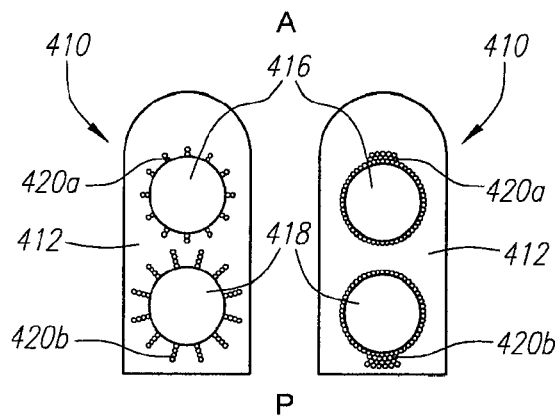
Figure 19C:
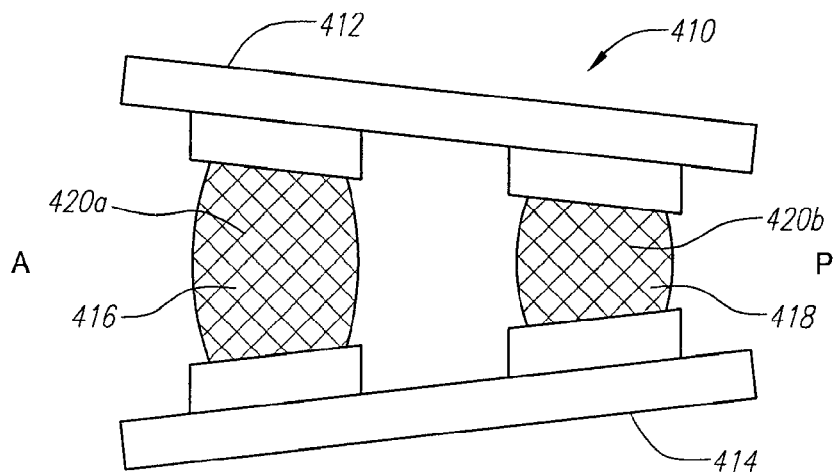

The physiological functions of anterior-posterior resistance and torsional (lateral) resistance otherwise performed by the natural facets may be mimicked by the materials, construction, and orientation of the core structure of the prosthetic disc. Turning to FIGS. 19A-C, several alternative structures are described for performing these functions. For example, FIG. 19A shows a pair of prosthetic discs 410 in a parallel relationship relative to one another. Each prosthetic disc includes an upper endplate 412, a lower endplate 414, an anterior core member 416, and a posterior core member 418. As shown in FIG. 19A, the posterior core members 418 of the two prosthetic discs are each centered at the posterior end of the respective disc, and each is relatively larger than its respective anterior core member 416. The anterior core members 416 are each located near the inner edge of the endplates, thereby placing the centers of the anterior core members 416 relatively closer to one another than are the centers of the posterior core members 418. In this orientation, the relatively smaller anterior core members 416 located relatively closer to one another provide for a relatively greater amount of torsion than is allowed by the relatively larger posterior core members 418 that are spaced further apart relative to the anterior core members. In this way, the illustrated orientation produces translation and torsional resistance intended to mimic the natural physiological forces imparted by the functional spinal unit.

Similarly, in the prosthetic discs 410 illustrated in FIG. 19B, fibers 420a, 420b are wound in patterns surrounding each of the anterior core members 416 and posterior core members 418 of the pair of prosthetic discs. In the disc on the left in the figure, the posterior core member 418 is wound with relatively more fibers 420b than the fiber windings 420a surrounding the anterior core member 416. This will provide a relatively greater limit to torsional and translational movement at the posterior end P of the disc than is allowed at the anterior end A of the disc. In the disc on the right of the figure, fiber windings 420a, 420b are concentrated on the anterior and posterior margins of the prosthetic disc, thereby resisting anterior-posterior translation relative to lateral translation.

Finally, in the prosthetic disc 410 illustrated in FIG. 19C, the anterior core member 416 is relatively taller than the posterior core member 418. Each core member is provided with a fiber winding layer 420a, 420b around its periphery. The relatively taller anterior core member 416 allows a relatively greater amount of translational and rotational freedom than is allowed by the shorter posterior core member 418.

Advantageously, the several features described above in relation to the prosthetic discs shown in FIGS. 16A-C, 17A-B, 18A-C, and 19A-C may be combined in other combinations to obtain a desired biomechanical reproduction of the functional spinal unit.

Turning now to FIGS. 20-21, there is illustrated an endplate 430 comprising an outer endplate 432 and an inner endplate 434. The general design and construction of the endplate is described in the '276 application. The inner endplate 434 includes a post 436 that extends through a mating hole 438 in the outer endplate 432, and the peripheral edge 440 of the inner endplate rests in a recess 442 formed on the inner surface of the outer endplate 432. The inner endplate 434 is then welded to the outer endplate 432 at the post 436 and at the peripheral engagement surface 440. In prior designs, a great deal of stress is created in the weld joints holding the inner and outer endplates together. In the design illustrated in FIGS. 20-21, the inner endplate is provided with four peripheral wings 444 that extend radially outward at equispaced positions around the periphery of the inner endplate 434. Similarly, the outer endplate 432 is provided with four mating recesses 446 that are adapted to receive and retain the wings 444 formed on the inner endplate. The inner endplate 434 is then welded to the outer endplate 432 at the locations of the interfaces between the extensions 444 and the recesses 446, thereby distributing the stresses over a larger area.

An alternative construction for attaching upper and lower endplates is shown in FIG. 28. A prosthetic disc 410 includes an upper endplate 412, a lower endplate 414, and a core member 416. This general construction may comprise any of the specific embodiments described above, those described in the '276 application, or others known in the art. A plurality of fibers 420 extend between and are connected to each of the upper endplate 412 and the lower endplate 414 around the periphery of the core member 416. The fibers 420 provide structural integrity to the prosthetic disc 410 and retain the endplates together on opposed sides of the core member 416.

To better mimic the physiological function of the natural disc, the prosthetic disc 410 shown in FIG. 28 includes five layers of fibers 420 extending from the outer periphery inward toward the core member 416. The outermost fiber layer 421 is preferably formed using fibers that are relatively stiff and inelastic. The innermost fiber layer 423, on the other hand, is preferably formed using fibers that are more flexible and compliant. The intermediate layers of fibers are preferably formed of fibers having an intermediate range of stiffness and elasticity.

It is contemplated that more or fewer fiber layers 420 may be included in the structure while obtaining the same or similar performance by providing stiffer fibers on the outer periphery and ranging to relatively flexible fibers on the interior of the prosthetic disc. Alternatively, the stiffness range may be reversed, such that the stiffer fibers are provided on the interior of the disc near the core member, and the fibers are provided that have gradually less stiffness toward the outer periphery of the disc. Other variations are also contemplated.

IV. Endplate Fixation Mechanisms

A number of mechanisms suitable for fixation of endplates to vertebral bodies will now be described. These fixation mechanisms are typically adapted for use with endplates incorporated in the prosthetic discs described herein and elsewhere. Other uses for these fixation mechanisms will also be apparent from consideration of the descriptions below.

Turning first to FIGS. 22A-D, an endplate 450 for use in a prosthetic disc includes a plurality of fixed anchoring fins 452 on its outer surface. The fixed anchoring fins 452 are adapted to engage grooves that are cut in the inward facing surface of the vertebral body, as described, for example, in the '276 application. Although these anchoring fins 452 are intended to fixedly engage the endplate to the vertebral body, it commonly happens that the anchoring fin 452 is able to migrate within the groove. In the course of doing so, the prosthetic disc will be moved from its preferred location.

To remedy this situation, retractable or moveable spikes 454 or fins 456 are placed on the endplate 450 in a manner that allows their selective engagement. The retractable or moveable fins 456 provide additional fixation to the vertebral body. Advantageously, the retractable or moveable fins 456 are oriented at an angle, preferably a right angle, relative to the fixed anchoring fins 452 located on the outer surface of the endplate. In this way, once they are engaged, the retractable or moveable fins 456 prevent unwanted migration of the endplate 450 and, hence, the prosthetic disc. FIG. 22A, for example, illustrates a top view showing the fixed anchoring fins 452 and a plurality of retractable fins 456, each in its extended state. FIG. 22B is a cross-sectional view illustrating the fixed anchoring fins 452 and the retractable fins 456, also in the extended state.

The retractable fins 456 may be moved from an undeployed to a deployed state by one of many suitable mechanisms. For example, an expansion balloon 458 may be deployed between the upper and lower endplates 450, 460 after deployment. See, e.g., FIG. 22D. The expansion balloon may be expanded to cause the retractable fins 456 to move from an undeployed state to the deployed state, extending outward from the outer facing surfaces of the endplates 450, 460. Other mechanical spacer or screw-type devices 462 could alternatively be used to perform the deployment function. See. e.g., FIG. 22C.

Turning next to FIGS. 23A-B, a partially cylindrical endplate 470 and removable keel 472 are shown. The partially cylindrical endplate 470 is generally similar to that described above in relation to FIGS. 13 and 15A-B. The removable keel 472 is an elongated member having a generally triangular cross section. The base 474 of the triangular cross-section of the keel 472 is adapted to engage an elongated trapezoidal slot 476 formed on the upper surface of the endplate. Accordingly, the endplate 470 may be deployed initially not having the removable keel 472 in order to minimize the profile of the endplate for implantation. Once implanted, the keel 472 may be attached to the endplate 470 by sliding the base portion 474 of the keel lengthwise into the trapezoidal slot 476. The keel 472 is then in position to engage the surface of the vertebral body to fix the endplate in place relative to the vertebral body upon deployment of the prosthetic disc.

A selectively deployable fixation screw and its associated mechanism are shown in FIGS. 24A-B and 25A-C. The fixation screw 480 is adapted for use in a prosthetic disc having an endplate 482 formed of an inner endplate portion 484 and an outer endplate portion 486, in which the inner endplate portion 484 is capable of rotation relative to the outer endplate portion 486. The threaded fixation screw 480 is located in a slot 488 formed in the inner endplate 484 of the prosthetic disc. The fixation screw 480 is retained in the slot 488 such that the screw is able to travel axially within the slot but cannot rotate relative to the inner endplate 484. The outer endplate 486 includes a threaded hole 490 through which the fixation screw 480 extends. Thus, rotation of the inner endplate 484 relative to the outer endplate 486 causes the fixation screw 480 to advance through the slot 488 in the inner endplate and out of the hole 490 in the outer endplate.

Figure 24A:
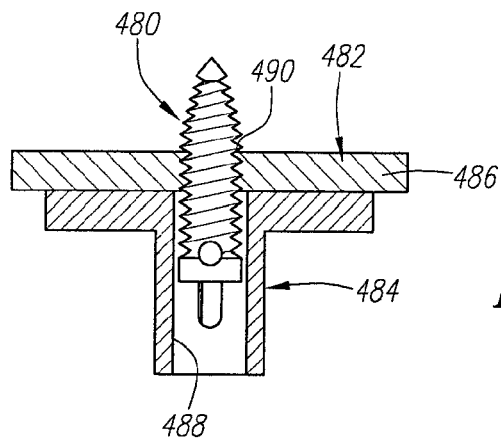
Figure 24B:
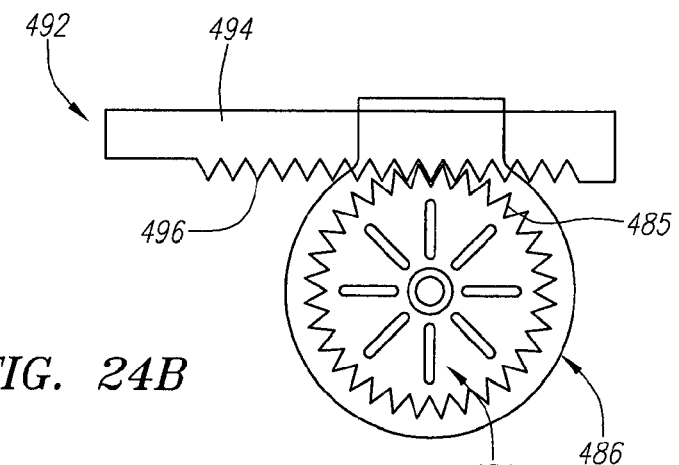

FIG. 24B illustrates a mechanism 492 adapted to effect rotation of the inner endplate 484 relative to the outer endplate 486 as described above. The mechanism 492 includes an elongated actuator 494 having a plurality of teeth 496 formed along an edge thereof. The inner endplate 484 is also provided with teeth 485 that are adapted to mate with the actuator teeth 496. When the teeth are engaged, advancement of the actuator 494 causes rotation of the inner endplate 484 relative to the outer endplate 486, thereby causing the retractable fixation screw 480 to extend outward and engage the vertebral body. Withdrawal of the actuator 494 (while the teeth are engaged) would cause retraction of the fixation screws.

Figure 25A:
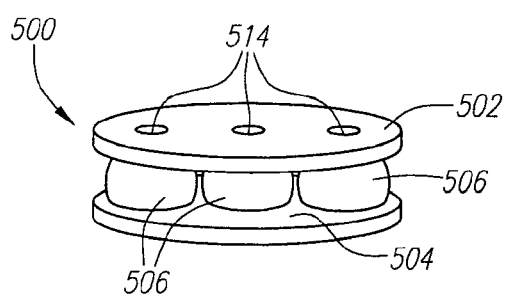
Figure 25B:
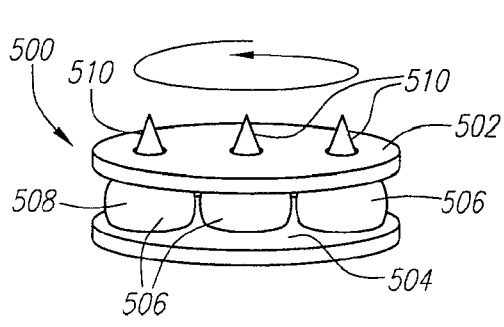
Figure 25C:
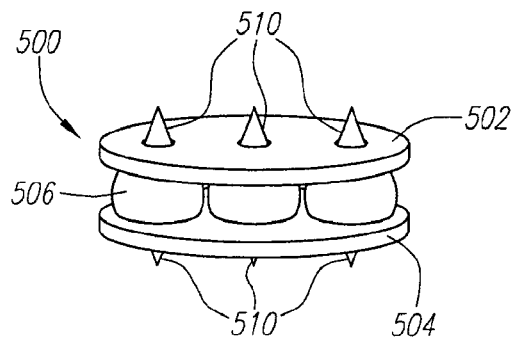

FIGS. 25A-C illustrate a prosthetic disc 500 having a similar retractable fixation mechanism structure. The prosthetic disc 500 includes an upper endplate 502, a lower endplate 504, and three core members 506 located between the upper and lower endplates. Each core member 506 includes a compressible inner member 508 which may be optionally spring-loaded, and an upper fixation member 510 and a lower fixation member 512. The fixation assembly is constructed such that rotation of an inner endplate member (not shown) associated with each of the three core members 506, (see FIG. 25B), causes the respective fixation member 510, 512 to extend outward through holes 514 in the outer surface of the respective outer endplates (see FIG. 25C).

The retractable fixation screw structures so described provide an ability to deliver a prosthetic disc in a relatively lower profile condition during, for example, a minimally invasive implantation procedure. As shown in FIG. 25A, the prosthetic disc 500 has a relatively shorter height prior to extension of the fixation screws 510, 512. When the prosthetic disc is delivered in this condition, less of the spinal bony mass must be removed to provide access to the intervertebral disc space. In addition, there is a reduced likelihood of an occurrence of damage to the adjacent tissue, e.g., nerves, during insertion. After insertion, the retractable fixation screws 510, 512 are extended, as shown, for example, in FIGS. 25A-B, to secure the prosthetic disc to the adjacent vertebral bodies.

Another alternative fixation mechanism is shown in FIGS. 26A-C. This mechanism is also intended to provide a lower profile structure during the implantation procedure. The lower profile will reduce the likelihood of tissue or nerve damage caused by the fixation mechanism, and, in the case of a posterior implantation, will reduce the size of the laminotomy and facetectomy required to accommodate the implantation.

Turning to the Figures, FIG. 26A illustrates a pair of prosthetic discs 520 after a posterior minimally invasive implantation. Each of the prosthetic discs 520 is generally lozenge-shaped, and the pair is provided in a parallel orientation within the intervertebral disc space. A plurality of anchoring spikes 522 extend radially outward from the sides of each of the prosthetic discs. The spikes extend into and engage the remnant portions of the natural disc that remains within the intervertebral disc space after implantation of the prosthetic discs. Preferably, the spikes 522 are provided with a spring mechanism (not shown) that causes each spike to flex outward from the retracted delivery position (FIG. 26B) to the extended deployment position (FIG. 26C) after the prosthetic discs have been implanted. Other actuation mechanisms are contemplated as well. For example, an alternative actuation mechanism includes a screw mechanism that is accessible by the user at the posterior end of each prosthetic disc. Rotation of the screw mechanism is translated by a linkage to cause each spike to extend to the deployment position.

The lateral orientation of the anchoring spikes 522 shown in FIGS. 26A-C may provide sufficient retention force to perform the function of anchoring the prosthetic discs in place. If additional anchoring force is required, more lateral spikes may be added to the structure. Alternatively, or additionally, anchoring fins may also be included on the outer surfaces of the upper endplate and lower endplate to engage the inner surfaces of the vertebral bodies. Additional fixation may be provided by suturing or surgically stapling the disc to the remnant natural disc.

Another embodiment of a selectively removable fixation member is shown in FIGS. 27A-C. The fixation member comprises an insertable keel structure 530 adapted to selectively attach to the outer surface of a prosthetic disc endplate, such as those endplates described herein, in the '276 application, and elsewhere. The keel 530 includes a base portion 532 and an anchoring fin 534 extending upward from the upper surface of the base portion. An attachment member 536 is formed on the bottom surface of the base portion 532. In the embodiment shown, the attachment member 536 is a generally trapezoidal extension that is adapted to slide into a mating trapezoidal slot formed on the outer surface of the endplate, thereby attaching the keel 530 to the endplate. The anchoring fin includes three peaks 538a-c, although more or fewer peaks may be provided. The anchoring fin 534 is adapted to physically engage the inner face of the vertebral body to thereby retain the prosthetic disc in place.

Advantageously, the base portion 532 of the removable keel is in the form of a generally wedge-shaped member having an upper surface that is located in a plane at an acute angle β relative to the plane of the lower surface of the base portion. The purpose for the wedge shape of the removable keel is to provide a lordosis angle to accommodate the angle between the vertebral bodies, particularly in the case of lumbar prosthetic disc implants. In this manner, the endplates of the prosthetic disc may be provided such that they are in a parallel relationship relative to one another, and the removable keel provides the preferred lordosis angle for the prosthetic disc structure.

V. Prosthetic Disc Systems

A number of systems and optional features that may be incorporated in or with a prosthetic disc will now be described.

Turning first to FIGS. 29A-B, a system is shown for maintaining a prosthetic disc in a low profile condition during an implantation procedure. The system includes a prosthetic disc 550 having an upper endplate 552, a lower endplate 554, and a core member 556 located between and attached to the upper endplate and lower endplate. A retention mechanism 558 extends between the upper endplate 552, the core member 556, and the lower endplate 554. Preferably, the retention mechanism 558 extends through a hole formed in each of the upper and lower endplates 552, 554 for the purpose, and a channel through the core member 556.

The retention mechanism 558 acts to selectively maintain the prosthetic disc 550 in a compressed, low profile condition. In particular, the retention mechanism 558 includes a shaft 560 that extends through the prosthetic disc, an upper attachment mechanism 562 that attaches the shaft 560 to the upper endplate 552, and a lower attachment mechanism 564 that attaches the shaft 560 to the lower endplate 554. One example of an attachment mechanism is shown in FIG. 29B, in which the end of the shaft 560 is provided with a notch 561 that engages a keyhole 566 formed in a locking plate 568. A locking plate 568 is slidably attached to one or both of the upper endplate 552 and the lower endplate 554, and the notch 561 at the end of the shaft 560 engages the keyhole 566, locking the shaft 560 in place relative to the locking plate 568. When the locking plate 568 slides, the shaft 560 is allowed to pass through the keyhole 566, releasing the retention mechanism. Other attachment mechanisms are also contemplated.

In practice, prior to implantation, the prosthetic disc 550 is compressed to a height that is reduced relative to its operational height. The retention mechanism 562, 564 is then engaged, effectively restraining the compressed disc from expanding to its operational height. The compressed disc is then implanted, preferably by a minimally invasive surgical procedure. Once the disc has been placed into the intervertebral space, the retention mechanism 562, 564 is disengaged by, for example, sliding the locking plate 568 to release the shaft 560 end through the keyhole 566. The unrestrained prosthetic disc is thus returned to its operational height, and is in operational condition.

Turning now to FIG. 30, a core structure for use in a spinal implant device is shown. The core structure is adapted to provide a method for adjusting the torsional stiffness of the spinal implant device. For example, the core structure includes a generally cylindrical core member 570 formed of materials and in a manner such as those described above. The core member includes a plurality of generally cylindrical recesses 572 extending down from the upper surface and up from the bottom surface of the core member. The core member 570 is thus configured to engage an upper endplate having a mating plurality of generally cylindrical pins extending downward from the inner surface of the upper endplate. The core member 570 is also configured to engage a lower endplate having a mating plurality of generally cylindrical pins extending upward from the inner surface of the lower endplate. The interaction of the recesses formed in the core member and the pins formed on the inner surfaces of the upper endplate and lower endplate causes the core member to be rotationally fixed to both of the endplates.

Advantageously, the numbers, sizes, shapes, materials, and material properties of the core member recesses 572 and the mating endplate pins are subject to design choice in order to obtain a desired performance. For example, the recesses 572 may be provided relatively shallow and the pins provided relatively short to obtain a relatively lower degree of torsional stiffness between the core member and the endplates. Lengthening the recesses 572 and endplate pins will tend to increase the degree of torsional stiffness. Other variations are also contemplated, including location of the pins (and recesses) with respect to the central axis of the endplates. Also, the recesses 572 may be formed on the endplates and mating pins formed on the upper and lower surfaces of the core member to achieve other desired results.

Turning now to FIGS. 31A-D, a preferred system of spinal motion preservation devices is shown. Spinal motion preservation devices are used to treat disorders or diseases of the spine. Two types of such preservation devices are total artificial discs and dynamic stabilization devices. These devices are used to treat, for example, degenerative disc disease and spondylolisthesis. Although such devices have been used independently, they have not been used in conjunction with one another in the manner described herein.

For example, FIG. 31A shows a dynamic stabilization device 580 attached to the transverse processes 582, 584 of a pair of adjacent vertebral bodies 586, 588. The dynamic stabilization device 580 includes an upper attachment member 590 (such as a pedicle screw) that provides an attachment to the upper vertebral body 586, a lower attachment member 592 (such as a pedicle screw) that provides and attachment to the lower vertebral body 588, and a stabilizer 594 extending between and connected to each of the upper attachment member 590 and the lower attachment member 592. The construction and functional details of the dynamic stabilization device 580 are beyond the scope of the present description. Most are generally known to those skilled in the art, and are generally available in the industry literature.

A prosthetic disc 600 is located in the intervertebral space between the two vertebral bodies 586, 588. Natural discs 610 are located in the intervertebral spaces above and below the prosthetic disc 600. The prosthetic disc 600 includes an upper endplate 602, a lower endplate 604, and a core member 606 extending between and attached to each of the upper endplate 602 and lower endplate 604. The prosthetic disc 600 may be constructed according to any of the embodiments described herein, in the '276 application, or elsewhere.

One or more motion preservation devices (including prosthetic discs, dynamic stabilization devices, interspinous spacers, and others) may also be combined with replacement devices, such as facet or vertebral body replacements.

A "lozenge" shaped prosthetic disc 620 is shown in FIG. 31B. The disc 620 is similar to those described above and in the '276 application, including an upper endplate 622 having a plurality of anchoring fins 623, a lower endplate 624 having a plurality of anchoring fins 625, and a pair of core members 626a, 626b extending between and attached to each of the upper endplate and the lower endplate. The "lozenge" shaped prosthetic disc 620 is particularly adapted to be implanted by a minimally invasive surgical procedure using a posterior access. The prosthetic disc 620 so described is suitable for use in combination with one or more dynamic stabilization devices 580 in the manner described above.

Alternatively, as shown in FIGS. 31C-D, the prosthetic disc 620 and dynamic stabilization device 580 may be merged into an integrated structure. FIG. 31C illustrates a first embodiment of such a device, including a prosthetic disc 620 having an upper endplate 622, a lower endplate 624, and a pair of core members 626a-b extending between and attached to each of the upper endplate and lower endplate. The prosthetic disc is in the "lozenge" shape similar to that described above in relation to FIG. 31B. As shown in FIG. 31D, in an alternative embodiment the prosthetic disc 630 includes an upper endplate 632 and lower endplate 634 that are angled to facilitate insertion of the device in a minimally invasive surgical procedure. A dynamic stabilization device 580 is attached to the posterior side of the prosthetic disc 630. The dynamic stabilization device 580 is able to restrain movement of the vertebral bodies to which it is attached in either or both of the axial and lateral directions, to accommodate varying anatomical structures.

Turning now to FIGS. 32A and 32B, where two or more prosthetic disc implants are employed within one disc space, the discs may be positioned spaced apart or engaged with each other. In the latter event, the engagement may be end to end, side to side, or end to side. To facilitate positioning and alignment of two or more discs relative to each other, one or more components or portions of components may be configured to interlock with each other. For example, the peripheral edge of one or more endplates or the sides of the gaskets may be keyed to maintain locked engagement between the discs. FIG. 32A show interlocking disc endplates 110 having annular tongue-and-groove configurations 640. Similarly, the disc gaskets 132 of FIG. 32B are configured with interlocking bellows 650. Each of these interlocking mechanisms facilitates positioning and alignment of the adjacent prosthetic discs relative to one another.

FIGS. 33A-C illustrate prosthetic disc mechanisms adapted to be deployed in an approximately X-shaped configuration. The approximately X-shaped configuration is believed to provide better alignment of the natural center of rotation and to provide support for lateral bending, flexion, and extension. As shown in FIG. 33A, the approximately X-shaped configuration may be obtained by providing a pair of curved prosthetic discs 660 oriented such that the apices 662 of the curves of each disc are pointed toward one another and located near the center 664 of the intervertebral disc space.

Alternatively, as shown in FIG. 33B-C, each of the prosthetic discs may be provided with an upper endplate and lower endplate each having a central (or off-center) linkage 670. The core members are located between and attached to each of the upper endplate and the lower endplate, preferably on either side of the linkage. As shown in FIG. 33B, the prosthetic disc may be implanted while in its straight orientation, thereby minimizing its implantation profile. Then, after implantation, the prosthetic discs may be curved by pivoting the ends of the disc through the linkage 670, thereby forming curved prosthetic discs such as those shown in FIG. 33A.

FIGS. 34A-B illustrate a surgical method for implanting a prosthetic disc using a single implant, single sided posterior approach. As shown, for example, in FIG. 34A, posterior access 680 is created to the intervertebral disc space 682, and a cannula 684 is inserted to maintain the access. A generally lozenge shaped prosthetic disc 686 is inserted through the cannula 684 to the intervertebral disc space 682, with the longitudinal axis extending in the same axis as the cannula. An insertion tool 688 having a gripping end 690 facilitates insertion of the prosthetic disc 686. As shown in FIG. 34A, upon initial insertion, the prosthetic disc 686 is misaligned by 90° from the desired alignment within the disc space 682.

Turning to FIG. 34B, the misalignment of the prosthetic disc is corrected by gripping the disc using the insertion tool 688 and rotating the disc 686 through a 90° rotation until the longitudinal axis of the prosthetic disc is located perpendicular to the insertion path. After rotation, the prosthetic disc 686 is in proper alignment within the disc space 682.

FIGS. 35A-D illustrate an alternative minimally invasive surgical procedure for implantation of one or more prosthetic discs. The illustrated procedure employs a lateral approach that avoids several of the disadvantages inherent in either of the posterior approach or anterior approach. As shown in FIG. 35A, a cannula 700 is inserted laterally through the patient's side to provide access to the intervertebral disc space 702. A pair of generally lozenge shaped prosthetic discs 704*a-b* is aligned for insertion through the cannula into the disc space.

Turning to FIG. 35B, when the leading prosthetic disc 704*a* exits the cannula 700 into the disc space 702, the distal edge of the following prosthetic disc 704*b* contacts the proximal edge of the leading prosthetic disc 704*a* at an angle. The angular contact causes the leading prosthetic disc 704*a* to shift posteriorly within the disc space 702, while the following prosthetic disc 704*b* shifts anteriorly. (See FIG. 35 C). After further advancement of the following prosthetic disc 704*b*, the leading disc 704*a* and following disc 704*b* arrive at a final parallel orientation, as shown in FIG. 35D.

FIGS. 36A-J illustrate several embodiments of an interlocking mechanism suitable for interlocking a pair of adjacent prosthetic discs 710, such as those described above in relation to FIG. 35D. Turning first to FIGS. 36A-B, these figures illustrate side and top views, respectively, of a first prosthetic disc 710 having a first attachment mechanism 712. The first attachment mechanism 712 is in the form of a plurality of pins projecting from the sides of the upper and lower endplates 714, 716 of the prosthesis. As shown in the illustrated example, two pins project from the side of each of the upper endplate 714 and the lower endplate 716. More or fewer pins may be suitable.

Turning next to FIGS. 36C-D, these figures illustrate side and top views, respectively, of a second prosthetic disc 720 having a second attachment mechanism 722, with the second attachment mechanism being complementary to the first attachment mechanism 712 shown in FIGS. 36A-B. The second attachment mechanism 722 is in the form of a matching plurality of angled ramps projecting from the sides of each of the upper and lower endplates 724, 726 of the prosthesis.

Next, turning to FIGS. 36E-F, these figures illustrate side and top views, respectively, of a third prosthetic disc 730 having a third attachment mechanism 732, which third attachment mechanism 732 is also complementary to the first attachment mechanism 712 shown in FIGS. 36A-B. The third attachment mechanism 732 is in the form a matching plurality of C-shaped clamps projecting from the sides of each of the upper and lower endplates 734, 736 of the prosthesis.

FIG. 36G shows the first and second prosthetic discs 710, 720 depicted in FIGS. 36A-B and FIGS. 36C-D, respectively, partially assembled with the first attachment mechanism 712 pins as shown in FIGS. 36A-B moving laterally to the right and slightly down to partially engage the second attachment mechanism 722 ramps as shown in FIGS. 36C-D which are moving to the left and slightly up. The two-component disc prosthesis is shown fully assembled in FIG. 36H with the pins dropped behind the back of the ramps, thereby preventing movement of pin half of the prosthesis to the left and movement of the ramp half of the prosthesis to the right. FIG. 36I shows the alternative third attachment mechanism 732 depicted in FIGS. 36E-F fully assembled with the first prosthetic disc 710 depicted in FIGS. 36A-B by use of the projecting pins of the first attachment mechanism 712 depicted in FIGS. 36A-B fully snapped into the projecting clamps of the third attachment mechanism 732 depicted in FIGS. 36E-F. It will be appreciated by those skilled in the art that the attachment mechanism shown engaged in FIG. 36I prevents movement of the two halves of the prosthesis relative to each other both laterally in both directions and vertically in both directions.

Turning next to FIGS. 37A-F, another embodiment of a minimally invasive surgical procedure for delivering a pair of prosthetic disc implants is illustrated. The procedure is intended to provide a repeatable orientation of the implanted discs. It is preferable to provide a method that produces relatively consistent implantation results, because variations in the final positioning of the implanted prosthetic discs relative to one another and relative to the vertebral bodies will create variations in the biomechanical performance of the implanted discs.

Figure 37A:
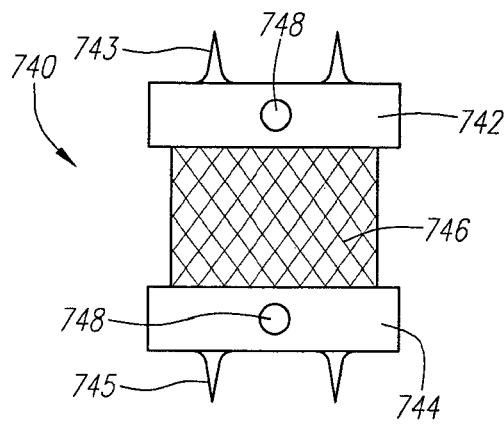
Figure 37B:
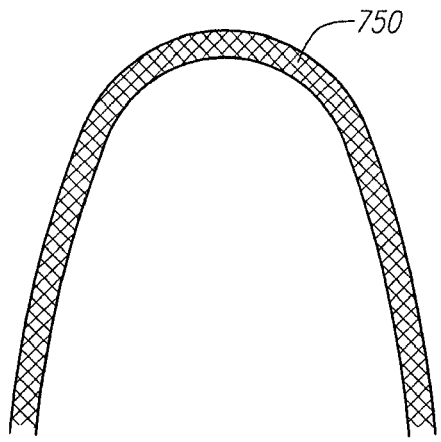
Figure 37C:
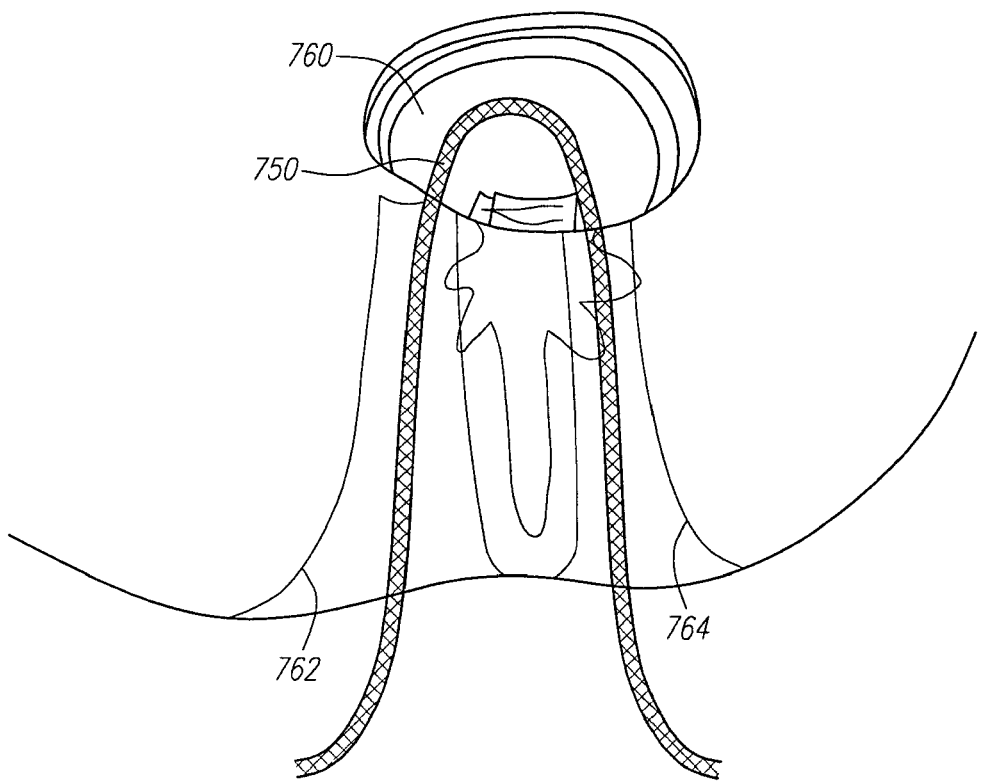

The procedure is adapted for use with a prosthetic disc 740 such as the embodiment shown in FIG. 37A. The disc 740 includes an upper endplate 742 having an optional anchoring fin 743, a lower endplate 744 also having an optional anchoring fin 745, and a core member 746 extending between and attached to each of the upper endplate and lower endplate. A guide channel 748 is formed in each of the upper endplate and lower endplate. The guide channel 748 preferably extends through the length of each of the endplates. A guidewire 750 is shown in FIG. 37B. The guide channel 748 formed in each of the upper endplate 742 and lower endplate 744 of the prosthetic discs 740 is of a size sufficient to allow passage of the guidewire 750. The guidewire 750 is preferably formed of a braided, coiled, monofilament material.

Figure 37D:
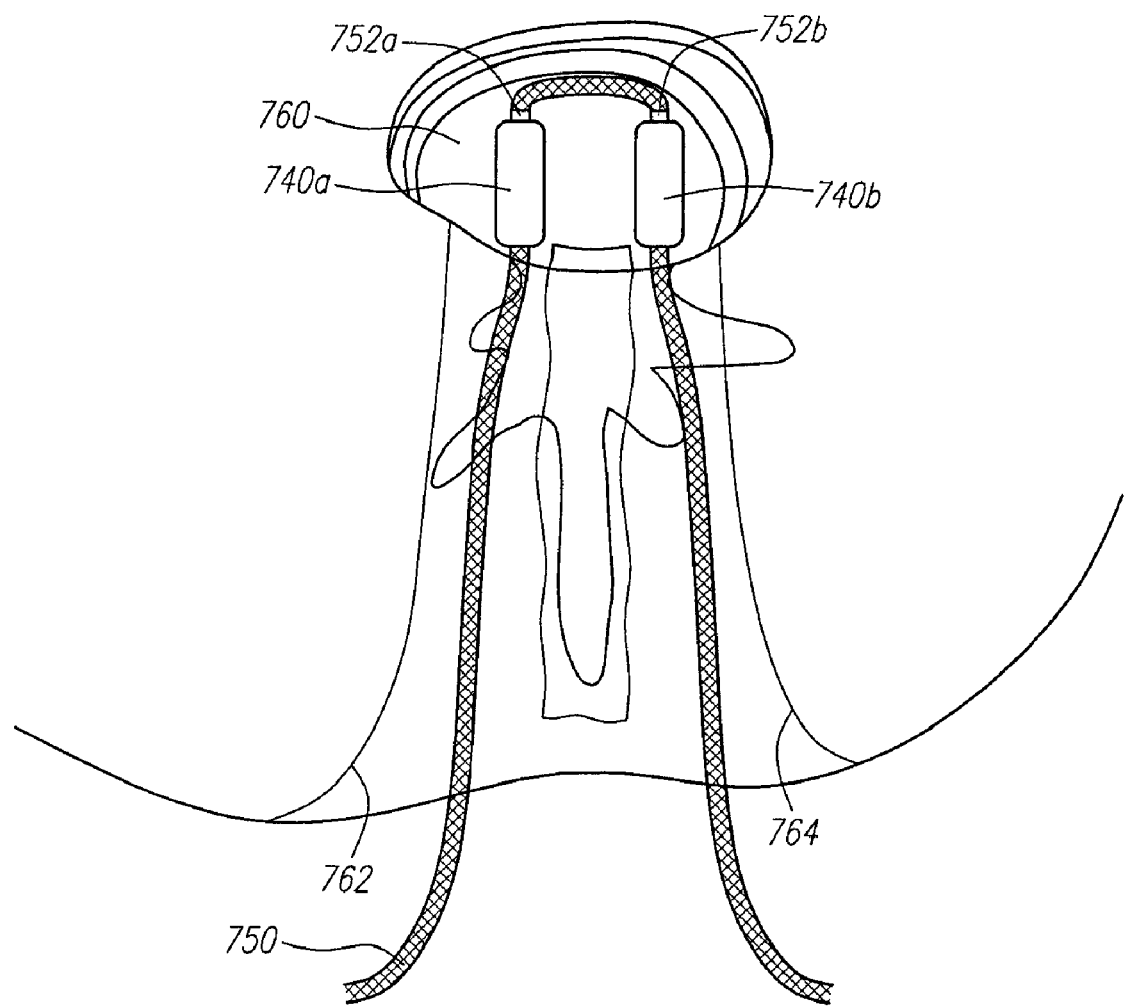
Figure 37E:
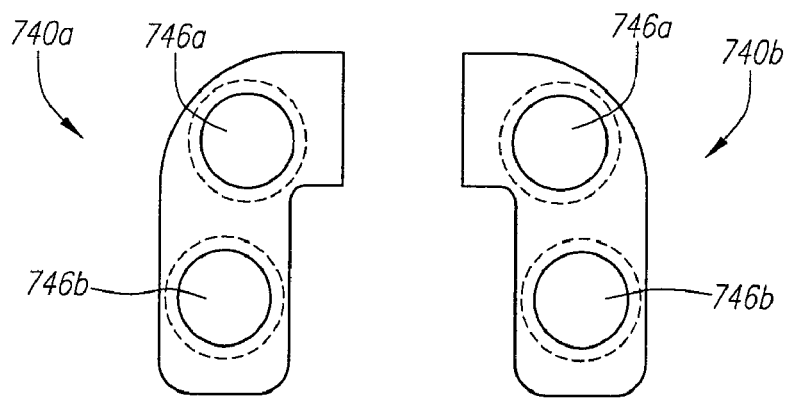

To begin, the surgical procedure entails creation of an access to both sides of the posterior disc space 760. A pair of cannulas 762, 764 is inserted into the incisions to provide the access. The nucleus and the lateral and anterior annulus of the natural disc are removed. (See FIG. 37C). The guidewire 750 is then passed into one of the access channels, through the cleared nuclear cavity, and back out of the opposite access channel. Once the guidewire 750 is in place, a prosthetic disc 740a, 740b is threaded over each of the ends of the guidewire 750, and the pair of prosthetic discs 740a-b is advanced over the guidewire 750 into the cleared nuclear cavity 760, as shown in FIG. 37D. In the preferred embodiment, the guidewire 750 is provided with a pair of fixed stops 752a-b that prevent further advancement of the prosthetic disc 740 along the guidewire 750. Accordingly, provided that the guidewire 750 has been properly positioned within the disc space, each of the prosthetic discs is advanced to a predetermined position within the disc space and relative to one another.

Figure 37F:
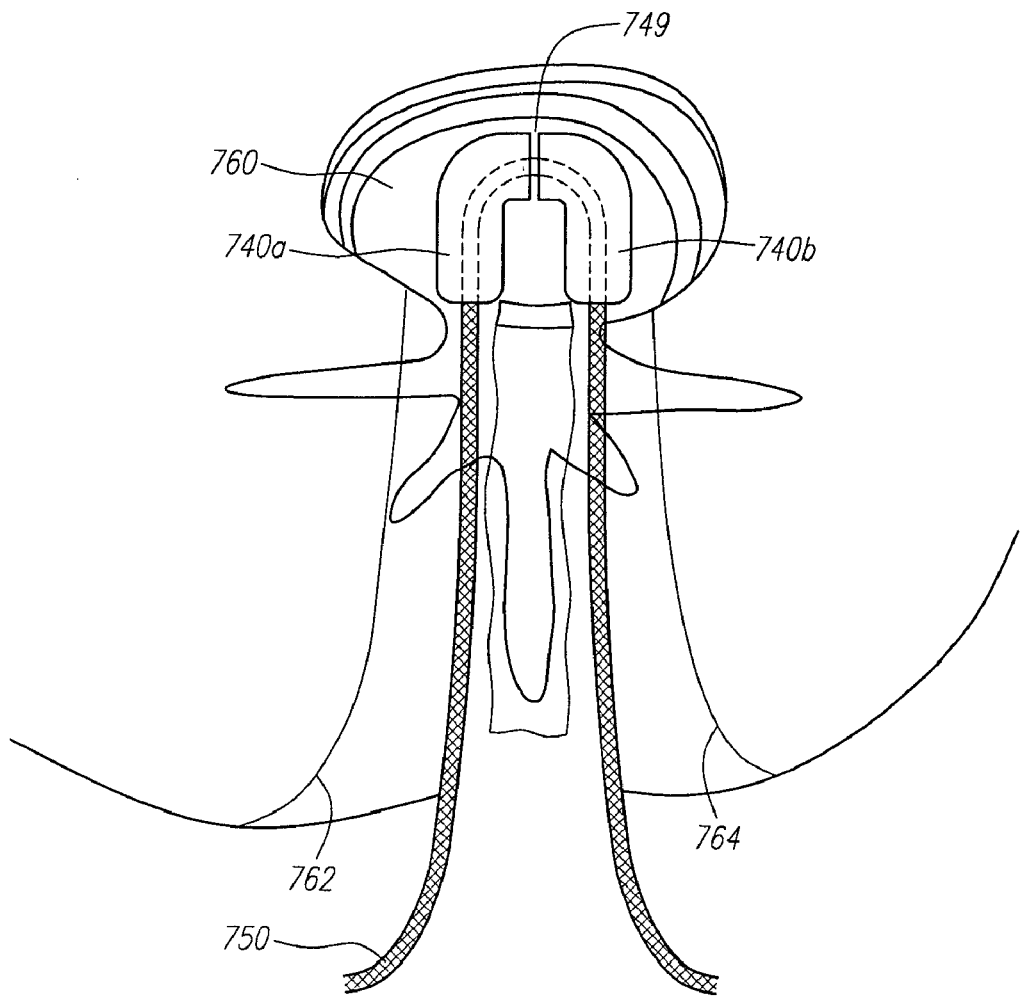

In a particularly preferred embodiment of the foregoing methods, each of the prosthetic discs 740a-b is formed in a "J" shape and each includes a pair of core members 746a-b. See FIG. 37E. In this embodiment, the distal ends of each of the discs butt up against one another (see at 749) within the disc space upon final implantation, as shown in FIG. 37F.

FIGS. 38A-F illustrate several embodiments of the pairs of "J" shaped prosthetic discs 740a-b described above. The pairs of discs shown in these figures include attachment mechanisms that provide the ability to attach the pair of discs 740a-b to one another after deployment. For example, in FIGS. 38A-B, a first prosthetic disc 740a includes an enlarged extension 770 that is sized to provide a snap-fit engagement with a recess 772 formed in the second prosthetic disc 740b. When the distal ends of the discs are forced together, the extension 770 is inserted into the recess 772 and snaps in place, thereby attaching the first disc 740a to the second disc 740b. Similarly, in FIGS. 38C-D, the first prosthetic disc 740a is provided with a hook extension 780 at its distal end that is adapted to engage and attach to a mating slot 782 formed on the distal end of the second disc 740b. Finally, in FIGS. 38E-F, a suture 790 is inserted through the guide channels 748 formed in each of the first prosthetic disc 740a and the second prosthetic disc 740b. After the distal ends of the discs are forced together, a knot 792 is tied in each end of the suture 790 to maintain the relative positions of the pair of prosthetic discs. Alternatively, a clip may be applied to each end of the suture. The ends of the suture may then be trimmed to remove any excess material. Additionally the guide wire can have crimps attached at both ends and the unnecessary portion cut away.

Turning to FIG. 39, an encapsulated spring disc replacement system 800 is shown. The system includes an internal spring element 802 that is contained in an elastomeric capsule 804. The spring element 802 may comprise a flat spring (e.g., elliptic or leaf springs), a spiral spring, a helical spring (e.g., coil springs), or the like. The spring element 802 may be formed of a metallic material (e.g., stainless steel, metal alloys), an elastomeric material, or any other suitable material. The spring element 802 is preferably attached to an upper (superior) fixation member 806 and a lower (inferior) fixation member 808. The upper and lower fixation members 806, 808 may comprise spikes, as shown, or fins, anchors, or any other members suitable for engaging the superior and inferior vertebral bodies to substantially fix the disc replacement system in place. Examples of suitable fixation members are described above. The elastomeric capsule 804 may be generally spherical, cubic, kidney-shaped, or any other size or shape suitable its intended use.

Each encapsulated spring system 800 may be implanted via cannula delivery by compressing the spring element 802 to decrease the profile of the system 800. The encapsulated spring system 800 is then allowed to expand to its normal condition after delivery. In this way, the encapsulated spring system is suitable for deployment and implantation between a pair of adjacent vertebral bodies. A single encapsulated spring system or a small plurality of such systems may be implanted as a partial disc replacement, or to provide disc assistance or disc repair. Alternatively, a relatively larger plurality of encapsulated spring systems may be implanted to provide a total disc replacement.

VI. Information Concerning the Descriptions Contained Herein

It is to be understood that the inventions that are the subject of this patent application are not limited to the particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are herein described.

All patents, patent applications, and other publications mentioned herein are hereby incorporated herein by reference in their entireties. The patents, applications, and publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present inventions.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A prosthetic intervertebral disc for implantation between adjacent first and second vertebrae in human spine comprising:
   a first endplate comprising an inner surface positioned adjacent a compressible core member, the first endplate comprising a plurality of slots, the first endplate being attachable to a first vertebra;
   a second endplate comprising an inner surface positioned adjacent the compressible core member, the second endplate comprising a plurality of slots, the second endplate being attachable to a second vertebra adjacent the first vertebra in a spine;
   the compressible core member positioned between said first and second endplates, the compressible core member comprising a polymeric nuclear domain having an outer surface comprising a plurality of grooves, each groove having a groove width and a groove depth, each groove width and groove depth selected to obtain desired performance characteristics of the core member, and the compressible core member comprising an annular domain surrounding the nuclear domain, wherein the annular domain contains at least one fiber that is engaged with said first and second endplates by extending through the plurality of slots in the first endplate and through the plurality of slots in the second endplate.

2. The prosthetic intervertebral disc of claim 1 wherein each groove width and groove depth is selected to obtain a desired torsional resistance of the core member.

3. The prosthetic intervertebral disc of claim 1 wherein each groove width and groove depth is selected to obtain a desired load bearing capacity of the core member.

4. The prosthetic intervertebral disc of claim 1 wherein said at least one fiber extends through each of said plurality of slots of said first endplate and through each of said plurality of slots of said second end plate.

5. The prosthetic intervertebral disc of claim 1 further comprising fixation members for securing said first and second endplates to vertebral bodies, said fixation members extending from outer surfaces of said first and second endplates.

6. The prosthetic intervertebral disc of claim 5 wherein said fixation members each comprise at least one anchoring fin.

7. The prosthetic intervertebral disc of claim 1 wherein at least one of the first and second endplates comprises a material is selected from the group consisting of titanium, titanium alloys, stainless steel, cobalt/chromium, ultrahigh molecular weight polyethylene (UHMW-PE), polyetheretherketone (PEEK), ceramics, and graphite.

8. The prosthetic intervertebral disc of claim 1 wherein at least one of the first and second endplates comprises titanium or a titanium alloy.

9. A prosthetic intervertebral disc for implantation between adjacent first and second vertebrae in human spine comprising:
   a first endplate comprising an inner surface positioned adjacent a compressible core member, the first endplate comprising a plurality of slots, the first endplate being attachable to a first vertebra;
   a second endplate comprising an inner surface positioned adjacent the compressible core member, the second endplate comprising a plurality of slots, the second endplate being attachable to a second vertebra adjacent the first vertebra in a spine;
   the compressible core member positioned between said first and second endplates, the compressible core member comprising a polymeric nuclear domain having an outer surface, at least one compression member situated on the outer surface of the outer surface domain, and the compressible core member comprising an annular domain surrounding the nuclear domain, wherein the annular domain contains at least one fiber that is engaged with said first and second endplates by extending through the plurality of slots in the first endplate and through the plurality of slots in the second endplate.

10. The prosthetic intervertebral disc of claim 9 wherein the at least one compression member comprises a coiled compression spring.

11. The prosthetic intervertebral disc of claim 9 wherein the at least one compression member comprises a plurality of spaced apart rings.

12. The prosthetic intervertebral disc of claim 9 wherein said at least one fiber extends through each of said plurality of slots of said first endplate and through each of said plurality of slots of said second end plate.

13. The prosthetic intervertebral disc of claim 9 further comprising fixation members for securing said first and second endplates to vertebral bodies, said fixation members extending from outer surfaces of said first and second endplates.

14. The prosthetic intervertebral disc of claim 13 wherein said fixation members each comprise at least one anchoring fin.

15. The prosthetic intervertebral disc of claim 9 wherein at least one of the first and second endplates comprises a material is selected from the group consisting of titanium, titanium alloys, stainless steel, cobalt/chromium, ultrahigh molecular weight polyethylene (UHMW-PE), polyetheretherketone (PEEK), ceramics, and graphite.

16. The prosthetic intervertebral disc of claim 9 wherein at least one of the first and second endplates comprises titanium or a titanium alloy.

17. A prosthetic intervertebral disc for implantation between adjacent first and second vertebrae in human spine comprising:
   a first endplate comprising an inner surface positioned adjacent a compressible core member, the first endplate comprising a plurality of slots, the first endplate being attachable to a first vertebra;
   a second endplate comprising an inner surface positioned adjacent the compressible core member, the second endplate comprising a plurality of slots, the second endplate being attachable to a second vertebra adjacent the first vertebra in a spine;
   the compressible core member positioned between said first and second endplates, the compressible core member comprising a polymeric nuclear domain having a first upper surface adjacent the first endplate and having a second lower surface adjacent the second endplate, the first and second surfaces being configured to provide a plurality of raised portions on the first and second surfaces and an access volume between the core member and the first and second endplates for access of gaseous sterilizing medium, and the compressible core member comprising an annular domain surrounding the nuclear domain, wherein the annular domain contains at least one fiber that is engaged with said first and second endplates by extending through the plurality of slots in the first endplate and through the plurality of slots in the second endplate.

18. The prosthetic intervertebral disc of claim 17 wherein the plurality of raised portions comprise raised portions forming a generally radial pattern extending from a location near the center of the surface radially to the outer edge.

19. The prosthetic intervertebral disc of claim 17 wherein the plurality of raised portions comprise raised, semicircular portions forming a generally circular pattern.

20. The prosthetic intervertebral disc of claim 18 wherein the plurality of raised portions further comprise raised, semicircular portions forming a generally circular pattern.

21. The prosthetic intervertebral disc of claim 17 wherein the plurality of raised portions comprise a plurality of raised bumps.

22. The prosthetic intervertebral disc of claim 17 wherein the plurality of raised portions comprise a polyethylene terephthalate (PET) integrated mesh including a plurality of non-geometric raised portions.

23. The prosthetic intervertebral disc of claim 17 wherein said at least one fiber extends through each of said plurality of slots of said first endplate and through each of said plurality of slots of said second end plate.

24. The prosthetic intervertebral disc of claim 17 further comprising fixation members for securing said first and second endplates to vertebral bodies, said fixation members extending from outer surfaces of said first and second endplates.

25. The prosthetic intervertebral disc of claim 24 wherein said fixation members each comprise at least one anchoring fin.

26. The prosthetic intervertebral disc of claim 17 wherein at least one of the first and second endplates comprises a material is selected from the group consisting of titanium, titanium alloys, stainless steel, cobalt/chromium, ultrahigh molecular weight polyethylene (UHMW-PE), polyetheretherketone (PEEK), ceramics, and graphite.

27. The prosthetic intervertebral disc of claim 17 wherein at least one of the first and second endplates comprises titanium or a titanium alloy.

28. The prosthetic intervertebral disc of claim 17 wherein the polymeric nuclear domain comprises an elastomeric material.

29. The prosthetic intervertebral disc of claim 17 wherein the polymeric nuclear domain comprises an elastomeric material selected from polydimethylsiloxane, polycarbonate-polyurethane, and aromatic and aliphatic polyurethanes.

30. The prosthetic intervertebral disc of claim 17 wherein the polymeric nuclear domain comprises a polycarbonate polyurethane elastomeric material.

31. The prosthetic intervertebral disc of claim 17 wherein the polymeric nuclear domain comprises poly(ethylene propylene) copolymer.

32. The prosthetic intervertebral disc of claim 17 wherein the polymeric nuclear domain comprises polyvinylchloride.

33. The prosthetic intervertebral disc of claim 17 wherein the polymeric nuclear domain comprises poly(tetrafluoro ethylene) and its copolymers.

34. The prosthetic intervertebral disc of claim 17 wherein the polymeric nuclear domain comprises a hydrogel.

* * * * *

UNITED STATES PATENT AND TRADEMARK OFFICE

(12) CERTIFICATE EXTENDING PATENT TERM
UNDER 35 U.S.C. § 156

| | | | |
|---|---|---|---|
| (68) | PATENT NO. | : | 8,377,138 |
| (45) | ISSUED | : | February 19, 2013 |
| (75) | INVENTOR | : | Reo et al. |
| (73) | PATENT OWNER | : | Spinal Kinetics LLC |
| (95) | PRODUCT | : | M6-C® Artificial Cervical Disc |

This is to certify that an application under 35 U.S.C. § 156 has been filed in the United States Patent and Trademark Office, requesting extension of the term of U.S. Patent No. 8,377,138 based upon the regulatory review of the product M6-C® Artificial Cervical Disc by the Food and Drug Administration. According to United States Patent and Trademark Office records, the original expiration date of the patent as of the date of issuance of this certificate is November 30, 2025. Because it appears that the requirements of the law have been met, this certificate extends the term of the patent for the period of

(94)                                1,322 days subject to the payment of maintenance fees as provided by law, with all rights pertaining thereto as provided by 35 U.S.C. § 156.

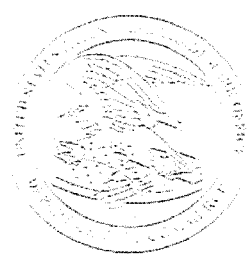

I have caused the seal of the United States Patent and Trademark Office to be affixed this <u>8th day</u> of <u>August 2024</u>.

*Kathi Vidal*

Katherine K. Vidal
Under Secretary of Commerce for Intellectual Property and Director of the United States Patent and Trademark Office